(12) United States Patent
Karp et al.

(10) Patent No.: US 7,261,812 B1
(45) Date of Patent: *Aug. 28, 2007

(54) MULTI-COLUMN SEPARATION DEVICES AND METHODS

(75) Inventors: Christoph D. Karp, Pasadena, CA (US); Joseph F. Covington, San Gabriel, CA (US); Matthew M. Gregori, Pasadena, CA (US); Steven E. Hobbs, West Hills, CA (US); Jeffrey A. Koehler, Pasadena, CA (US); Stephen D. O'Connor, Pasadena, CA (US); Paren P. Patel, Sierra Madre, CA (US); Scott G. Beach, Manhattan Beach, CA (US)

(73) Assignee: Nanostream, Inc., Pasadena, CA (US)

( * ) Notice: Subject to any disclaimer, the term of this patent is extended or adjusted under 35 U.S.C. 154(b) by 550 days.

This patent is subject to a terminal disclaimer.

(21) Appl. No.: 10/638,258

(22) Filed: Aug. 7, 2003

Related U.S. Application Data

(63) Continuation-in-part of application No. 10/366,985, filed on Feb. 13, 2003, now Pat. No. 6,923,907.

(60) Provisional application No. 60/415,896, filed on Oct. 3, 2002, provisional application No. 60/357,683, filed on Feb. 13, 2002.

(51) Int. Cl.
 *B01D 15/08* (2006.01)
(52) U.S. Cl. ............ 210/198.2; 210/656; 422/70; 422/100
(58) Field of Classification Search ......... 210/198.2, 210/656; 422/70, 100; 73/61.52, 61.57; 96/101
See application file for complete search history.

(56) References Cited

U.S. PATENT DOCUMENTS

| 3,449,938 A | 6/1969 | Giddings ............... 73/23 |
| 4,175,037 A | 11/1979 | Benney et al. ......... 210/31 C |
| 4,301,139 A | 11/1981 | Feingers et al. ......... 424/1 |

(Continued)

FOREIGN PATENT DOCUMENTS

EP  1 106 244 A2  6/2001

(Continued)

OTHER PUBLICATIONS

Chen, Xiaoxi et al., *A Prototype Two-Dimensional Capillary Electrophoresis System Fabricated in Poly(dimethylsiloxane)*, "Analytical Chemistry," vol. 74, No. 8, Apr. 15, 2002, pp. 1772-1778.

(Continued)

*Primary Examiner*—Ernest G. Therkorn
(74) *Attorney, Agent, or Firm*—Vincent K. Gustafson; Intellectual Property/Technology Law

(57) ABSTRACT

Chromatographic separation devices include multiple batch-processed columns joined by a body structure and adapted to perform parallel analyses. Both slurry-packed and monolithic column embodiments are provided. One or more liquid-permeable frits of various types may be used to retain stationary phase material within columns. A fluidic distribution network may be used to distribute stationary phase material and/or mobile phase solvents to multiple columns. Separation devices, including microfluidic embodiments, may be fabricated with various materials including polymers. Multi-column fabrication and separation methods are provided.

34 Claims, 31 Drawing Sheets

U.S. PATENT DOCUMENTS

| | | | | |
|---|---|---|---|---|
| 4,324,689 A * | 4/1982 | Shah | | 502/401 |
| 4,424,127 A | 1/1984 | Roeraade | | 210/198.2 |
| 4,496,461 A | 1/1985 | Leeke et al. | | 210/198.2 |
| 4,505,539 A | 3/1985 | Auracher et al. | | 350/96.15 |
| 4,604,198 A | 8/1986 | Dailey et al. | | 210/198.2 |
| 4,868,129 A | 9/1989 | Gibbons et al. | | 436/179 |
| 4,891,120 A | 1/1990 | Sethi et al. | | 204/299 R |
| 5,135,627 A | 8/1992 | Soane | | 204/182.8 |
| 5,160,627 A * | 11/1992 | Cussler et al. | | 210/639 |
| 5,190,658 A | 3/1993 | Vilenchik et al. | | 210/656 |
| 5,194,133 A | 3/1993 | Clark et al. | | 204/299 |
| 5,376,252 A | 12/1994 | Ekström et al. | | 204/299 |
| 5,453,153 A | 9/1995 | Fan et al. | | 117/2 |
| 5,478,751 A | 12/1995 | Oosta et al. | | 436/165 |
| 5,658,413 A | 8/1997 | Kaltenbach et al. | | 156/272.8 |
| 5,792,943 A | 8/1998 | Craig | | 73/61.52 |
| 5,872,010 A | 2/1999 | Karger et al. | | 436/173 |
| 6,004,450 A | 12/1999 | Northrup et al. | | 205/656 |
| 6,054,047 A * | 4/2000 | Hindsgaul et al. | | 210/198.2 |
| 6,066,848 A | 5/2000 | Kassel et al. | | 250/288 |
| 6,074,725 A | 6/2000 | Kennedy | | 428/188 |
| 6,090,278 A | 7/2000 | Lally et al. | | 210/198.2 |
| 6,095,202 A | 8/2000 | Colon et al. | | 141/34 |
| 6,103,199 A | 8/2000 | Bjornson et al. | | 422/100 |
| 6,129,973 A | 10/2000 | Martin et al. | | 428/166 |
| 6,149,815 A | 11/2000 | Sauter | | 210/635 |
| 6,171,486 B1 | 1/2001 | Green et al. | | 210/198.2 |
| 6,197,198 B1 | 3/2001 | Messinger et al. | | 210/656 |
| 6,210,986 B1 | 4/2001 | Arnold et al. | | 438/42 |
| 6,221,252 B1 | 4/2001 | Hargro et al. | | 210/656 |
| 6,224,775 B1 * | 5/2001 | Foley et al. | | 210/635 |
| 6,240,790 B1 | 6/2001 | Swedberg et al. | | 73/863.21 |
| 6,245,227 B1 * | 6/2001 | Moon et al. | | 210/198.2 |
| 6,258,263 B1 | 7/2001 | Henderson et al. | | 210/198.2 |
| 6,261,430 B1 | 7/2001 | Yager et al. | | 204/455 |
| 6,263,918 B1 | 7/2001 | Lewis et al. | | 137/597 |
| 6,264,892 B1 | 7/2001 | Kaltenbach et al. | | 422/68.1 |
| 6,274,726 B1 | 8/2001 | Laugharn, Jr. et al. | | 536/25.4 |
| 6,296,771 B1 | 10/2001 | Miroslav | | 210/656 |
| 6,306,590 B1 | 10/2001 | Mehta et al. | | 435/6 |
| 6,312,888 B1 | 11/2001 | Wong et al. | | 435/4 |
| 6,387,234 B1 | 5/2002 | Yeung et al. | | 204/451 |
| 6,432,290 B1 | 8/2002 | Harrison et al. | | 204/453 |
| 6,436,292 B1 | 8/2002 | Petro | | 210/656 |
| 6,444,150 B1 | 9/2002 | Arnold | | 264/69 |
| 6,444,461 B1 | 9/2002 | Knapp et al. | | 435/283.1 |
| 6,461,515 B1 | 10/2002 | Safir et al. | | 210/656 |
| 6,464,866 B2 | 10/2002 | Moon et al. | | 210/198.2 |
| 6,485,069 B1 | 11/2002 | Anderson | | 292/175 |
| 6,494,614 B1 | 12/2002 | Bennett et al. | | 366/336 |
| 6,497,138 B1 | 12/2002 | Abdel-Rahman et al. | | 73/23.42 |
| 6,527,890 B1 | 3/2003 | Briscoe et al. | | 156/89.11 |
| 6,537,501 B1 | 3/2003 | Holl et al. | | 422/101 |
| 6,537,506 B1 | 3/2003 | Schwalbe et al. | | 422/130 |
| 6,551,839 B2 | 4/2003 | Jovanovich et al. | | 436/180 |
| 6,581,441 B1 | 6/2003 | Paul | | 73/61.52 |
| 6,623,860 B2 | 9/2003 | Hu et al. | | 428/411.1 |
| 6,627,433 B2 | 9/2003 | Frazier et al. | | 435/288.7 |
| 6,635,226 B1 | 10/2003 | Tso et al. | | 422/129 |
| 6,645,377 B1 | 11/2003 | Egorov et al. | | 210/198.2 |
| 6,660,149 B1 | 12/2003 | Karger et al. | | 204/601 |
| 6,663,697 B1 | 12/2003 | Kottenstette et al. | | 96/101 |
| 6,664,104 B2 | 12/2003 | Pourahmadi et al. | | 435/288.6 |
| 6,743,356 B1 * | 6/2004 | Fermier et al. | | 210/198.2 |
| 6,749,749 B2 | 6/2004 | Xie et al. | | 210/198.2 |
| 6,812,030 B2 | 11/2004 | Ozbal et al. | | 436/50 |
| 6,814,859 B2 * | 11/2004 | Koehler et al. | | 210/198.2 |
| 6,923,907 B2 * | 8/2005 | Hobbs et al. | | 210/198.2 |
| 6,986,841 B2 * | 1/2006 | Zare et al. | | 210/198.2 |
| 2002/0017484 A1 | 2/2002 | Dourdeville | | 210/198.2 |
| 2002/0048536 A1 | 4/2002 | Bergh et al. | | 422/130 |
| 2002/0094533 A1 | 7/2002 | Hess et al. | | 435/6 |
| 2002/0146840 A1 * | 10/2002 | Hage et al. | | 436/178 |
| 2002/0158022 A1 | 10/2002 | Huang et al. | | 210/656 |
| 2002/0160139 A1 | 10/2002 | Huang et al. | | 428/36.9 |
| 2002/0189947 A1 | 12/2002 | Paul et al. | | 204/461 |
| 2002/0194909 A1 | 12/2002 | Hasselbrink et al. | | 73/253 |
| 2002/0199094 A1 | 12/2002 | Strand et al. | | 713/150 |
| 2003/0089663 A1 | 5/2003 | Petro et al. | | 210/656 |
| 2003/0092056 A1 | 5/2003 | Nagasawa | | 435/6 |
| 2003/0094415 A1 | 5/2003 | Tanimura | | 210/656 |
| 2003/0118486 A1 | 6/2003 | Zhou et al. | | 422/102 |
| 2003/0230524 A1 | 12/2003 | Soga et al. | | 210/198.2 |
| 2004/0020834 A1 | 2/2004 | Mincsovics et al. | | 210/198.2 |
| 2004/0084375 A1 | 5/2004 | Hodgin et al. | | 210/656 |
| 2004/0134845 A1 | 7/2004 | Paul et al. | | 210/198.2 |

FOREIGN PATENT DOCUMENTS

| | | |
|---|---|---|
| EP | 1178309 A1 | 2/2002 |
| WO | WO97/30347 | 8/1997 |
| WO | WO98/04909 | 2/1998 |
| WO | WO99/19717 | 4/1999 |
| WO | WO99/29497 | 6/1999 |
| WO | WO99/33559 | 7/1999 |
| WO | WO99/34909 | 7/1999 |
| WO | WO99/48599 | 9/1999 |
| WO | WO99/60397 | 11/1999 |
| WO | WO 00/21659 | 4/2000 |
| WO | WO 00/31528 | 6/2000 |
| WO | WO 00/51720 A3 | 9/2000 |
| WO | WO 01/09598 A1 | 2/2001 |
| WO | WO 01/38865 | 5/2001 |
| WO | WO 01/38865 A1 | 5/2001 |
| WO | WO 01/50123 A1 | 7/2001 |
| WO | WO 01/86283 A3 | 11/2001 |
| WO | WO 02/22250 A2 | 3/2002 |
| WO | WO 02/28509 | 4/2002 |
| WO | WO 02/28532 | 4/2002 |

OTHER PUBLICATIONS

Shediac, Renée et al., *Reversed-phase electrochromatography of amino acids and peptides using porous polymer monoliths*, "Journal of Chromatography A," 925 (2001) Elsevier Science B.V., pp. 251-263.

Guček, Marjan et al., *Separation of Sugar Anomers by Capillary Electrochromatography*, "Acta Chim. Slov.," 2000, 47, 165-177.

Tennikova, Dr. Tataina et al., *Short high-throughput monolithic layers for bioaffinity processing*, "LabPlus International," Feb./Mar. 2002.

MacNair, John E. et al., *Ultrahigh-Pressure Reversed-Phase Liquid Chromatography in Packed Capillary Columns*, "Analytical Chemistry," vol. 69, No. 6, Mar. 15, 1997, pp. 983-989.

Khandurina, Julia et al., *Microfabricated Porous Membrane Structure for Sample Concentration and Electrophoretic Analysis*, "Analytical Chemistry," vol. 71, No. 9, May 1, 1999, pp. 1815-1819.

Poole, Colin F., "4.5 Column Preparation," *The essence of chromatography*, 2003 Elsevier Science B.V., Amsterdam, the Netherlands, pp. 393-401.

Poole, Colin F., "5.6 Coupled-Column Systems," *The essence of chromatography*, 2003 Elsevier Science B.V., Amsterdam, The Netherlands, pp. 451-455.

Poole, Colin F., "8.4.2 Column Technology," *The essence of chromatography*, 2003 Elsevier Science B.V., Amsterdam, The Netherlands, pp. 664-668.

Krull, Ira S. et al., "2.3 Techniques for Packing Capillaries," *Capillary Electrochromatography and Pressurized Flow Capillary Electrochromatography*, 2000 HNB Publishing, New York, NY, pp. 40-46.

Tan, Aimin et al., *Chip-Based Solid-Phase Extraction Pretreatment for Direct Electrospray Mass Spectrometry Analysis Using and Array of Monolithic Columns in a Polymeric Substrate*, "Analytical Chemistry," vol. 75, No. 20, Oct. 15, 2003, pp. 5504-5511.

"Multi-Parallel-HPLC," Web document published at: http://www.sepiatec.com/download/phplc.pdf, SEPIAtec GmbH, Louis-Blériot-Strasse 5 D-12487 Berlin Germany.

Shediac, Renée, et al., *Reversed-phase electrochromatography of amino acids and peptides using porous polymer monoliths*, "Journal of Chromatography A," 925 (2001), pp. 251-263, Elsevier Science B.V.

MacNair, John E., et al., *Ultrahigh-Pressure Reversed-Phase Liquid Chromatography in Packed Capillary Columns*, "Analytical Chemistry," vol. 69, No. 6, Mar. 15, 1997, pp. 983-989.

MacNair, John E., et al., *Ultrahigh-Pressure Reversed-Phase Capillary Liquid Chromatography: Isocratic and Gradient Elution Using Columns Packed with 1.0-μm Particles*, "Analytical Chemistry," vol. 71, No. 3, Feb 1, 1999, pp. 700-708.

Ocvirk, Gregor, et al., *High Performance Liquid Chromatography Partially Integrated onto a Silicon Chip*, "Analytical Methods and Instrumentation," vol. 2, No. 2, 1995, pp. 74-82.

Shelly, Dennis C., et al., *Insights into the Slurry Packing and Bed Structure of Capillary Liquid Chromatographic Columns*, "Journal of Chromatography," 458, Elsevier Science Publishers B.V., Amsterdam, The Netherlands, (1989), pp. 267-279.

Poole, Colin F., et al., *Chromatography today*, 1991, Elsevier Science Publishers B.V., Amsterdam, The Netherlands.

Keller, H.P., et al., *Dynamic Slurry-Packing Technique for Liquid Chromatography Columns*, "Analytical Chemistry," vol. 49, No. 13, Nov. 1977, pp. 1958-1963.

Southan, Christopher, SmithKline Beechman Pharmaceuticals, "Fast, Sensitive, Flexible, and Cheap: How to Make Your Own High-Speed Microbore Columns," Sep. 21, 1996, The Association of Biomolecular Resource Facilities, www.abrf.org.

Applied Biosystems, "POROS® HP Glass Columns for Preparative Chromatography," Aug. 2001.

Guček, Marjan, et al., *Separation of Sugar Anomers by Capillary Electrochromatography*, "Acta Chim. Slov.," Mar. 2, 2000, 47, 165-177.

Palm, Anders, et al., "Integrated Sample Preparation and MALDI MS on a disc," *Micro Total Analysis Systems*, J.M. Ramsey and A. van den Berg (eds.), 2001 Kluwer Academic Publishers, The Netherlands, pp. 216-218.

Zhang, Bailin, et al., *High-Throughput Microfabricated CE/ESI-MS: Automated Sampling from a Microwell Plate*, "Analytical Chemistry," vol. 73, No. 11, Jun. 1, 2001, pp. 2675-2681.

Manz, Andreas, et al., "Planar Chips Technology for Miniaturization of Separation Systems: A Developing Perspective in Chemical Monitoring," *Advances in Chromatography*, vol. 33, 1993 Dekker, Inc., New York/Basel/Hong Kong, pp. 1-66.

Manz, Andreas, et al., *Miniaturization f Separation Techniques Using Planar Chip Technology*, "Journal of High Resolution Chromatography," vol. 16, Jul. 1993, pp. 433-436.

Huber, Christian G., et al., *High-resolution liquid chromatography of DNA fragments on non-porous poly(styrene-divinylbenzene) particles*, "Nucleic Acids Research," 1993, vol. 21, No. 5, pp. 1061-1066.

Finot, Michael, et al., "High Throughput Pharmaceutical Formulation Evaluation and Analysis using Capillary Electrochromatography on a Microfluidic Chip," *Micro Total Analysis Systems*, J.M. Ramsey and A. van den Berg (eds.), 2001 Kluwer Academic Publishers, The Netherlands, pp. 480-482.

Jemere, Abedaw B., et al., "Microchip-Based Selective Preconcentration using Protein A Immunoaffinity Chromatography," *Micro Total Analysis Systems*, J.M. Ramsey and A. van den Berg (eds.), 2001 Kluwer Academic Publishers, The Netherlands, pp. 501-502.

Morishima, Keisuke, et al., "In-Situ Preparation of Photopolymerized Sol-Gel Monoliths for Capillary Electrochromatography on a Chip," *Micro Total Analysis Systems*, J.M. Ramsey and A. van den Berg (eds.), 2001 Kluwer Academic Publishers, The Netherlands, pp. 557-558.

Seki, Minoru, et al., "Chromatographic Separation of Proteins on a PDMS-Polymer Chip by Pressure Flow," *Micro Total Analysis Systems*, J.M. Ramsey and A. van den Berg (eds.), 2001 Kluwer Academic Publishers, The Netherlands, pp. 48-50.

Sato, Kiichi, et al., "Integrated Immunoassay System using Multichannel Microchip for Simultaneous Determination," *Micro Total Analysis Systems*, J.M. Ramsey and A. van Berg (eds.), 2001 Kluwer Academic Publichers, The Netherlands, pp. 511-512.

Coates, Don M., et al., *Modification of Polymeric Material Surfaces with Plasmas*, Plasma processing of Advanced Materials, George A. Collins and Donald J. Rej, eds., MRS Bulletin, Aug. 1996, Chapter IV.

Ngola, Sarah M., et al., *Conduct-as-Cast Polymer Monoliths as Separation Media for Capillary Electrochromatography*, "Analytical Chemistry," vol. 73, No. 5, Mar. 1, 2001, pp. 849-856.

Singh, Anup K., et al., "Rapid Separation of Peptides and Amino Acids in Glass Microchips by Reversed-Phase Electrochromatography," *Micro Total Analysis Systems*, J.M. Ramsey and A. van den Berg (eds.), 2001 Kluwer Academic Publishers, The Netherlands, pp. 649-651.

Throckmorton, Daniel J., et al., *Elecrochromatography in Microchips: Reversed-Phase Separation of Peptides and Amino Acids using Photopatterned Rigid Polymer Monoliths*, "Analytical Chemistry," vol. 74, No. 4, Feb. 15, 2003, pp. 784-789.

Ericson, Christer, et al., *Electroosmosis- and Pressure-Driven Chromatography in Chips using Continuous Beds*, "Analytical Chemistry," vol. 72, No. 1, Jan. 1, 2000, pp. 81-87.

"Multi-Parallel-HPLC," Web document published at: http://www.sepiatec.com/download/phplc.pdf. SEPIAtec GmbH, Louis-Blériot-Strasse 5 D-12487 Berlin Germany, undated.

* cited by examiner

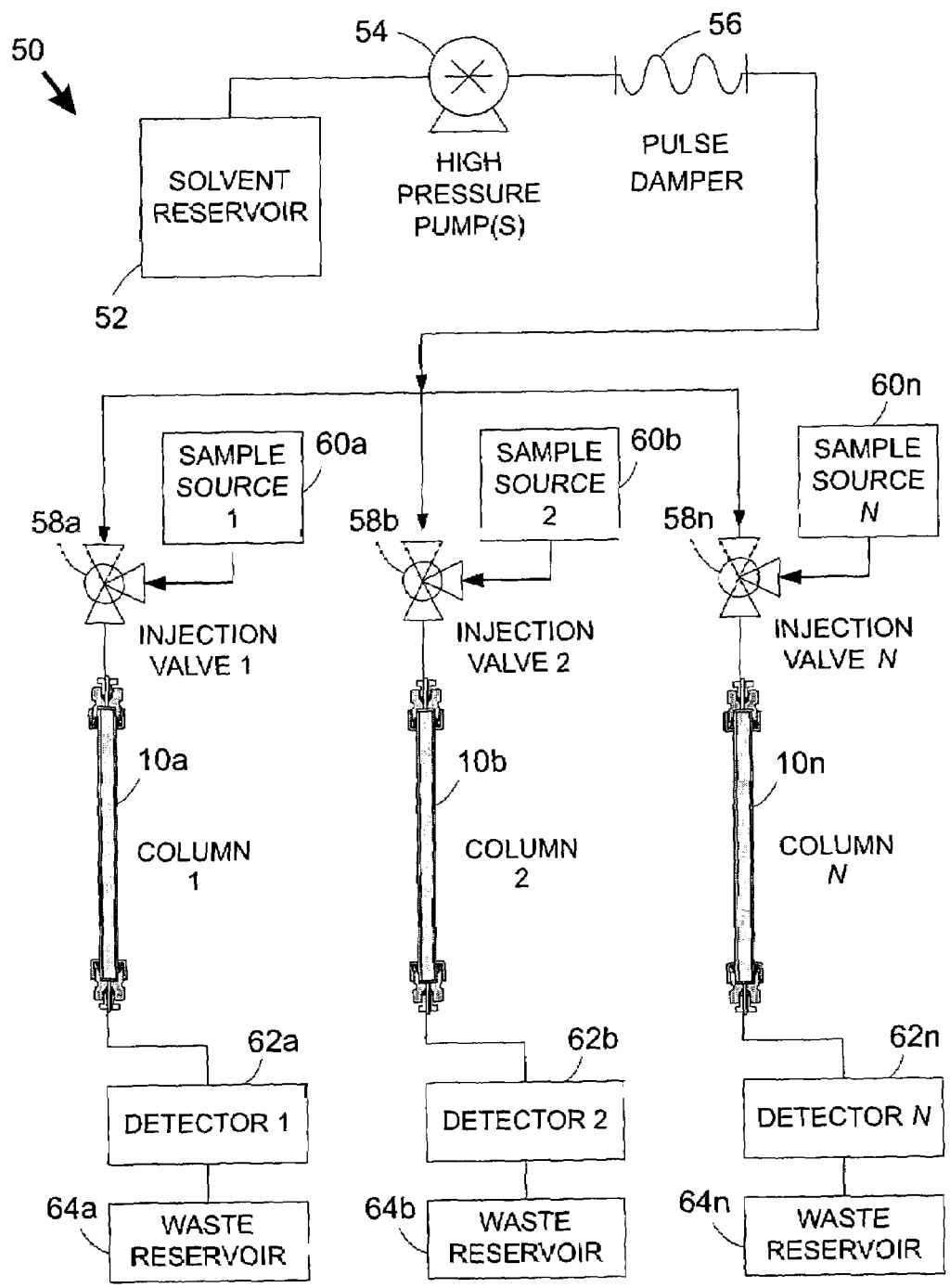
FIG. _3 (PRIOR ART)

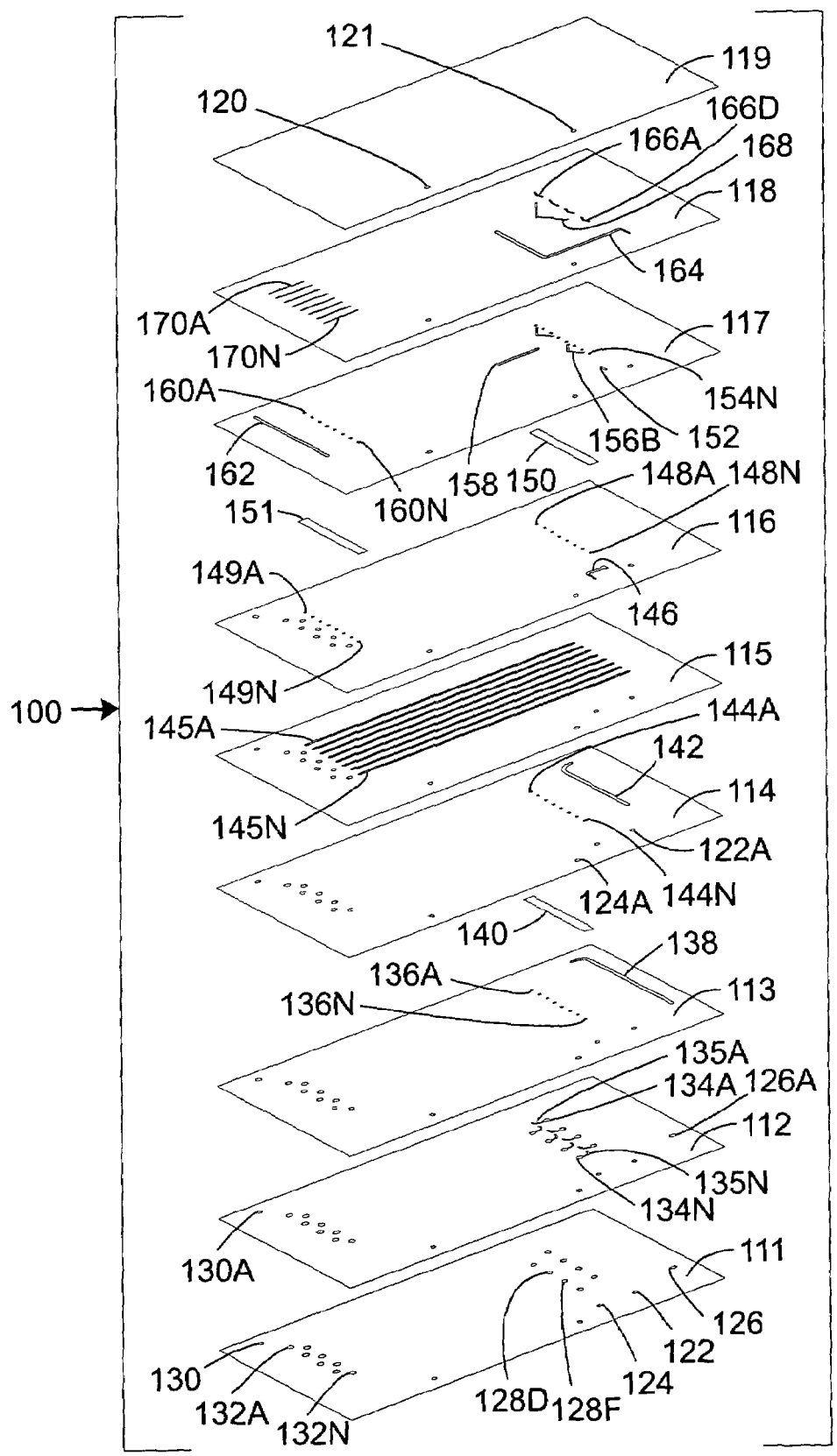
FIG._4A

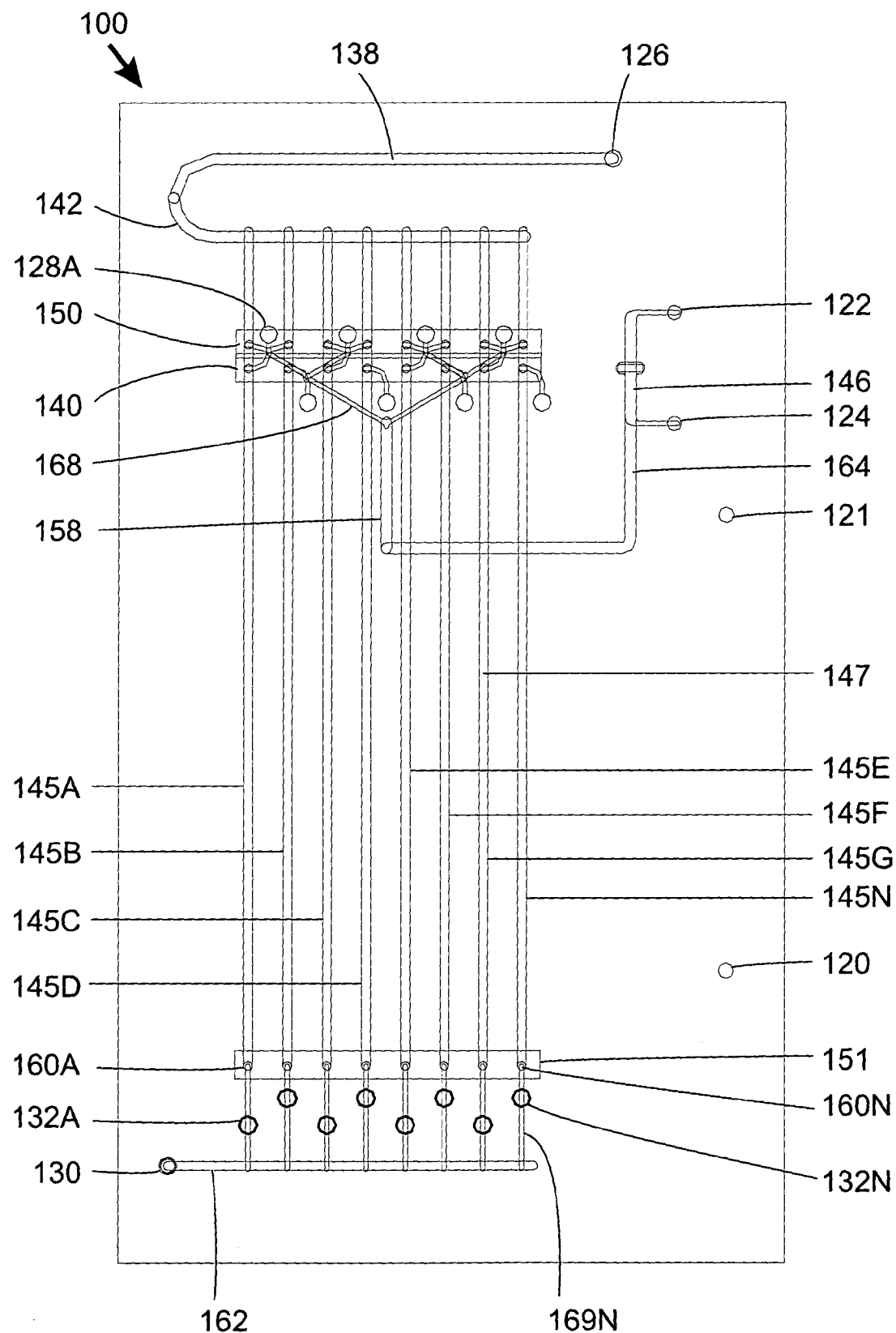
FIG._4B

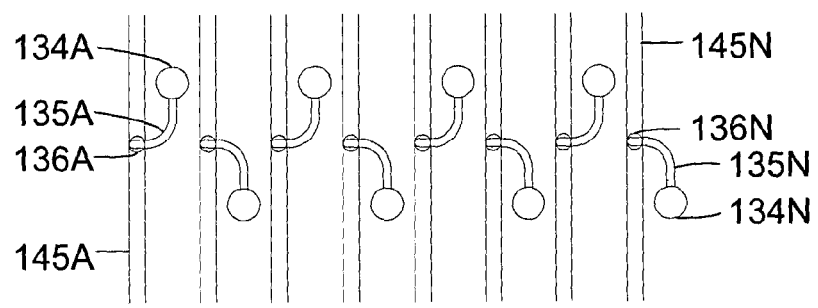
FIG._4C
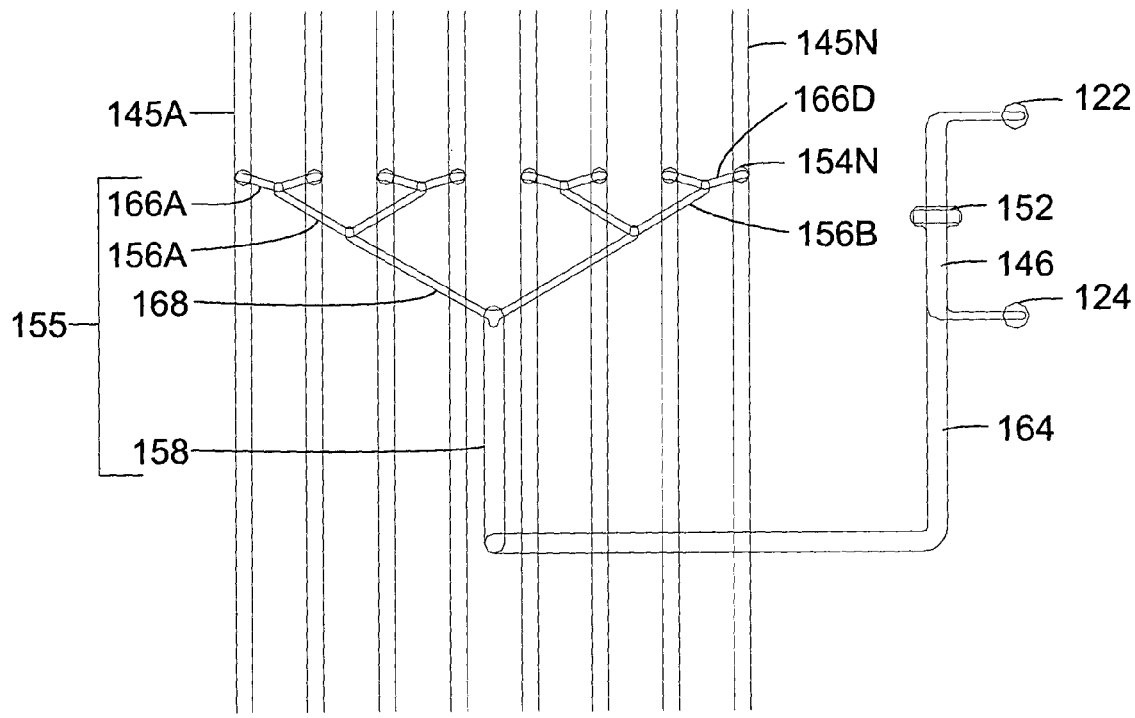
FIG._4D

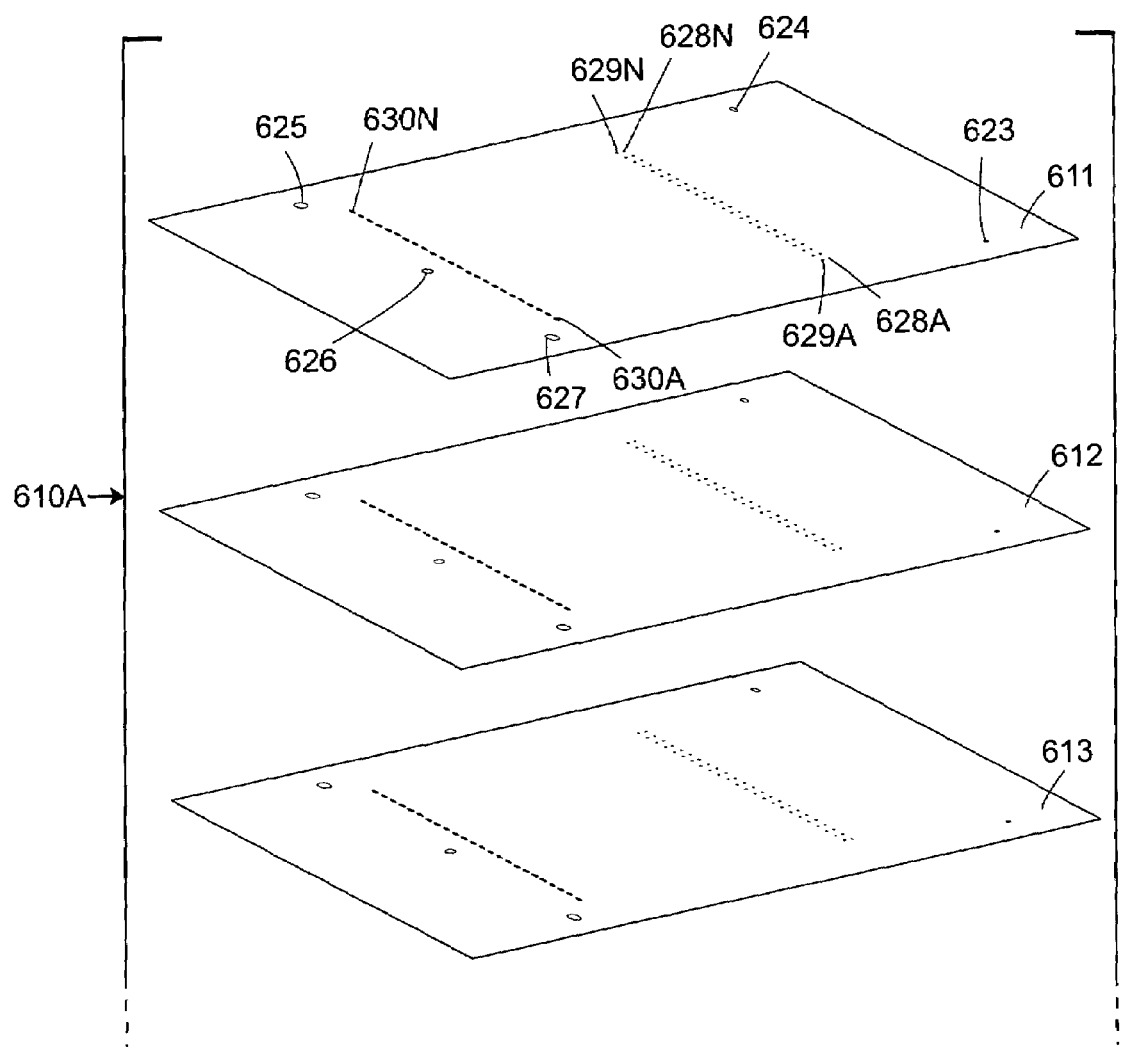
FIG._6A

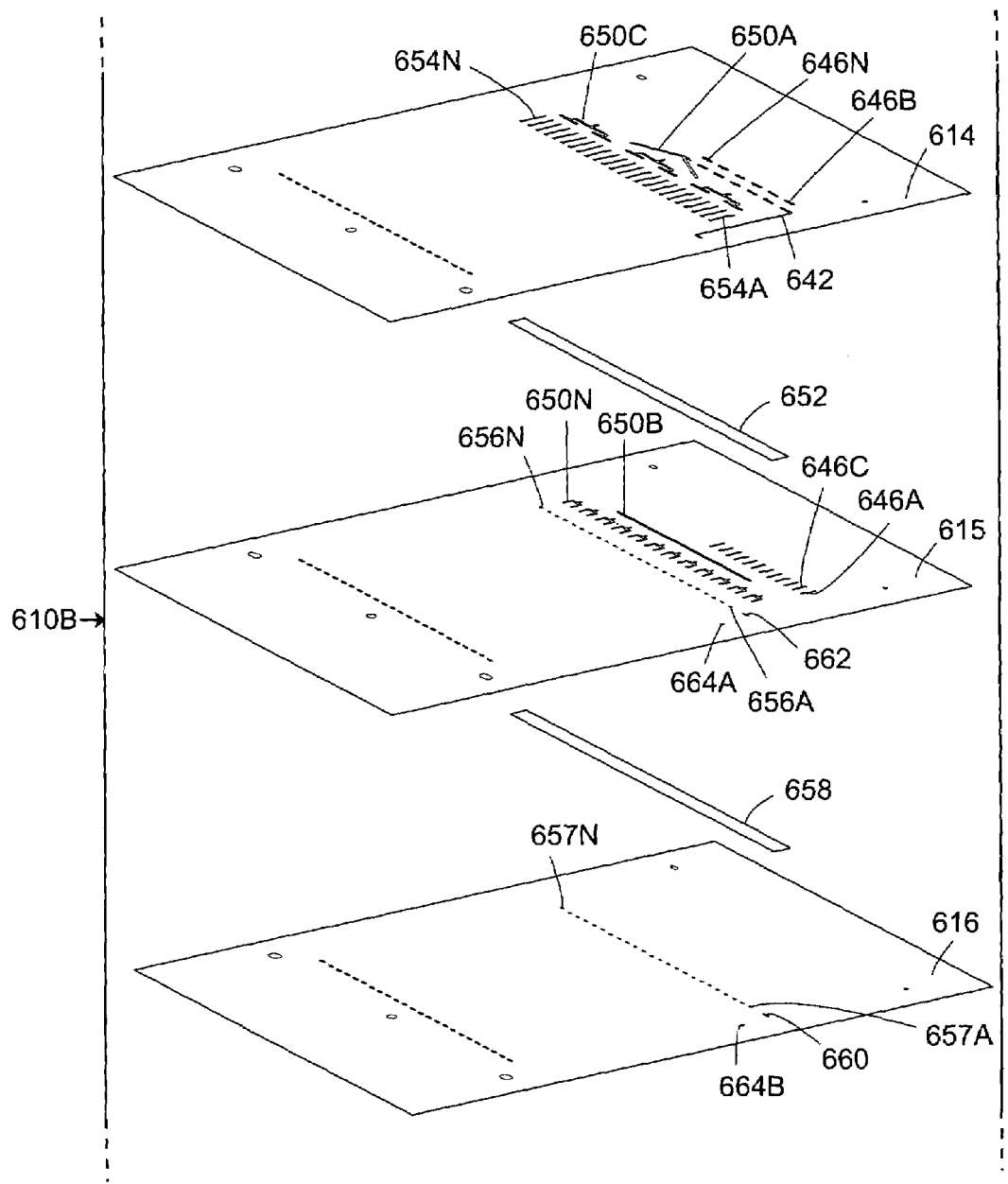
FIG._6B

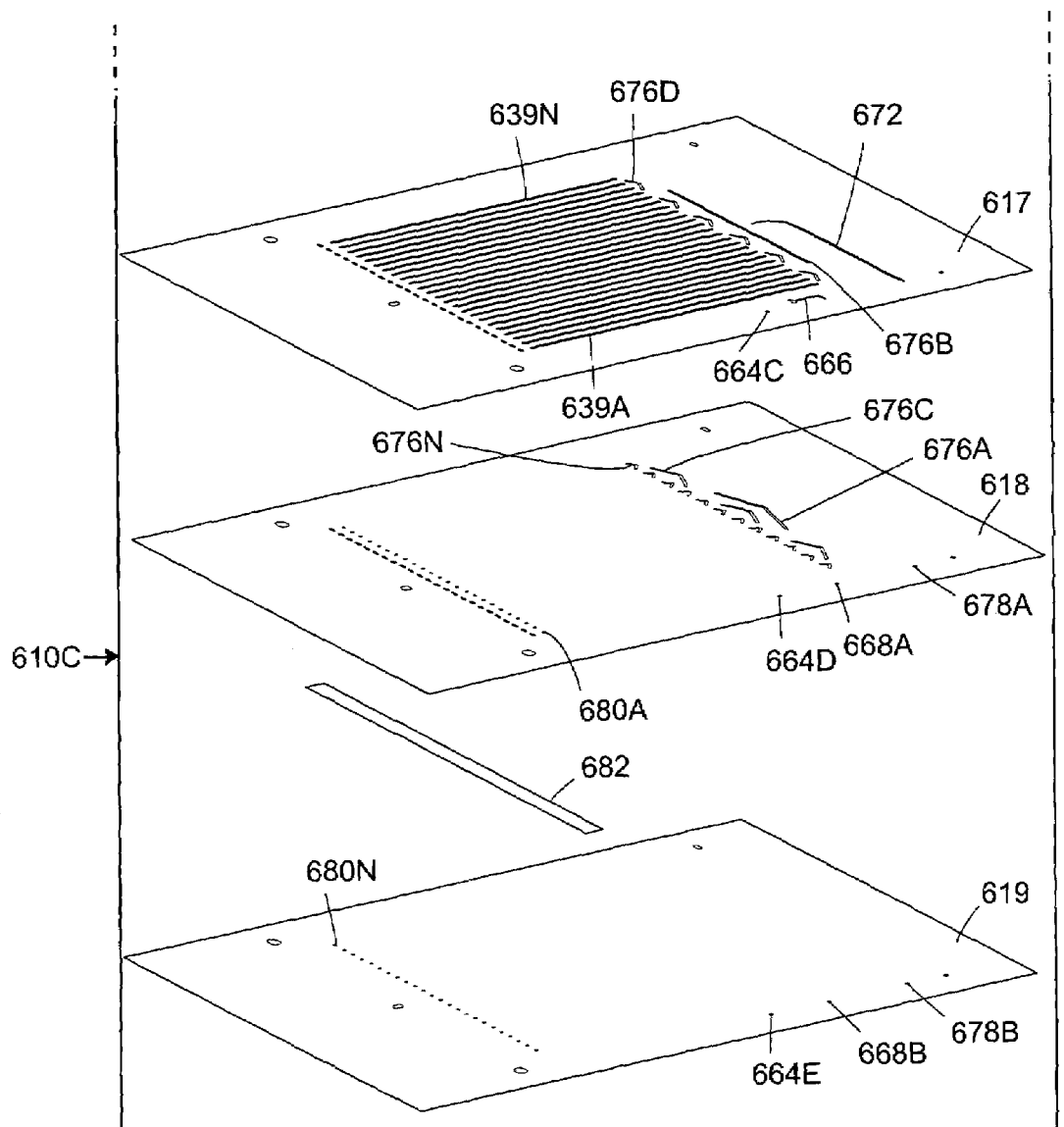
FIG._6C

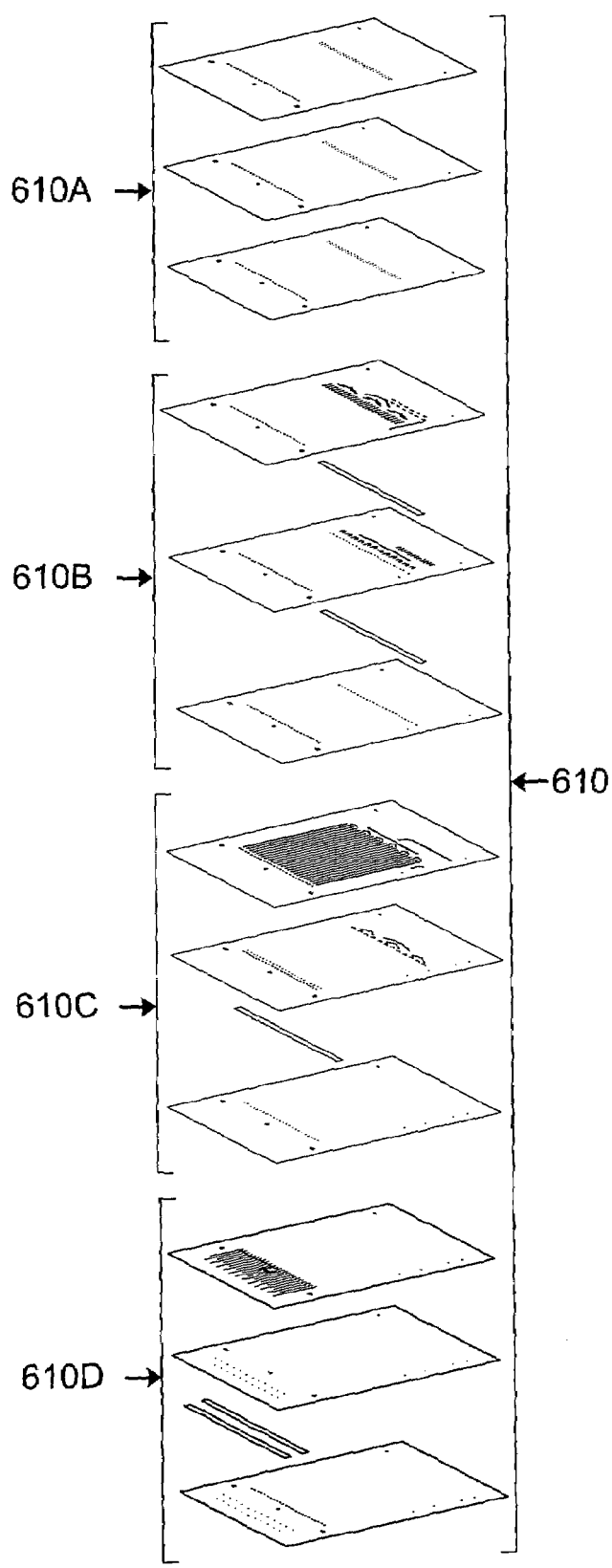
FIG._6E

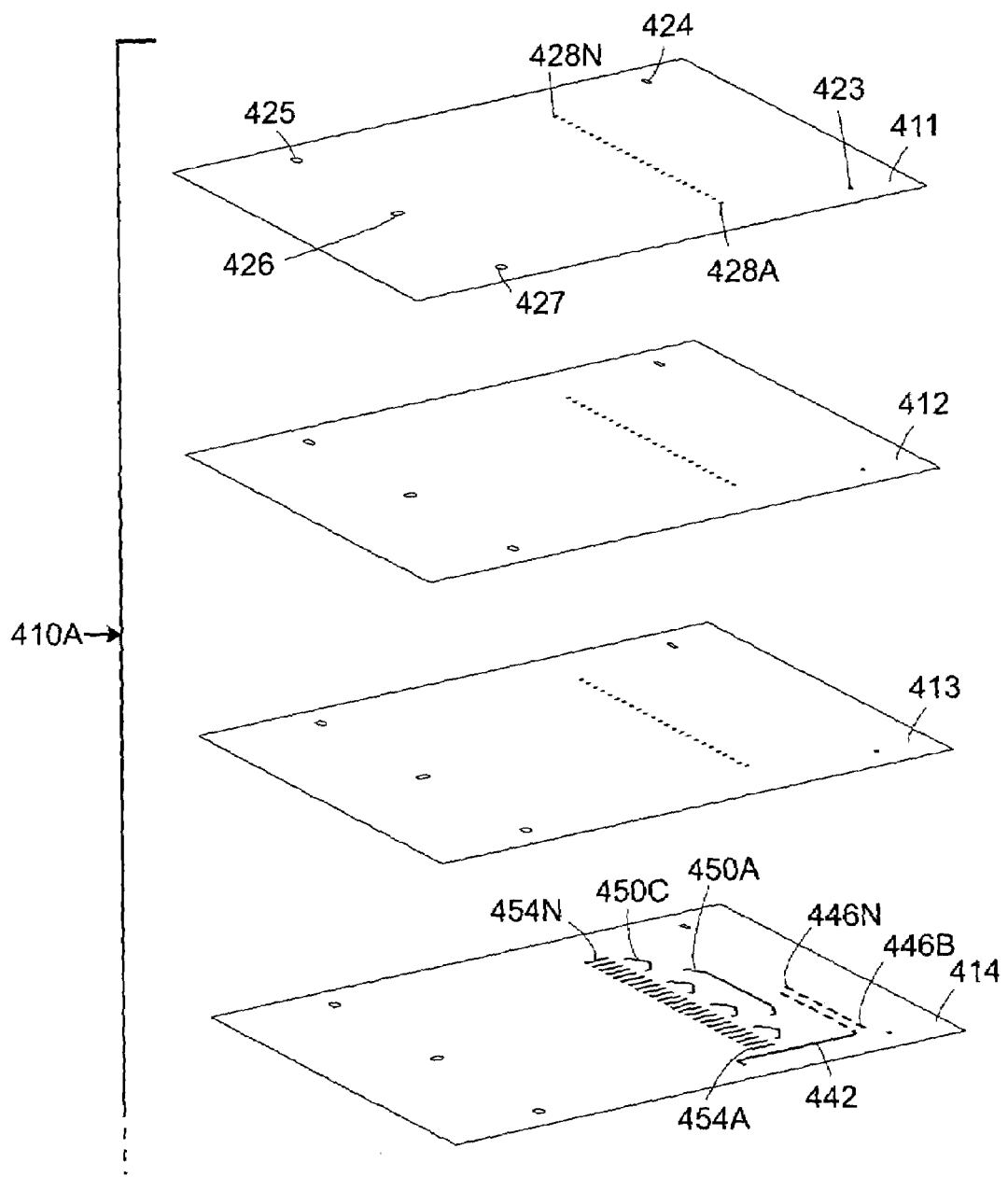
FIG._8A

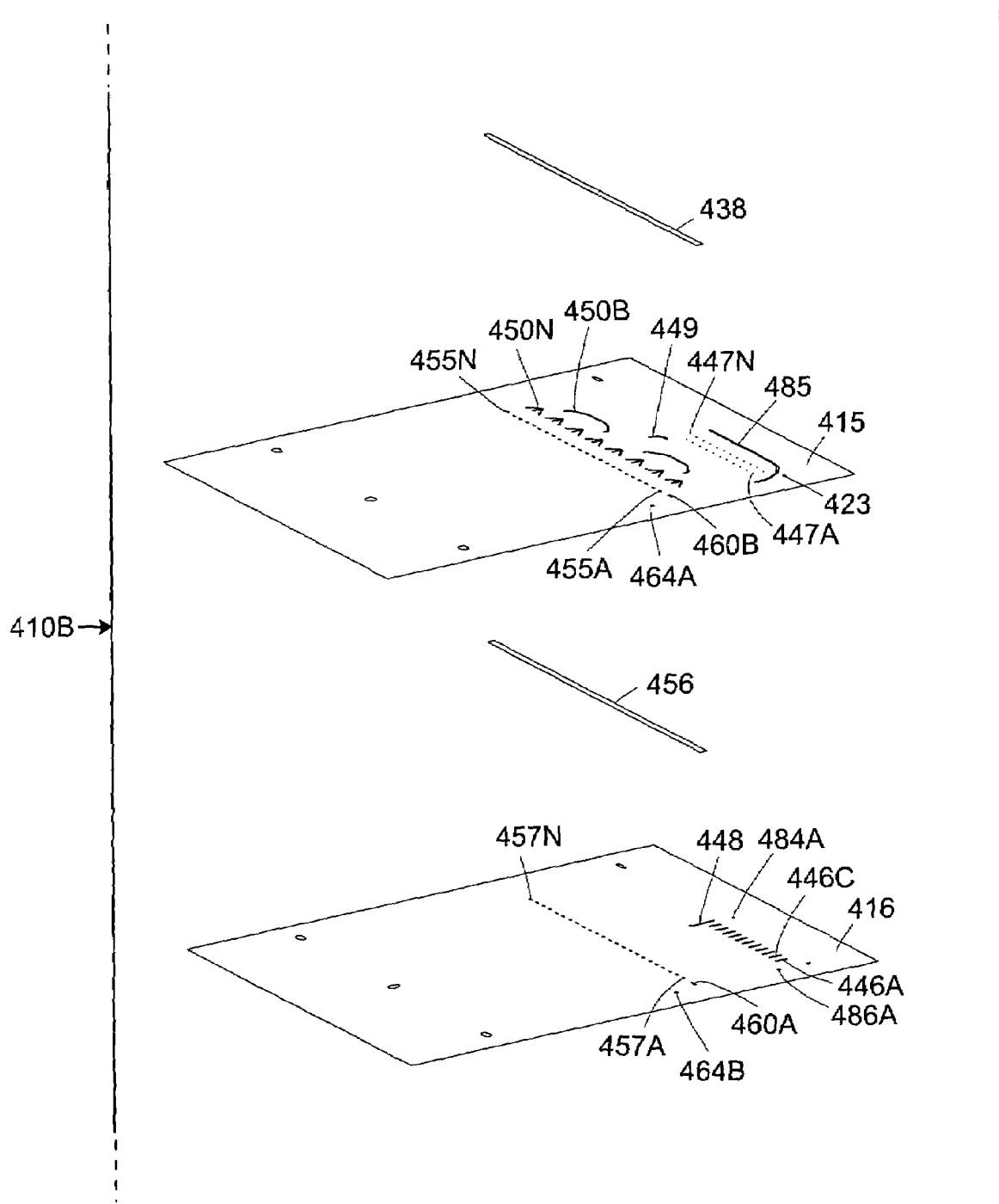
FIG._8B

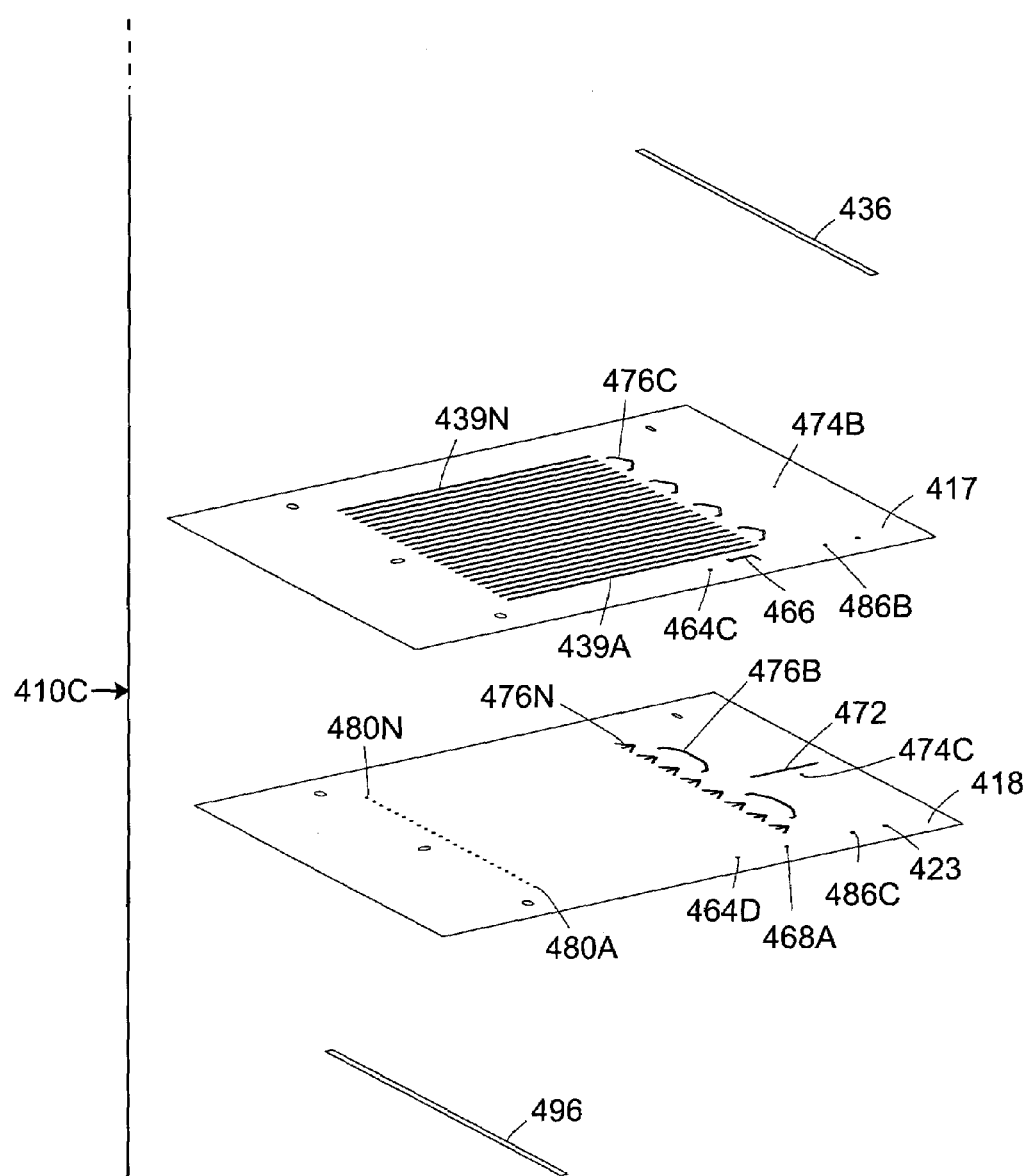
FIG._8C

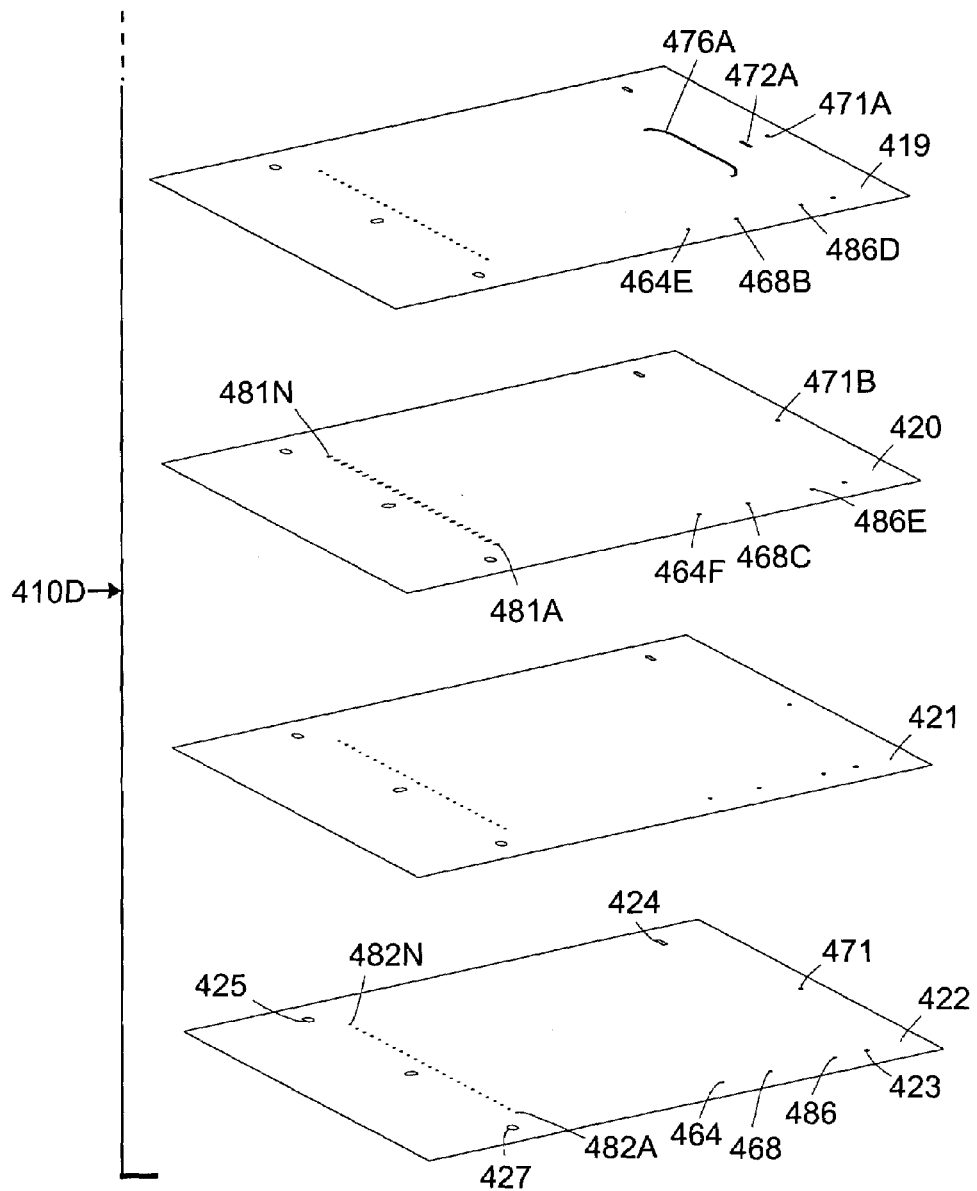
FIG._8D

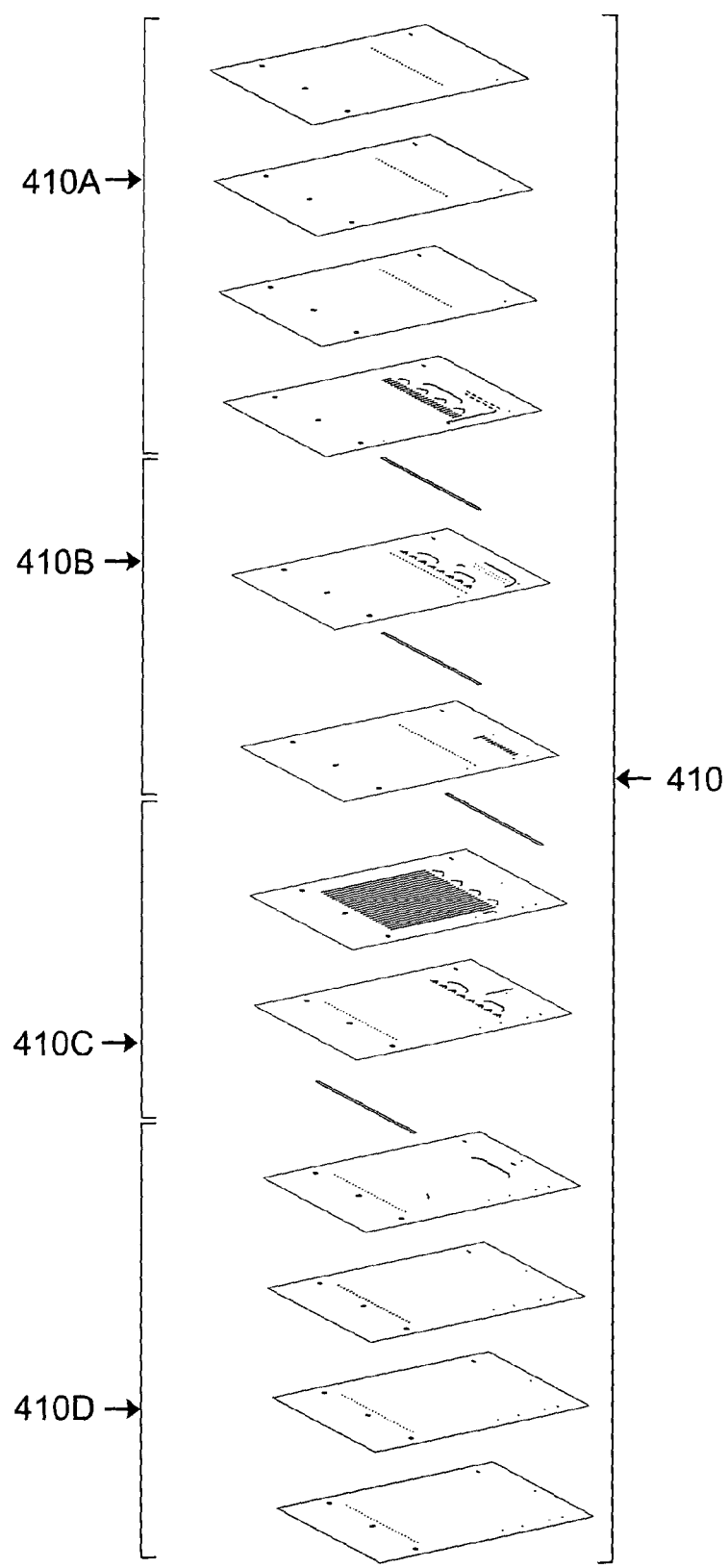
FIG._8E

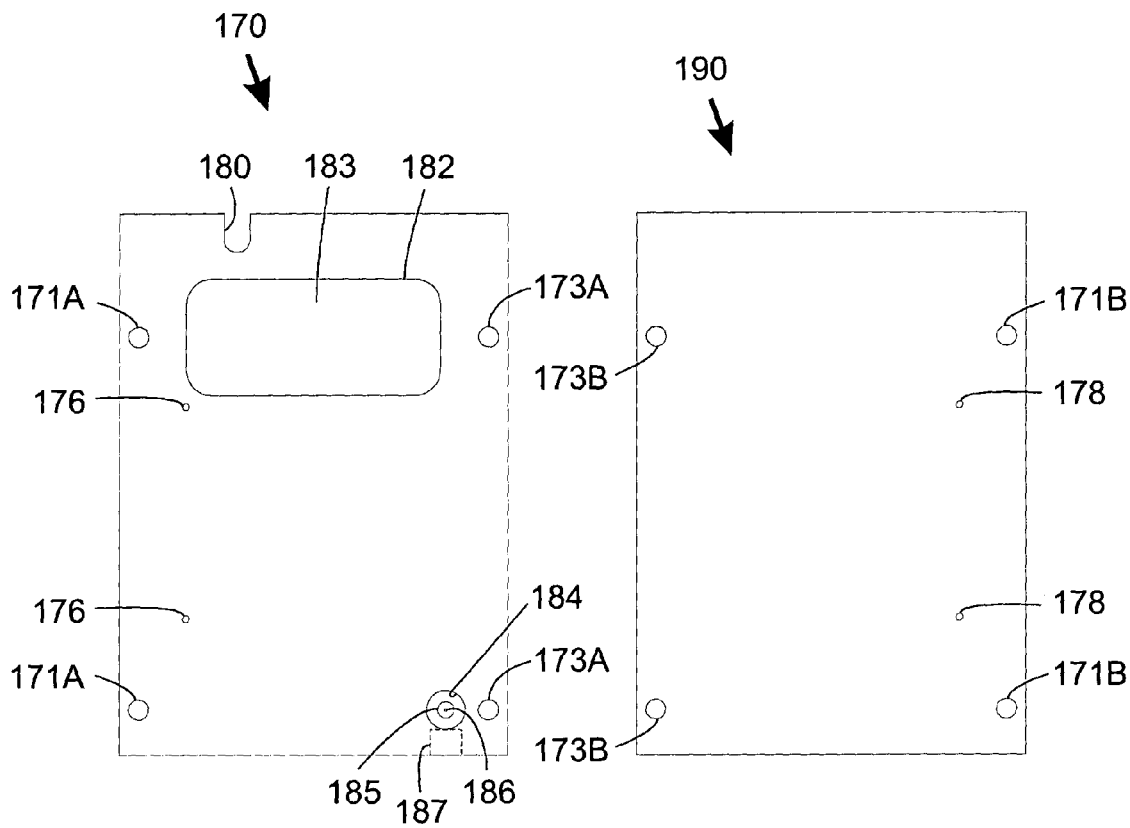
FIG._9A  FIG._9B
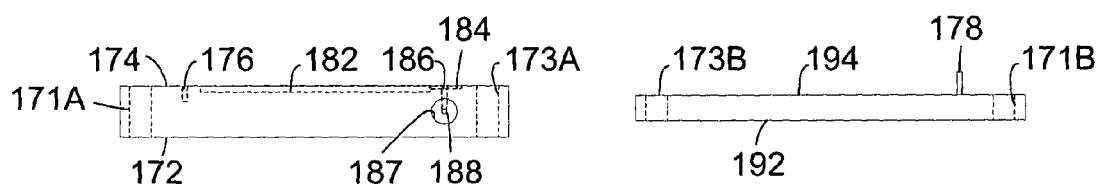
FIG._9C  FIG._9D

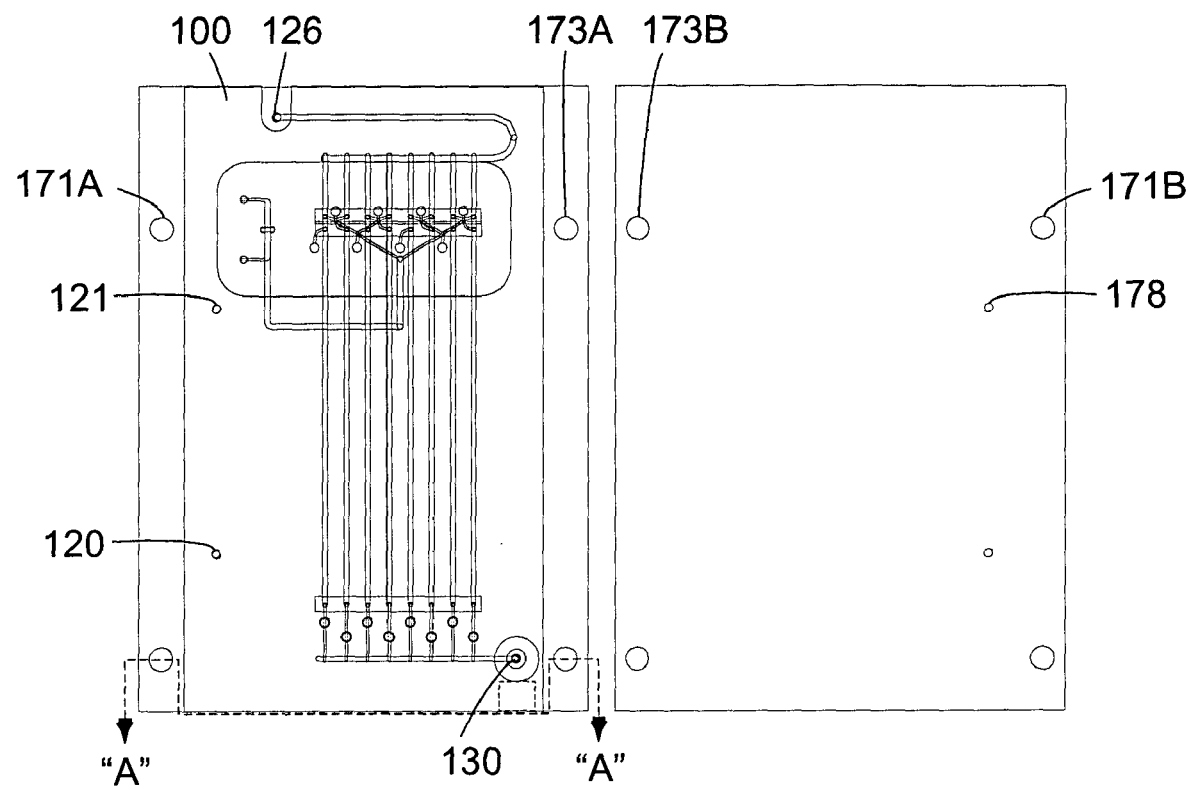
FIG. _9E
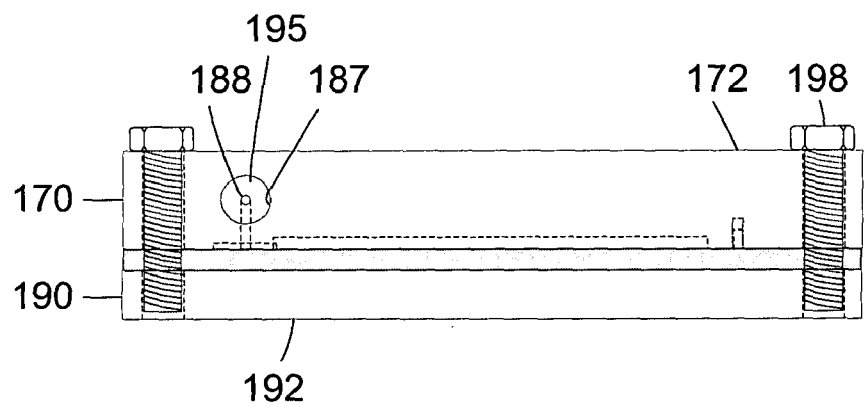
FIG. _9F

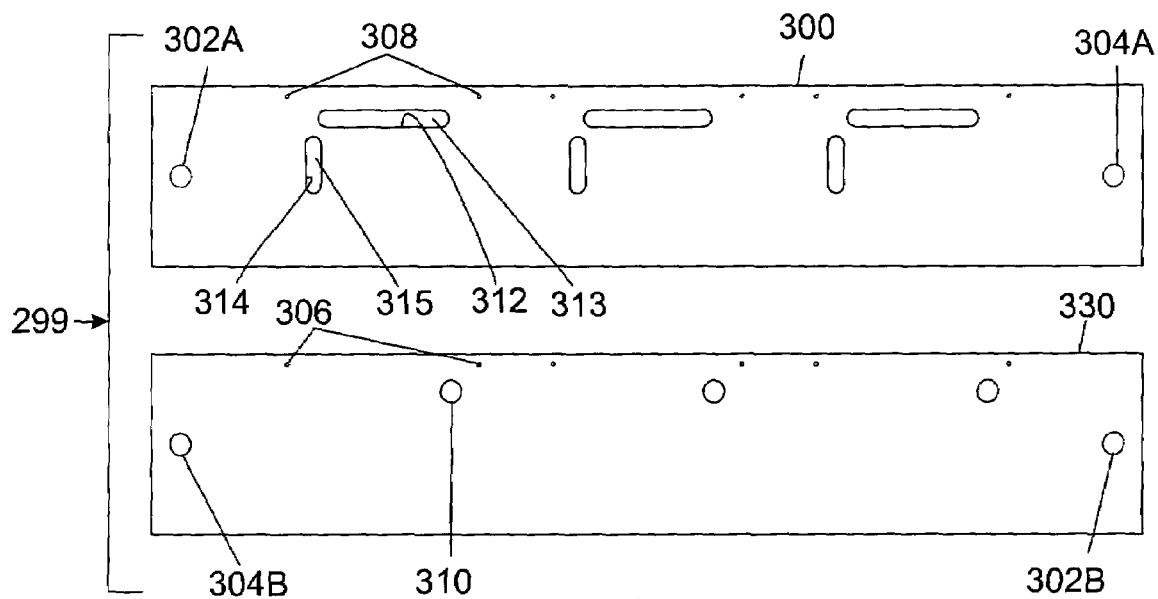
FIG._10B
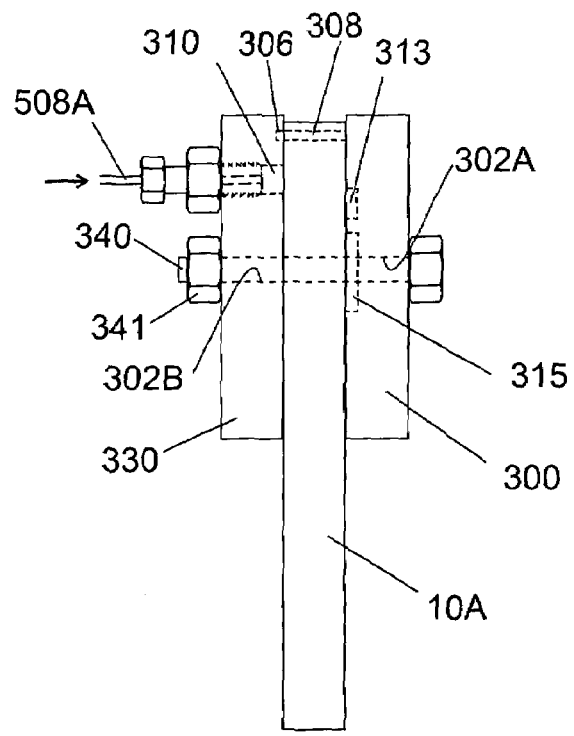
FIG._10A

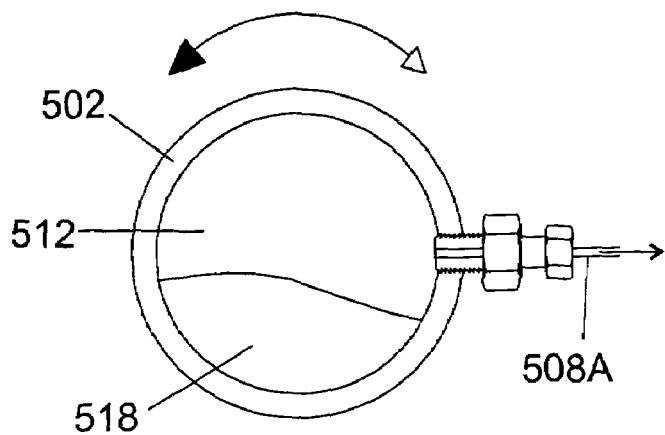
FIG._12C
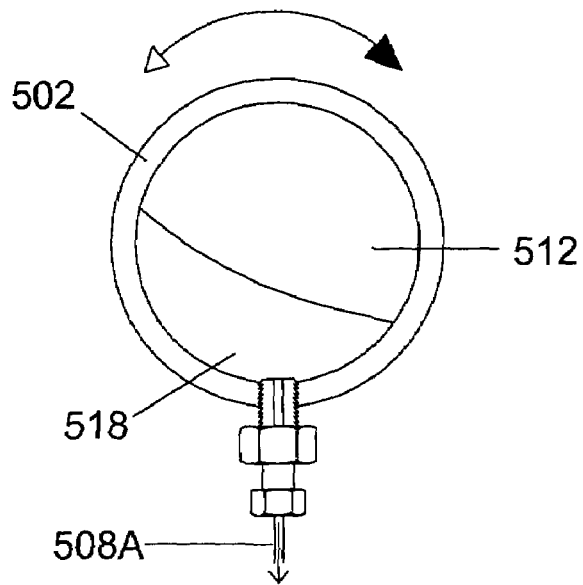
FIG._12B

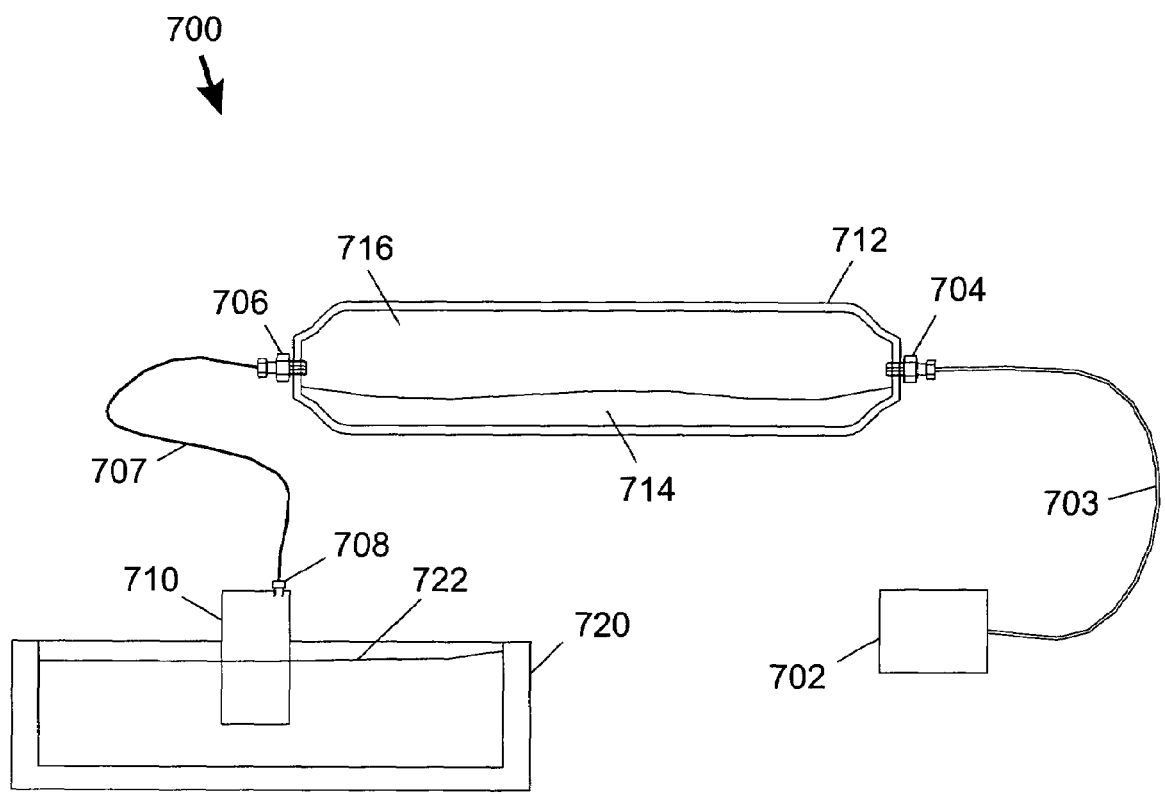
FIG._13

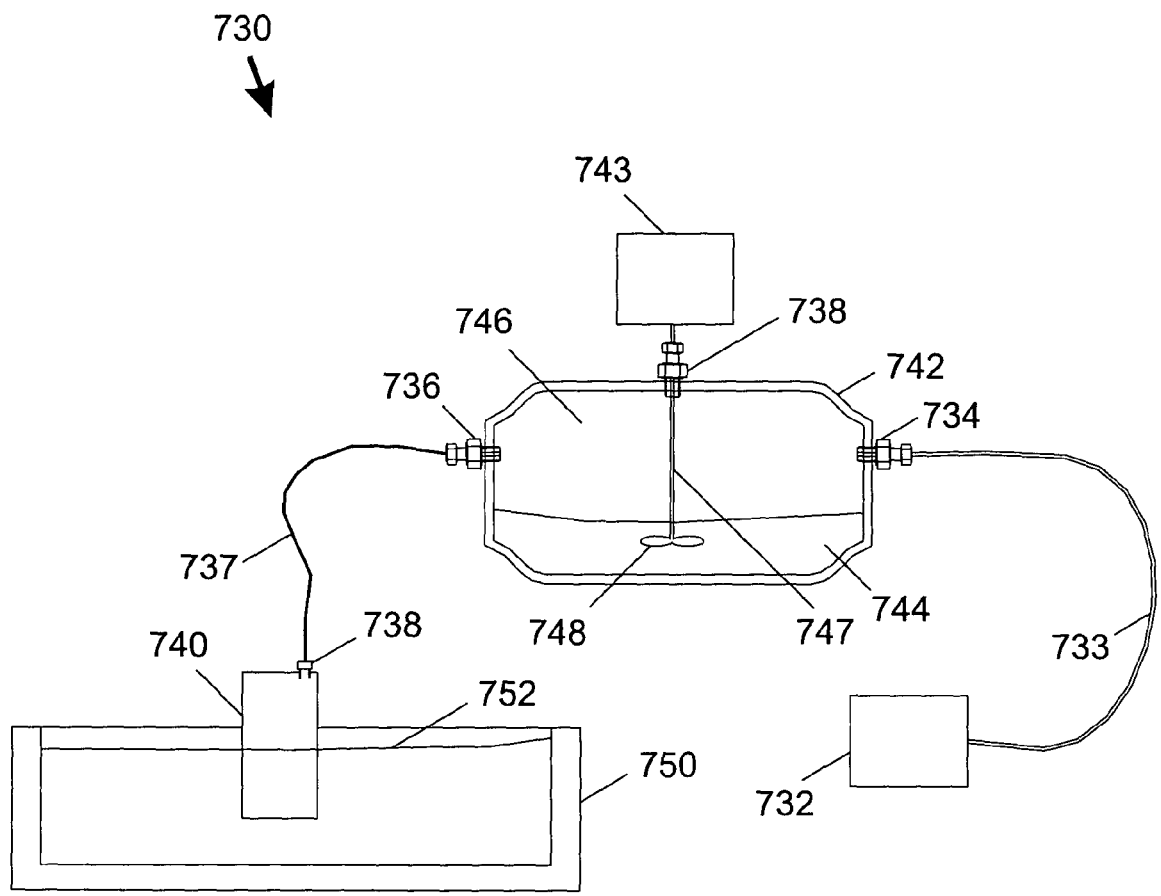
FIG._14

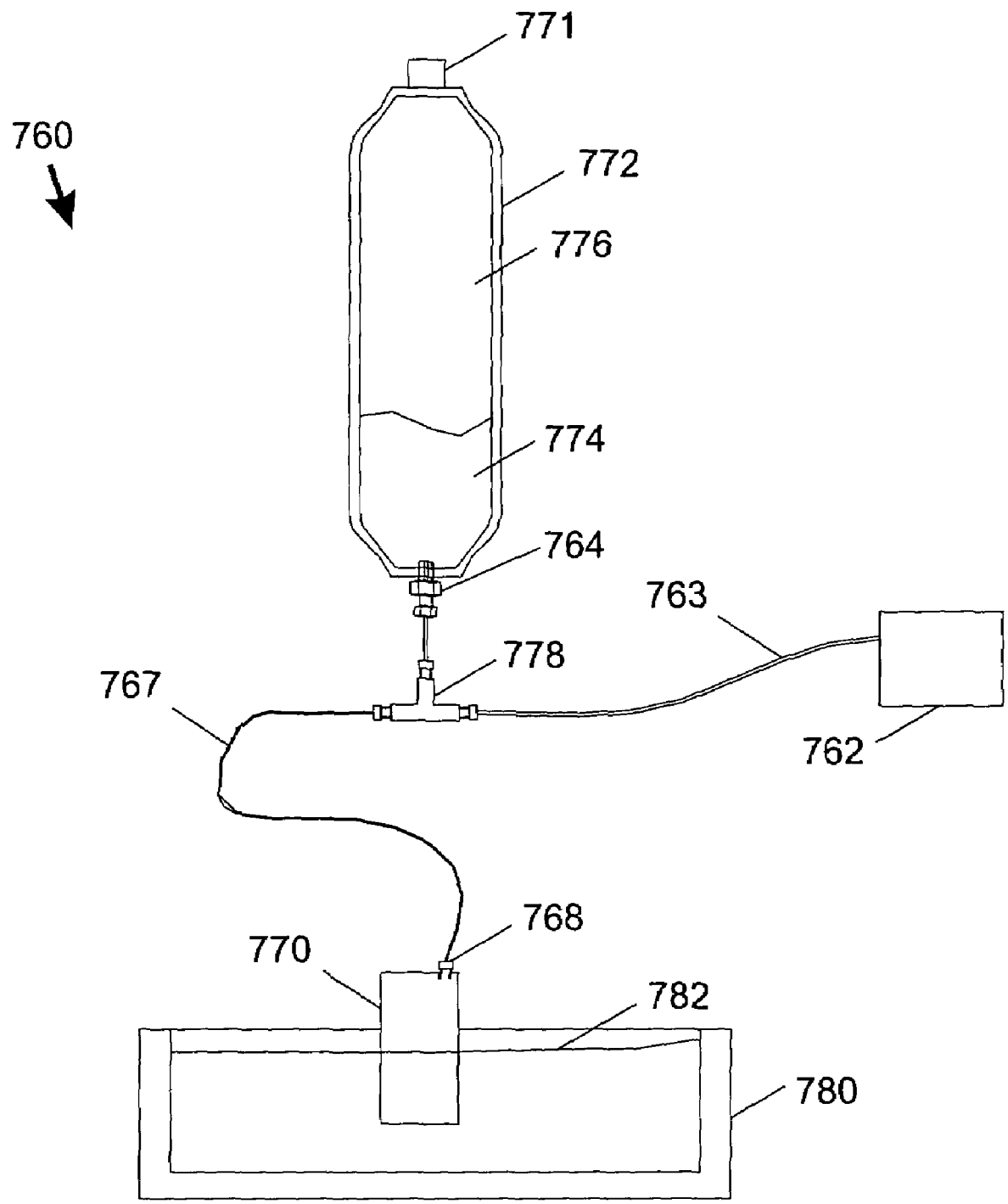
FIG._15

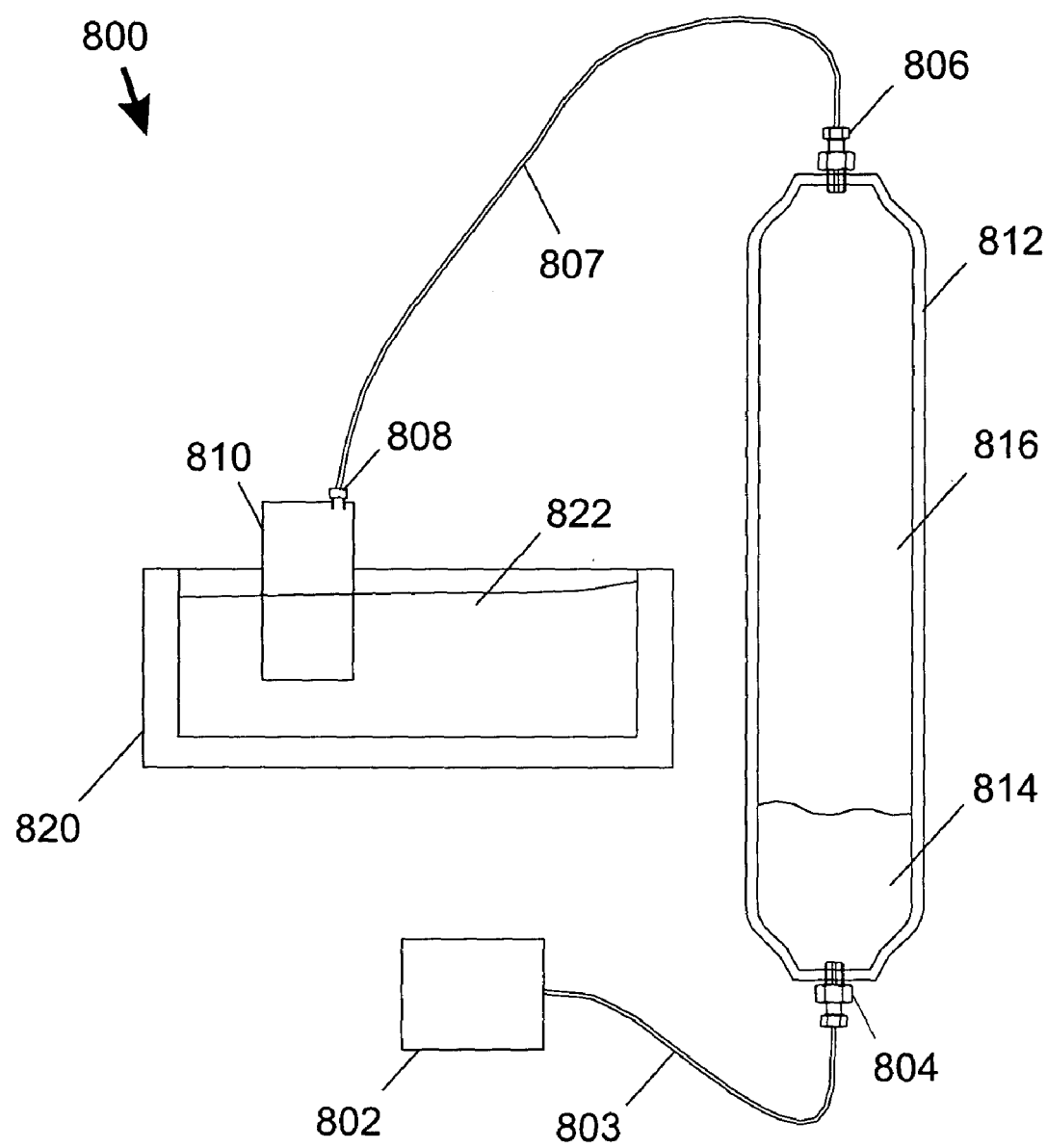
FIG._16

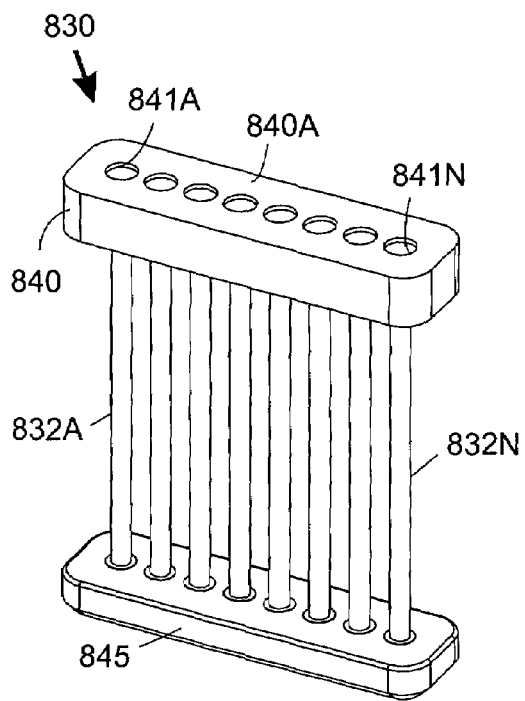
FIG._17A
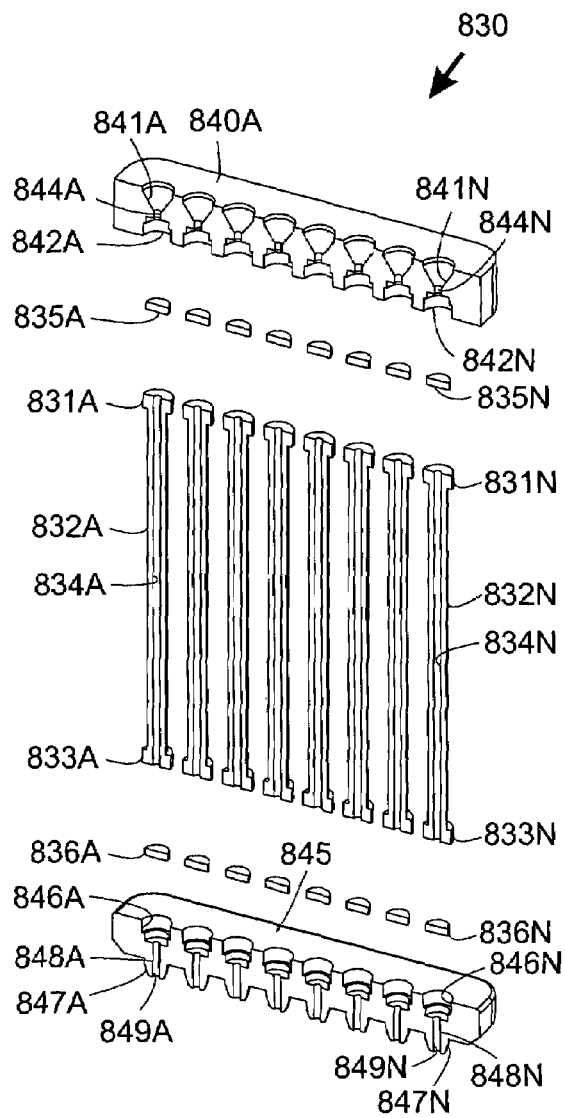
FIG._17C
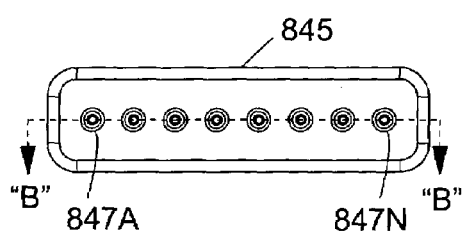
FIG._17B

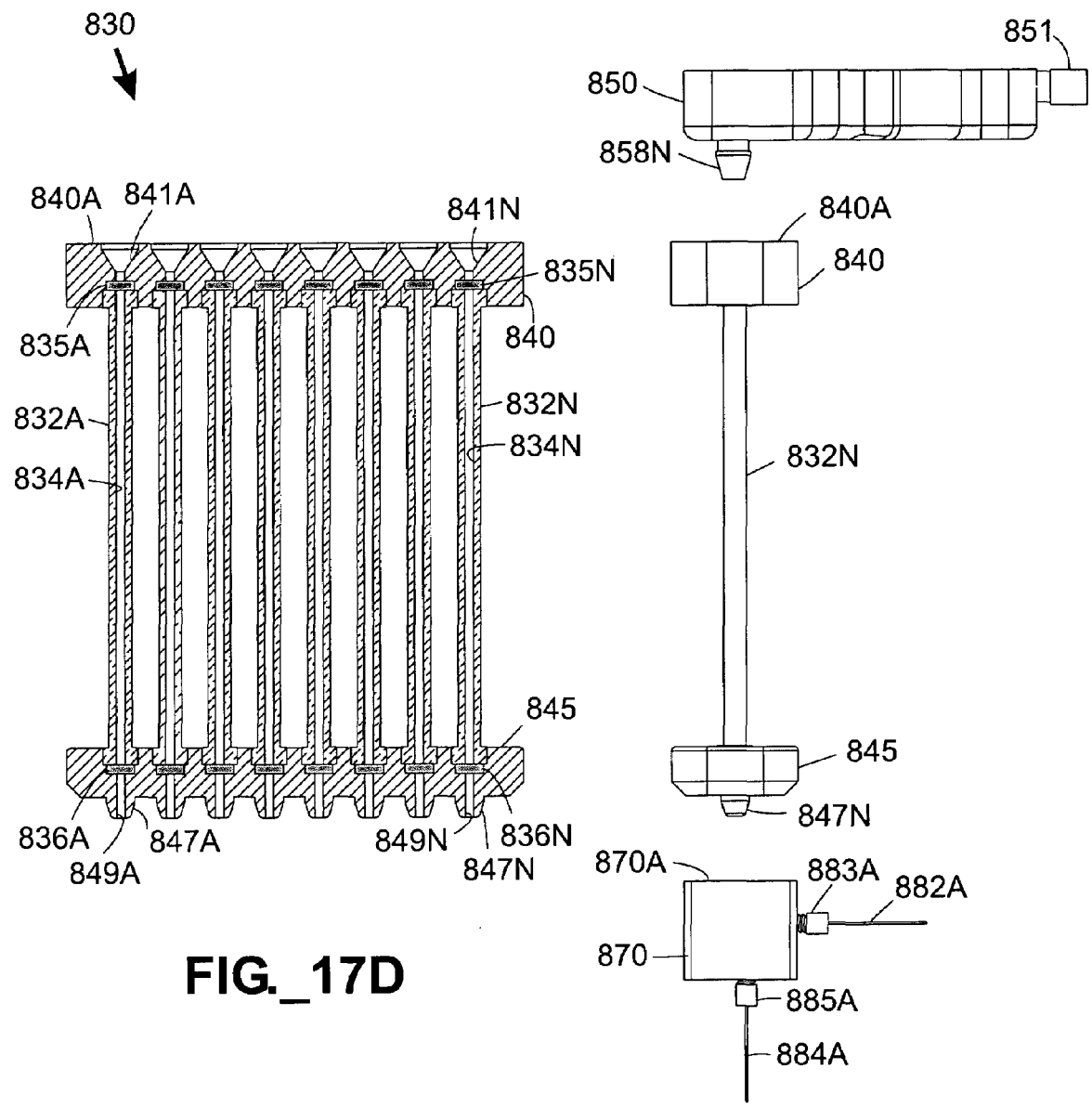
FIG._17D
FIG._18A

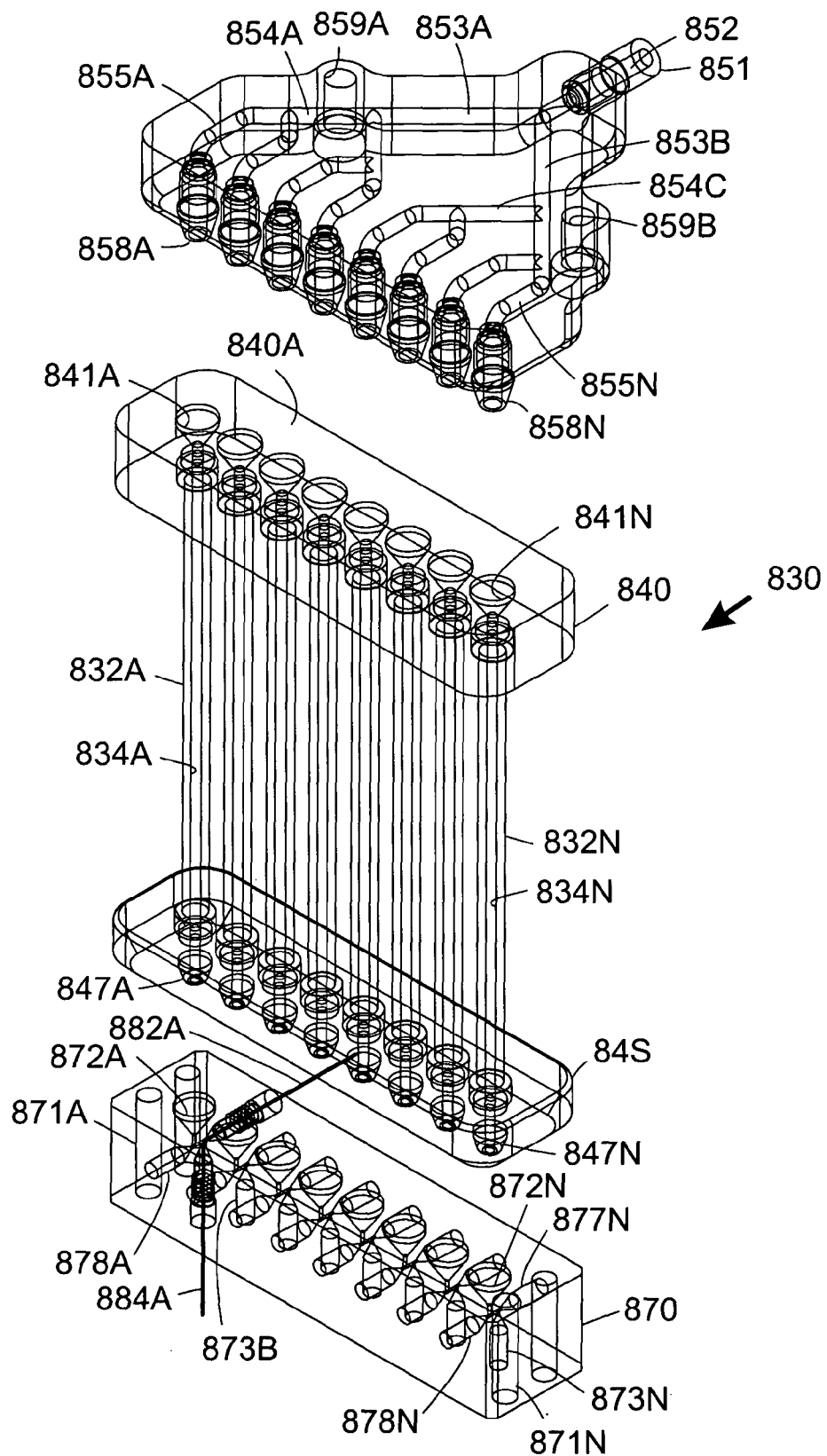
FIG._18B

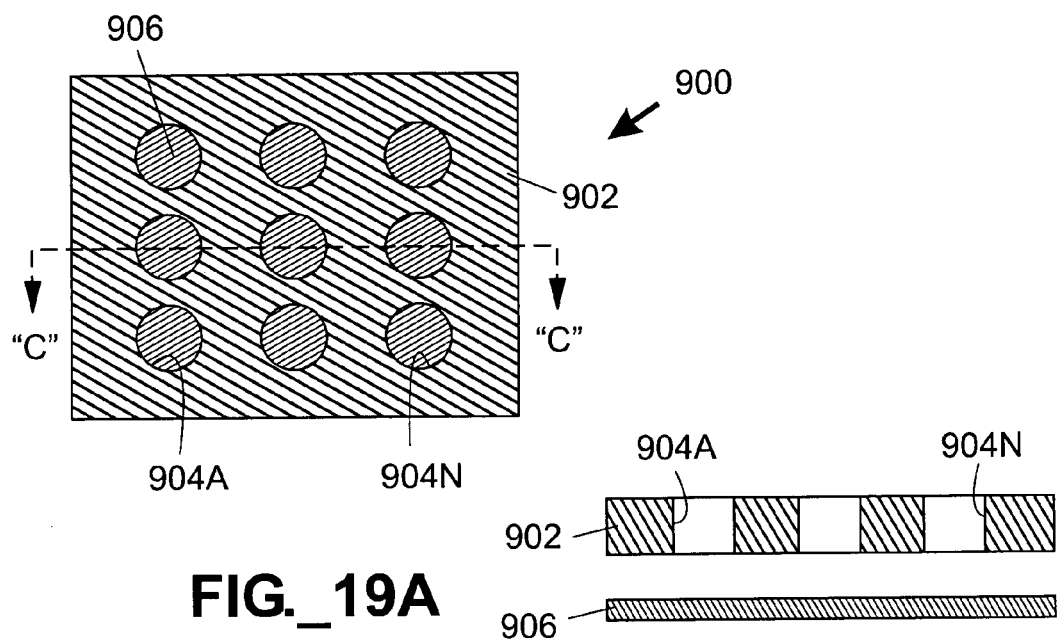
FIG._19A
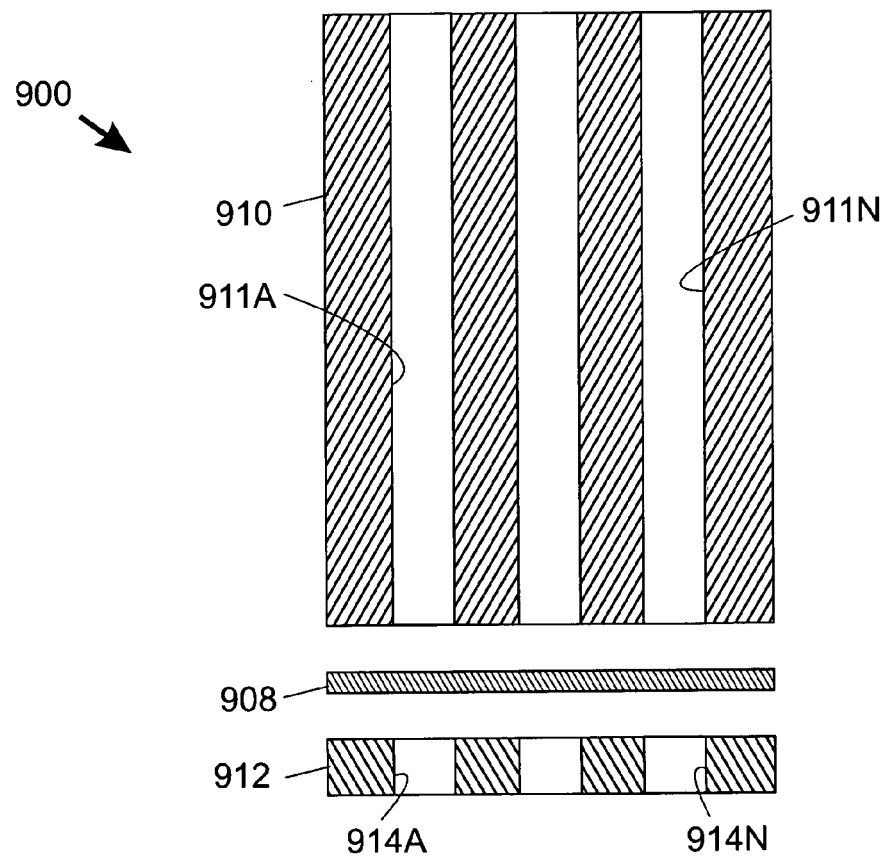
FIG._19B

MULTI-COLUMN SEPARATION DEVICES AND METHODS

STATEMENT OF RELATED APPLICATIONS

This application cont-in-part and claims benefit of commonly assigned U.S. application Ser. No. 10/366,985 filed Feb. 13, 2003, now U.S. Pat. No. 6,923,907 which claims benefit of both U.S. Application Ser. No. 60/415,896 filed Oct. 3, 2002 and U.S. Application Ser. No. 60/357,683 filed Feb. 13, 2002.

FIELD OF THE INVENTION

The present invention relates to separation columns such as may be used for separating samples containing various chemical or biological species.

BACKGROUND OF THE INVENTION

Chemical and biological separations are routinely performed in various industrial and academic settings. For example, recent developments in the pharmaceutical industry and in combinatorial chemistry have exponentially increased the number of potentially useful compounds, each of which must be characterized in order to identify their active components and/or establish processes for their synthesis. To more quickly analyze these compounds, researchers have sought to automate analytical processes and to implement analytical processes in parallel.

One useful analytical process is chromatography, which encompasses a number of methods that are used for separating ions or molecules that are dissolved in or otherwise mixed into a solvent. In fact, chromatography has many applications including separation, identification, purification, and quantification of compounds within various mixtures.

Liquid chromatography is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a liquid-permeable medium such as packed granules (particulate material) disposed within a tube (or other channel boundary). The packed material contained by the tube or similar boundary is commonly referred to as a "separation column." High pressure is often used to obtain a close-packed column with a minimal void between each particle, since better resolution during use is typically obtained from more tightly packed columns. As an alternative to packed particulate material, a porous monolith may be used.

Typical interactions between stationary phases and solutes include adsorption, ion-exchange, partitioning, and size exclusion. Typical types of stationary phases to support such interactions are solids, ionic groups on a resin, liquids on an inert solid support, and porous or semi-porous inert particles, respectively. Commonly employed base materials include silica, alumina, zirconium, or polymeric materials. A stationary phase material may act as a sieve to perform simple size exclusion chromatography, or the stationary phase may include functional groups (e.g., chemical groups) to perform other (e.g., adsorption or ion exchange separation) techniques.

Mobile phase is forced through the stationary phase using means such as, for example, one or more pumps, gravity, voltage-driven electrokinetic flow, or other established means for generating a pressure differential. After sample is injected into the mobile phase, such as with a conventional loop valve, components of the sample will migrate according to interactions with the stationary phase and the flow of such components are retarded to varying degrees. Individual sample components may reside for some time in the stationary phase (where their velocity is essentially zero) until conditions (e.g., a change in solvent concentration) permit a component to emerge from the column with the mobile phase. In other words, as the sample travels through voids or pores in the stationary phase, the sample may be separated into its constituent species due to the attraction of the species to the stationary phase. The time a particular constituent spends in the stationary phase relative to the fraction of time it spends in the mobile phase will determine its velocity through the column. Following chromatographic separation in the column, the resulting eluate stream (consisting of mobile phase and sample) contains a series of regions having elevated concentrations of individual species, which can be detected by various techniques to identify and/or quantify the species.

As illustrated in FIG. 1, a separation column for use in a conventional hydrostatic pressure-driven chromatography system is typically fabricated by packing particulate material 14 into a tubular column body 12. A conventional column body 12 has a high precision internal bore 13 and may be manufactured with stainless steel, although materials such as glass, fused silica, and/or PEEK are also used. Various methods for packing a column body are known, although such methods are notoriously slow and laborious. In one example, a simple packing method involves dry-packing an empty tube by shaking particles downward with the aid of vibration from a sonicator bath or an engraving tool. A cut-back pipette tip may be used as a particulate reservoir at the top (second end), and the tube to be packed is plugged with parafilm or a tube cap at the bottom (first end). Following dry packing, the plug is removed and the tube 10 is then secured at the first end with a ferrule 16A, a fine porous stainless steel fritted filter disc (or "frit") 18, a male end fitting 20A, and a female nut 22A that engages the end fitting 20A. Corresponding connectors (namely, a ferrule 16B, a male end fitting 20B, and a female nut 22B) except for the frit 18 are engaged to the second end to secure the dry-packed tube 12. The contents 14 of the tube 12 may be further compressed by flowing pressurized solvent through the packing material 14 from the second end toward the first (frit-containing) end. When compacting of the particle bed has ceased and the fluid pressure has stabilized, there typically remains some portion of the tube 13 that does not contain densely packed particulate material. To eliminate the presence of a void in the column 10, the tube 13 is typically cut down to the bed surface (or a shorter desired length) to ensure that the resulting length of the entire tube 12 contains packed particulate 14, and any unpacked tube section is discarded. Thereafter, the column 10 is reassembled (i.e., with the ferrule 16B, male end fitting 20B, and female nut 22B affixed to the second end) before use.

In another packing method utilizing slurry, an empty tube is attached to a packing reservoir such as a Poros® Self-Pack® reservoir (PerSeptive Biosystems, Foster City, Calif.) before being filled with an appropriate amount of dilute slurry. The end of the reservoir column is then screwed on firmly before the tube is internally pressurized with a fluid using an appropriate device such as a pump. Pressures of several hundreds or even thousands of pounds per square inch (psi) may be applied to pack the tube with particulate packing material, with the ultimate pressure depending on the properties of the tubing and the ability to seal the apparatus from leakage. A packed tube may be cut following the packing step to remove any dead volume (i.e., where packing is incomplete or not present) or to yield multiple sections, followed by the addition of end fittings to the uncapped tube ends to permit subsequent interface with fluidic components.

A conventional pressure-driven liquid chromatography system utilizing a column 10 is illustrated in FIG. 2. The system 30 includes a solvent reservoir 32, at least one high pressure pump 34, a pulse damper 36, a sample injection valve 38, and a sample source 40 all located upstream of the column 10, and further includes a detector 42 and a waste reservoir 44 located downstream of the column 10. The high pressure pump(s) 34 pressurize mobile phase solvent from the reservoir 32. A pulse damper 36 serves to reduce pressure pulses caused by the pump(s) 34. The sample injection valve 38 is typically a rotary valve having an internal sample loop for injecting a predetermined volume of sample from the sample source 40 into the solvent stream. Downstream of the sample injection valve 38, the column 10 contains stationary phase material that aids in separating species of the sample. Downstream of the column 10 is a detector 42 for detecting the separated species, and a waste reservoir 44 for ultimately collecting the mobile phase and sample products. A backpressure regulator (not shown) may be disposed between the column 10 and the detector 42. Many components of the system 30 are precision manufactured, thus elevating the cost of a typical high performance liquid chromatography system 30 to approximately $20,000-$30,000 or more. Given the rising demand for chromatographic separations, once such a system 30 is purchased, it may be operated on a nearly continuous basis.

The system 30 generally permits one sample to be separated at a time in the column 10. Due to the cost of conventional tubular chromatography columns, they are often re-used for many (e.g., typically about one hundred or more) separations. Following one separation, the column 10 may be flushed with a pressurized solvent stream in an attempt to remove any sample components still contained in the stationary phase material 14. However, this time-consuming flushing or cleaning step does not always yield a completely clean column 10. This means that, after the first separation performed on a particular column, every subsequent separation may potentially include false results due to contaminants left behind on the column from a previous run. Eventually, columns become fouled to the point that they are no longer useful, at which point they are removed from service and replaced.

A known method for increasing separation throughput is to modify a conventional chromatography system to split the flow from a common source of mobile phase (typically one or two pumps) to several chromatography columns. Such a system 50 is illustrated in FIG. 3. Mobile phase solvent from a solvent reservoir 52 is pressurized by one or more common high pressure pumps 54, and pressure variations caused by the common pump(s) 54 are damped by a common pulse damper 56. Downstream of the pulse damper 56, the solvent flow is split among multiple columns 10A, 10B, 10N each having an injection valve 58A, 58B, 58N and sample source 60A, 60B, 60N. (Although FIG. 3 shows three columns 10A, 10B, 10N, it will be readily apparent that any number of columns 10A, 10B, 10N may be provided. For this reason, the designation "N" is used to represent the last column 10N, with the understanding that "N" represents a variable and could represent any desired number of columns. This convention is used throughout this document.) Downstream of each column 10A, 10B, 10N is a detector 62A, 62B, 62N and waste reservoir 64A, 64B, 64N.

Compared to the single column system 30 described in connection with FIG. 2, the multi-column system 50 permits significantly higher throughput, since several samples can be analyzed in parallel. Additionally, this increased throughput may be obtained at a lower cost per separation, since the cost of expensive solvent delivery components (particularly the high pressure pumps 54 and pulse damper 56) can be spread over multiple columns 10A-10N. That is, a parallel chromatography system 50 having common solvent delivery components and several (i.e., "N") separation columns is substantially less expensive than a comparable ("N") number of chromatography systems each having discrete solvent delivery components. Moreover, the use of common solvent delivery components for a group of separation columns is substantially more compact than providing such components for each column, thus saving valuable laboratory space.

Despite the potential advantages of a multi-column separation system 50 having common mobile phase delivery components, such a system 50 presents complicating issues compared to the use of single column systems (such as the system 30 illustrated in FIG. 2). One issue is evenly splitting or balancing the flow of mobile phase through each column of the multi-column system 50. It would be desirable to provide the same flow conditions to each column of the multi-column system 50, but this is difficult to ensure for a number of reasons. To begin with, it can be difficult to precisely match the inlet and outlet volumes to each column when tubing and conventional connectors are used since tube lengths and flow characteristics through different connectors often vary. More importantly, individual columns tend to exhibit different fluidic impedance characteristics that prevent a common input stream from being divided evenly between the various columns since columns are typically packed one at a time or in an independent manner. Thus, depending on the specific fluid dynamics of a given packing process, the impedance characteristics of different columns typically vary significantly. In a linked multi-column system such as shown in FIG. 3, these column-to-column variations in flow may be caused by imperfect operation of any flow splitter(s) disposed upstream of the multiple columns, as well as by slight differences in column packing density, column geometry, and interfaces with the columns (e.g., fittings or other interfaces with fluidic supply components). It can be difficult to provide the same flow characteristics to each individual column of a group of columns due to these variations in fluidic impedance, since fluid flow will be biased toward the column(s) and overall flow paths with the least fluidic impedance.

To further complicate matters, many commonly employed chromatographic techniques utilize a "gradient" solvent profile that changes with time as opposed to an "isocratic" solvent profile that remains constant. For example, reverse phase chromatographic techniques often use an organic solvent/water gradient elution in which the concentration of the two solvents is varied with time by independently controllable pumps. Typically, separations in reverse phase chromatography depend on the reversible adsorption/desorption of solute molecules with varying degrees of hydrophobicity to a hydrophobic stationary phase. Thus, in a multi-column system employing a common set of pumps for performing gradient elution, the presence of a changing solvent concentration exacerbates the difficulty of ensuring that identical mobile phase conditions (i.e., including flow rate and concentration) are provided to each column at the same time.

Although active flow control systems (e.g., flow sensors and regulating valves) might be employed to reduce column-to-column fluid flow variation, active flow control systems are mechanically complex and expensive, and may not be suitable for use in extremely low flow environments. Moreover, active control systems may be difficult to tune so as to avoid hysteresis problems.

Due to the difficulty of providing identical mobile phase conditions (including both flowrate and mobile phase composition) to each column in a multi-column system utilizing common mobile phase supply components, seemingly identical columns tend to perform differently. That is, if the same sample is provided to each column in such a system, individual species exhibit different retention times from one column to another. As a result, it can be difficult to compare analytical results obtained from different columns in the same system.

Linking multiple discrete columns to a common mobile phase source raises some system packaging concerns. If the system is operated in gradient mode, it would be desirable to link the common mobile phase source to the columns with low volume conduit system to facilitate more rapid separation (i.e., by reducing the delay between the time a new solvent composition is generated and the time that new solvent composition actually reaches the separation columns). Additionally, it would be desirable to link the columns to one or more downstream detectors with low volume conduits to reduce diffusive mixing or band broadening between separated species following separation in the columns. With conventional multi-column systems, however, it may be difficult to physically interconnect all of the various fluid delivery and detection components without fairly significant conduit volumes.

Another potential complication associated with conventional multi-column separation systems—particularly those using threaded end-fittings—is that it is laborious to change columns when they are spent, and that the entire system is incapacitated during a such a procedure. If possible, it would be desirable to reduce unproductive downtime of a parallel separation system.

A further concern associated with the use of conventional multi-column separation systems is their increased consumption of both samples and reagents, leading to increased waste disposal quantities and attendant expenses. It would be desirable to provide a system that could provide high separation throughput without excessive sample and reagent consumption.

In light of the foregoing, there exists a need for an improved high-throughput separation system and methods for fabricating the same.

BRIEF DESCRIPTION OF THE DRAWINGS

FIG. 3 is a schematic of a conventional linked multi-column liquid chromatography system employing multiple tubular separation columns according to the column of FIG. 1.

FIG. 4A is an exploded perspective view of a nine-layer microfluidic separation device containing eight separation columns.

FIG. 4B is a top view of the assembled device of FIG. 4A.

FIG. 4C is an enlarged top view of a first portion of the separation device of FIGS. 4A-4B showing sample injection ports and associated channels.

FIG. 4D is an enlarged top view of a second portion of the separation device of FIGS. 4A-4B showing solvent inlet ports, a mixing region, and a splitting network for splitting and distributing a solvent mixture among eight columns.

FIG. 6A is an exploded perspective view of a first portion, including the first through third layers, of the microfluidic device shown in FIG. 5.

FIG. 6B is an exploded perspective view of a second portion, including the fourth through sixth layers, of the microfluidic device shown in FIG. 5.

FIG. 6C is an exploded perspective view of a third portion, including the seventh through ninth layers, of the microfluidic device shown in FIG. 5.

FIG. 6E is a reduced size composite of FIGS. 6A-6D showing an exploded perspective view of the microfluidic device of FIG. 6.

FIG. 8A is an exploded perspective view of a first portion, including the first through fourth layers, of the microfluidic device shown in FIG. 7.

FIG. 8B is an exploded perspective view of a second portion, including the fifth and sixth layers, of the microfluidic device shown in FIG. 7.

FIG. 8C is an exploded perspective view of a third portion, including the seventh and eighth layers, of the microfluidic device shown in FIG. 7.

FIG. 8D is an exploded perspective view of a fourth portion, including the ninth through twelfth layers, of the microfluidic device shown in FIG. 7.

FIG. 8E is a reduced size composite of FIGS. 8A-8D showing an exploded perspective view of the microfluidic device of FIG. 7.

FIG. 9A is bottom view of a first (upper) plate of a first clamp assembly that may be used to assist in packing columns of the device illustrated in FIGS. 4A-4B.

FIG. 9B is a top view of a second (lower) plate of the same clamp assembly.

FIG. 9C is an end view of the first plate illustrated in FIG. 9A.

FIG. 9D is an end view of the second plate illustrated in FIG. 9B.

FIG. 9E shows the first plate and the second plate of FIGS. 9A-9B with the microfluidic device illustrated in FIGS. 4A-4B superimposed over the first plate.

FIG. 9F is a composite sectional view along section lines "A"-"A" (shown in FIG. 9E) of the clamp assembly, including the first plate and the second plate illustrated in the preceding figures, bolted and clamped around the microfluidic device illustrated in FIGS. 4A-4B.

FIG. 10A is a side view of the device of FIGS. 4A-4B positioned in a second clamp assembly mechanism used to pack the separation columns of the device.

FIG. 10B is an exploded front view of the clamping mechanism of FIG. 1A.

FIG. 12B is a schematic illustration of a cross section of a portion of the system of FIG. 12A depicting the cylinder in a first rotational position.

FIG. 12C is a schematic illustration of a cross section of a portion of the system of FIG. 12A depicting the cylinder in a second rotational position.

FIG. 13 is a schematic illustration of a system utilizing a horizontally disposed cylinder for packing at least one separation column.

FIG. 14 is a schematic illustration of a system utilizing a mechanically stirred cylinder for packing at least one separation column.

FIG. 15 is a schematic illustration of a system utilizing a gravity fed flowing stream for packing at least one separation column.

FIG. 16 is a schematic illustration of a system utilizing a fluidized bed for packing at least one separation column.

FIG. 17A is a perspective view of a fluidic device having a body structure connecting eight tubes suitable for forming separation columns.

FIG. 17B is a bottom view of the device of FIG. 17A.

FIG. 17C is an exploded perspective sectional view of the device of FIGS. 17A-17B along section line "B"-"B".

FIG. 17D is an assembled cross-sectional view of the device of FIGS. 17A-17C along section line "B"-"B".

FIG. 18A is a side assembly view of the device of FIGS. 17A-17D interposed between a fluidic distribution manifold and a flow cell.

FIG. 18B is a partially exploded transparent perspective view of the components illustrated in FIG. 18A.

FIG. 19A is a top view of a multi-column fluidic device having a body structure defining nine channels suitable for forming separation columns.

FIG. 19B is an exploded cross-sectional view of the device of FIG. 19A along section line "C"-"C".

DETAILED DESCRIPTION OF PREFERRED EMBODIMENTS OF THE INVENTION

A. Definitions

Figure 1:
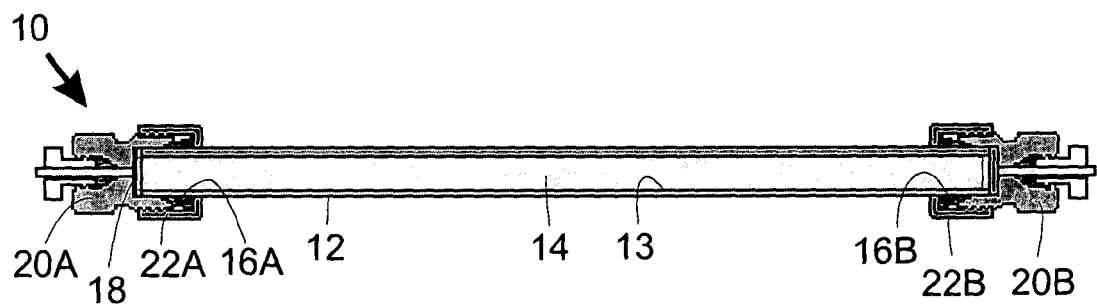
FIG. 1 is a cross-sectional view of a conventional tube-based separation column for performing pressure-driven liquid chromatography.
Figure 2:
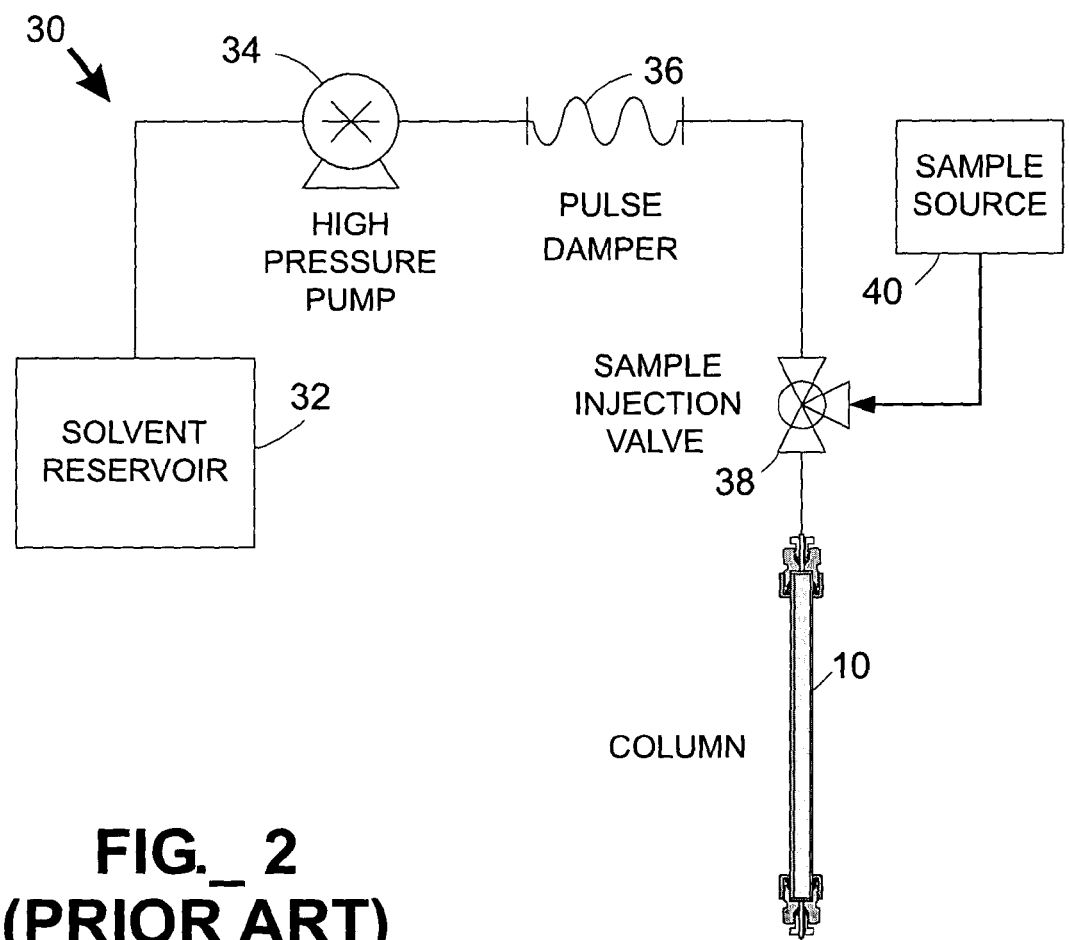
FIG. 2 is a schematic of a conventional liquid chromatography system employing the separation column of FIG. 1.

The term "batch-processed" as used herein refers to the state of being, or having been, produced in a common operation to impart common characteristics. Batch-processed separation columns containing particulate stationary phase material are preferably packed by supplying stationary phase to each column through a common inlet and a distribution manifold.

The terms "column" or "separation column" as used herein are used interchangeably and refer to a region of a fluidic device that contains stationary phase material and is adapted to perform a separation process.

The term "fluidic distribution network" refers to an interconnected, branched group of channels and/or conduits capable of adapted to divide a fluid stream into multiple substreams.

The term "frit" refers to a liquid-permeable material adapted to retain stationary phase material within a separation column.

The term "microfluidic" as used herein refers to structures or devices through which one or more fluids are capable of being passed or directed and having at least one dimension less than about 500 microns.

The term "packed" as used herein refers to the state of being substantially filled with a packing material (such as a particulate material).

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "slurry" as used herein refers to a mixture of particulate matter and a solvent, preferably a suspension of particles in a solvent.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

The term "surface activation" as used herein refers to the intentional addition of reactive surface groups to a polymeric material. Such addition may be performed, for example, by plasma, chemical, or radiation means. Similarly, the term "activated surface" refers to a surface of a polymeric material having an elevated number of reactive surface groups formed by a surface activation process.

B. Multi-Column Devices Generally

Applicants have found that many difficulties associated with conventional multi-column separation systems can be overcome by fabricating a group or batch of separation columns according to substantially identical conditions and physically connecting the resulting group of columns to ensure that the columns are used as a group (such as in a parallel liquid chromatography system). Both packed particulate-based column embodiments and monolithic column embodiments are provided. Preferably, during manufacture and/or use, the grouped columns have an associated fluidic distribution network permitting one or more materials to be split among each column from a common inlet. The intent is to ensure that each column in a multi-column device perform similarly in a parallel liquid chromatography system having common mobile phase delivery components.

In one embodiment employing particulate-based stationary phase material, a slurry bearing the stationary phase is supplied a group of channels each having an outlet including a liquid-permeable frit material. Preferably, a fluidic distribution network having substantially equal fluidic path lengths is used to supply the slurry to each channel of the group to form separation columns. One advantage of utilizing a fluidic distribution network having a common inlet to distribute stationary phase material to a group of would-be columns is that the apparatus is inherently self-correcting, since flow through the resulting system is naturally biased toward the path of least fluidic resistance. In other words, if a first channel (slated to become a first column) is more densely packed than a second channel (slated to become a second column) at any point in time during the slurry supply (packing) process, then the second channel will exhibit a lower fluidic impedance—thus causing more particulate-containing slurry to be diverted to the second channel. Assuming that the remaining components with which the columns are fabricated (e.g., channel materials and dimensions, frits, etc.) are otherwise identical, the use of this self-correcting packing method yields a group of columns with inherently matched performance characteristics. The fluidic impedance of each column within a multi-column device preferably varies by less than about five percent; more preferably varies by less than about two percent; and more preferably still varies by less than about one percent.

When provided, a fluidic distribution network in fluid communication with a group of physically connected columns also aids operation of the system. In one embodiment, a fluidic distribution network includes equal path length channels to aid in providing substantially identical flow conditions to each column of the multi-column system at any point in time. That is, mobile phase supplied to a common inlet of the fluidic distribution network may be split evenly to a group of batch-processed columns to help promote not only even flow distribution of mobile phase among each column but also a consistent mobile phase composition profile of the supply to each column.

Column fabrication methods as disclosed herein may be applied to various types of fluidic devices, including devices utilizing one or more conventional-scale tubes, capillary tubes, or microfluidic channels. Preferable tubing materials include metals (such as, for example, stainless steel), plastics (such as, for example, PEEK), and glasses, with the selection of particular materials depending on the anticipated samples and solvents, flow conditions (including pressure) and manufacturing methods to be used, as will be recognized by one of ordinary skill in the art.

Various types of body structures may be used to connect groups of batch-processed separation columns. A body structure may be provided as a unitary (single-piece) element or may be assembled from multiple pieces. Exemplary fabrication methods include molding, casting, machining/milling, and/or drawing/extrusion. Channels may be formed directly within a body structure without interposing channel-defining elements such as hollow tubes. Alternatively, the body structure may serve to connect multiple tubes or other channel-defining elements. For example, a group of structurally identical tubes each having a liquid permeable frit disposed at one end may be connected by a body structure. One or more frits may also be integrated directly into the body structure. Additionally, in one embodiment, a column-containing body structure contains an integral fluidic distribution network.

In a preferred embodiment, a body structure facilitates rapid interconnection with mobile phase and/or sample supply components. In one embodiment, a body structure includes at least one surface adapted to threadlessly engage a mating surface of an external clamping apparatus. For example, a compressible material may be provided along the interface between an external clamping apparatus and a body structure to facilitate compressive sealing. The compressible material may include a reusable or disposable gasket, or one mating surface of either the body structure or clamping apparatus may be at least somewhat compressible. Alternatively, one or more tapered interconnects may be provided between a body structure and an external apparatus. As a further alternative, one or more threaded connections such as endfittings may be used.

In one embodiment, each separation column may have an associated sample injection valve. Such valves are widely available from companies such as Rheodyne (Rohnert Park, Calif.), with one specific example including Rheodyne® Model 7725. If a fluidic distribution network is provided in conjunction with multiple sample injection valves, then the fluidic distribution network is preferably located upstream of the sample injection valves. As an alternative to using sample injection valves, stop-flow sample injection methods may be used. One such method includes on-column injection in which each column includes a sample access port downstream of the leading edge of the stationary phase material, such that the flow of mobile phase can be paused to permit fluidic access to the sample access ports. For example, a moveable contact-type interface (e.g., preferably gasketed or including otherwise compressible materials) may be provided along the sample access ports to permit periodic sample loading. With such a system, a frit material is preferably provided along each sample access port to retain stationary phase material within the columns. Following sample loading, mobile phase flow is resumed to effect chromatographic separation in each column.

In certain embodiments, each column of a group of separation columns is microfluidic. Generally, microfluidic devices may be fabricated from materials such as glass, silicon-based materials, quartz, metals, and numerous polymers. Various well-established techniques may be used to fabricated microfluidic devices, including machining, micromachining (including, for example, photolithographic wet or dry etching), micromolding, LIGA, soft lithography, embossing, stamping, surface deposition, and/or combinations thereof to define apertures, channels or chambers in one or more surfaces of a material or that even penetrate through a material.

1. Stencil Fabrication

A preferred method for constructing microfluidic devices includes stencil fabrication including the lamination of at least three device layers including one or more stencil layers or sheets that define microfluidic channels and/or other microstructures. For example, a computer-controlled plotter modified to accept a cutting blade may be used to cut various patterns through a material layer. Such a blade may be used either to cut sections to be detached and removed from the stencil layer or to fashion slits that separate certain regions of a layer without removing any material. Alternatively, a computer-controlled laser cutter may be sued to cut portions through a layer of material. While laser cutting may be used to yield precisely-dimensioned microstructures, the use of a laser to cut a stencil layer inherently involves the removal of some material. Further examples of methods that may be employed to form stencil layers include conventional stamping or die-cutting technologies. The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port. The resulting channels typically have a substantially rectangular cross-section.

Various means may be used to seal or bond layers of a device together. For example, adhesives may be used. In one embodiment, one or more layers of a device may be fabricated from single- or double-sided adhesive tape, although other methods of adhering stencil layers may be used. A portion of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thicknesses of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. Desirable operating pressures are preferably greater than about 10 psi (69 kPa), more preferably greater than about 100 psi (690 kPa), and more preferably still greater than about 400 psi (2.8 MPa). Specific examples of methods for directly bonding layers of unoriented polyolefins such as unoriented polypropylene to form stencil-based microfluidic structures are disclosed in co-pending U.S. patent application Ser. No. 10/313,231 (filed Dec. 6, 2002), which is owned by assignee of the present application and incorporated by reference as if fully set forth herein. In one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately 5 hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

C. Particulate-Containing Multi-Column Devices

In at least one preferred embodiment, a pressure-driven fluidic device includes multiple channels that are packed as a batch to form separation columns sufficient for performing liquid chromatography at elevated operating pressures. Preferably, such a device has as least one associated fluidic distribution network having at least one common input to permit packing with particulate-containing slurry and/or operation with a minimum number of expensive system components such as pumps, pulse dampers, etc. Both microfluidic and conventional-scale fluidic embodiments are provided.

1. Devices Constructed with Laminated Device Layers

In one embodiment, pressure-driven separation device may be fabricated from multiple substantially planar device layers laminated together. For example, FIGS. 4A-4B illustrate a microfluidic separation device 100 including eight separation channels 145A-145N containing stationary phase material 147. (Although FIGS. 4A-4B show the device 100 having eight separation columns 145A-145N, it will be readily apparent to one skilled in the art that any number of columns 145A-145N may be provided. For this reason, the designation "N" represents a variable and could represent any desired number of columns. This convention is used throughout this document.) The device 100 may be constructed with nine substantially planar device layers 111-119, including multiple stencil layers 112-118. Each of the nine device layers 111-119 defines two alignment holes 120, 121, which are used in conjunction with external pins (not shown) to aid in aligning the layers 111-119 during construction, and/or to aid in aligning the device 100 with an external interface during a packing process.

The first device layer 111 defines several fluidic ports: two solvent inlet ports 122, 124 are used to admit (mobile phase) solvent to the device 100; eight sample ports 128A-128N permit sample to be introduced to eight columns (provided in channels 145); a slurry inlet port 126 is used during a column packing process to admit slurry to the device 100; and a fluidic outlet port 130 that is used [1] during the packing process to exhaust (slurry) solvent from the device 100; and [2] during operation of the separation device 100 to carry effluent from the device 100. Alternatively, multiple outlet ports (not shown) may be provided to separately transport the effluent stream from each separation channel 145A-145N off of the device 100. Due to the sheer number of elements depicted in FIGS. 4A-4B, numbers for selected elements within alphanumeric series groups (e.g., sample inlet ports 128A-128N are omitted from the drawings for clarity.

Each of the first through sixth layers 111-116 defines eight optical detection windows 132A-132N. Defining these windows 132A-132N through these device layers 111-116 facilitates optical detection by locally reducing the thickness of material bounding (from above and below) channel segments 169A-169N disposed downstream of the column-containing channels 145A-145N, thus reducing the amount of material between an external optical detector (not shown) such as a conventional UV-VIS detector, and the samples contained in the segments 169A-169N. Various types of optical detectors may be used to detect at least one property of a substance eluted from the packed separation channels 145A-145N.

The second through seventh layers 112-117 each define a first solvent via 122A for communicating a mobile phase solvent from a first mobile phase inlet port 122 to a first mobile phase channel 164 defined in the eighth layer 118, with further solvent vias 124A defined in the second through fifth layers 112-115 to transport a second mobile phase solvent to the channel 146 defined in the sixth layer 116. Additional vias 130A are defined in the second through sixth layers 112-116 to provide a fluid path between the fluidic port 130 and the effluent channel 162 defined in the seventh layer 117. A via 126A defined in the second layer 112 communicates slurry from the slurry inlet port 126 to a transverse channel 138 defined in the third layer 113 during a slurry packing process. Preferably, particulate material deposited by the slurry packing process fills not only the multiple separation channels 145A-145N, but also fills the channel 142 and at least a portion of the channel 138. The second layer 112 further defines eight sample channels 135A-135N each having an enlarged region 134A-134N aligned with a sample inlet port 128A-128N defined in the first layer 111.

In addition to the structures described previously, the third layer 113 defines an elongate channel 138, and eight sample vias 136A-136N each aligned with the ends of a corresponding sample channel 135A-135N. The fourth layer 114 defines a manifold channel 142 and eight sample vias 144A-144N aligned with the vias 136A-136N in the third layer 113. The manifold channel 142 that provides fluid communication with the separation channels 145 defined in the fifth layer 115 and the elongate channel 138 defined in the third layer 113. The separation channels 145 preferably are about 40 mils (1 mm) wide or smaller. As an alternative to the manifold channel 142, a junction with radiating segments (not shown) could be used.

A porous (sample) frit 140 is disposed between the third layer 113 and fourth layers 114. The function of this frit 140 is to retain stationary phase material 147 in the separation channels 145A-145N, yet permit the passage of fluid when desired (i.e., fluidic samples supplied to the device 100 through the sample ports 128A-128N). Although various frit materials may be used, the frit 140 (along with frits 150, 151) is preferably constructed from a liquid-permeable microporous polypropylene membrane such as, for example, 1-mil thickness Celgard 2500 membrane (55% porosity, 0.209×0.054 micron pore size, Celgard Inc., Charlotte, N.C.), particularly if the layers 111-119 of the device 100 are bonded together using an adhesiveless thermal bonding method utilizing platens, such as described above. Preferably, the frit material has an average pore size that is smaller than the average particle size of the particulate to be packed within the device 100, so as to ensure that the packing material is retained within the device 100. Applicants have obtained favorable results using this specific frit material, without noticeable wicking or lateral flow within the frit despite using a single strip 140 of the frit membrane to serve multiple adjacent column-containing channels. As a less-preferred alternative to the single frit 140, multiple discrete frits (not shown) of various porous material types and thicknesses may be substituted.

The sixth layer 116 defines a channel 146 that communicates a second mobile phase solvent from vias 124A to the slit 152 defined in the seventh layer 117, which facilitates mixing of the two solvents in the channel 164 downstream of the slit 152. Further defined in the sixth layer 116 are eight vias 148A-148N for admitting mixed mobile phase solvent to the upstream ends of the separation channels 145A-145N, and a second set of eight vias 149A-149N at the downstream end of the same separation channels 145 for transporting effluent from the downstream ends of the separation channels 145A-145N. Two frits 150, 151 are placed between the sixth and the seventh layers 116, 117. The first (mobile phase solvent) frit 150 is placed immediately above the first set of eight vias 148A-148N, while the second (mobile phase+ sample) frit 151 is placed immediately above the second set of eight vias 149A-149N and below a similar set of eight vias 160A-160N defined in the seventh layer 117. The seventh layer 117 defines a channel segment 158, two medium forked channel segments 168A-168B, and eight vias 154A-154N for communicating mobile phase solvent through the frit 150 and the vias 148A-148N to the separation channels 145A-145N defined in the fifth layer 115. The seventh layer 117 further defines a downstream manifold channel 162 that receives mobile phase solvent and sample during separation, and that receives (slurry) solvent during column packing, for routing such fluids through vias 130A to the fluidic exit port 130 defined in the first device layer 111.

The eighth layer 118 defines a mixing channel 164, one large forked channel segment 168, and four small forked channel segments 166A-166D. The eighth layer 118 further defines eight parallel channel segments 169A-169N downstream of the frit 151 for receiving effluent during separation or solvent during slurry packing, and for transporting such fluid(s) to the manifold channel 162 defined in the seventh layer 117. The ninth layer 119 serves as a cover for the channel structures defined in the eighth layer 118.

FIG. 4B is a top view of the assembled device 100 of FIG. 4A. FIGS. 4C-4D provide expanded views of two portions of the device 100. FIG. 4C shows the sample injection channels 135A-135N with associated enlarged regions 134A-134N that are aligned with the sample inlet ports 128A-128N defined in the first layer 111. For simplicity, the frit 140 has been omitted from FIG. 4C, although FIGS. 4A-4B correctly show the frit 140 placed between the sample vias 136A-136N, 144A-144N upstream of the point where samples are injected onto the separation channels 145A-145N to be filled with packed particulate stationary phase material. FIG. 4D shows the mixing and splitting channel structures that communicate mobile phase solvent to the column-containing channels 145A-145N. During operation of the device 100, a first mobile phase solvent is injected into a first solvent inlet port 122 and flows into a channel 164. A second mobile phase solvent is injected into a second solvent inlet port 124 and flows through a channel segment 146 and through a slit 152 where it is layered with and joins the first solvent in the channel 164. The two layered solvents mix in the channel 164 and subsequent channel segment 158, whereafter the mixed solvent stream is split into eight portions or substreams by way of transport through a splitter 155 comprising a large forked channel segment 168, two medium forked channel segments 156A, 156B, and four small forked channel segments 166A-166D. The eight solvent mixture substreams are then injected through vias 154A-154N and 148A-148N into the (column-containing)

separation channels 145A-145N. For simplicity, the frit 150 disposed between the vias 154A-154N and 148A-148N have been omitted in FIG. 4D, although this frit 150 is properly included in FIGS. 4A-4B.

Preferably, the various layers 111-119 of the device 100 are fabricated from un-oriented polypropylene and bonded using an adhesiveless thermal bonding method, such as methods employing platens as described above. This construction method yields chemically-resistant devices having high bond strength, both desirable attributes for withstanding a column packing process and subsequent operation to provide separation utility. Additionally, since polymeric materials are relatively inexpensive and only a relatively small amount of expensive packing material is required within the device 100, it is feasible to sell the device 100 as a disposable cartridge.

While separation columns of various lengths may be provided in separation devices according to the present invention such as the device 100, preferably such columns are greater than or equal to about 1 cm in length to provide reasonable separation efficiency. Columns much longer than 1 cm may be fabricated according to methods described herein.

While the device 100 illustrated in FIGS. 4A-4D represents a preferred fluidic device, a wide variety of other fluidic devices may be used. In certain embodiments, fluidic device may include one or more tubes, particularly capillary tubes. For example, capillary tubes may be embedded in one or more channels of a microfluidic device.

As mentioned previously, particulate material deposited by a slurry packing process preferably fills the manifold or junction channel 142 and at least a portion of the upstream channel 138. This leaves a "trailing edge" of packing (particulate) material in the channel 138 that is far removed from the injection region (i.e., the mobile phase injection vias 144A-144N adjacent to the frit 140 and the sample injection vias 148A-148N adjacent to the frit 150) where mobile phase and sample are provided to the column-containing channels 145A-145N. In operation, the mobile phase and sample are injected directly onto the columns in channels 145A-145N, well downstream of the trailing edge of particulate material in the channel 138. It is beneficial to avoid sample flow through the trailing edge region of the particulate to promote high-quality separation, since the trailing edge is typically not well-packed. That is, since the quality of separation in chromatography depends heavily on the size of the injection plug, with a small and well-defined plug generally providing better results, it is desirable to avoid injecting a sample into a region that is not uniformly packed with particulate. On-column injection well downstream of the trailing edge of the packing material promotes small and well-defined sample plugs.

In liquid chromatography applications, it is often desirable to alter the makeup of the mobile phase during a particular separation. If multiple separation columns are provided in a single integrated device (such as the device 100) and the makeup of the mobile phase is subject to change over time, then at a common linear distance from the mobile phase inlet it is desirable for mobile phase to have a substantially identical composition from one column to the next. This is achieved with the device 100 due to two factors: (1) volume of the path of each (split) mobile phase solvent substream (shown in FIG. 4D) is substantially the same to each column; and (2) each flow path downstream of the fluidic (mobile phase and sample) inlets is characterized by substantially the same impedance. The first factor, substantially equal substream flow paths, is promoted by design of the composite splitter incorporating elements 158, 168, 156A-156B, and 166A-166D. The second factor, substantial equality of the impedance of each column, is promoted by both design of the fluidic device 100 and the fabrication of multiple column in fluid communication (e.g., having a common outlet) using a slurry packing method disclosed herein. Where multiple columns are in fluid communication with a common outlet, slurry flow within the device 100 is biased toward any low impedance region. The more slurry that flows to a particular region during the packing process, the more particulate is deposited to locally elevate the impedance, thus yielding a self-correcting method for producing substantially equal impedance from one column to the next.

Microfluidic separation devices may include substantially more than eight separation channels, and the number of separation channels need not be an even exponential of two. For example, a microfluidic separation device 610 including twenty-four separation channels 639-639N is illustrated in FIG. 5 and FIGS. 6A-6E. The microfluidic separation device 610 is constructed with twelve device layers 611-622, including multiple stencil layers 614, 615, 617, 618, 620. Each of the twelve device layers 611-622 defines five alignment holes 623-627, which are used in conjunction with external pins (not shown) to aid in aligning the layers during construction or in aligning the device 610 with an external interface such as a clamping apparatus (not shown) during a packing process or during operation of the device 610.

The first through third layers 611-613 define a plurality of sample ports/vias 628A-628N that permit samples to be introduced to a plurality of separation columns 639A-639N (defined in the seventh device layer 617) and a plurality of optical detection windows 630A-630N. Two sample ports 628A-628N and 629A-629N are associated with each separation column 639A-639N to permit injection of precise volumes or "plugs" of sample into each column 639A-639N. Optical detection windows 630A-630N also are defined in the first through eighth and twelfth device layers 611-618, 622. The optical detection windows 630A-630N facilitate optical detection by reducing the amount of material between an optical detector (not shown), such as a conventional UV-Vis detector, and the samples contained in output analysis channels 632A-632N (defined in the tenth device layer 620) downstream of the columns 639A-639N.

The fourth through sixth layers 614-616 define a mobile phase distribution network 640 that includes a mobile phase mixing channel 642, a composite mixing channel 644 (composed of a plurality of mixer segments 646A-646N) and a mobile phase splitter 648 (composed of a plurality of splitter segments 650A-650N). The fourth device layer 614 defines a plurality of sample injection channels 654A-654N. A first frit 652 is disposed between the mobile phase splitter 648 and the sample injection channels 654A-654N. The first frit 652 (and the other frits described below) is preferably constructed from a permeable polypropylene membrane such as, for example, 1-mil thickness Celgard 2500 membrane (55% porosity, 0.209×0.054 micron pore size, Celgard Inc., Charlotte, N.C.). The fifth and sixth device layers 615, 616 define a plurality of sample injection vias 656A-656N and 657A-657N. A second frit 658 is disposed between the sample injection vias 656A-656N in the fifth device layer 615 and the sample injection vias 657A-657N in the sixth device layer 616. The fifth through twelfth device layers 615-622 define the first mobile phase vias 664A-664H, which are in fluidic communication with each other and the mobile phase mixing channel 642.

The fifth and sixth device layers 615, 616 define second mobile phase mixer slits 660, 662, which are in fluidic communication with each other and the mobile phase mixing channel 642. The seventh device layer 617 defines a channel segment 666, which is in fluidic communication with the second mobile phase mixer slits 660, 662 and a plurality of second mobile phase input vias 668A-668D and port 668E defined in the eighth through twelfth device layers 618-622.

The seventh device layer 617 defines the separation channels 639A-639N. The seventh device layer 617 together with the eighth device layer 618 define a slurry distribution network 670 that includes a slurry input channel 672 and a slurry splitter 674 (made up of slurry splitter segments 676A-676N). The eighth through twelfth device layers 618-622 define a plurality of slurry vias 678A-678N, which are in fluidic communication with each other and the slurry input channel 642.

The eighth and ninth device layers 618, 619 define a plurality of separation column output vias 680A-680N in fluid communication with each other and the separation columns 639A-639N. A third frit 682 is interposed between the separation column output vias 680A-680N in the eighth device layer 618 and the separation column output vias 680A-680N in the ninth device layer 619.

The tenth device layer 620 defines a plurality of output analysis channels 632A-632N, each including an optical alignment segment 686A-686N (which is aligned with the optical detection windows 630A-630N defined in the first through eighth and twelfth device layers 611-618, 622. Effluent vias 689A-689N, 688A-688N are defined in the eleventh and twelfth device layers 621, 622 and are in fluid communication with each other and the output analysis channels 632A-632N. Fourth and fifth frits 690, 692 are interposed between the effluent vias 689A-689N in the eleventh device layer 621 and the effluent vias 688A-688N in the twelfth device layer 622.

In operation, the columns 639A-639N of the device 610 are packed with the desired stationary phase material, typically silica-based particles to which hydrophobic C-18 (or other carbon-based) functional groups have been added. A slurry of a solvent (such as acetonitrile) and particulate is injected through the slurry vias 678A-678N into the slurry input channel 672 and the slurry splitter 674, whereupon the slurry is distributed to each of the columns 639A-639N. The second and third frits 658, 682 prevent the slurry from exiting the columns 639A-639N through either the separation column output vias 680A-680N or the sample injection vias 656A-656N. Once the columns 639A-639N are packed, the slurry input channel 672 may be sealed to prevent unpacking therethrough. Alternatively, solvent may be injected through the slurry input channel 672 during operation of the separation device, thus allowing the fluidic pressure of the solvent to maintain the desired packing density.

To perform a chromatographic separation using the device 610, the packed device is placed in a chromatography instrument having a clamshell-type gasketed interface, such as described in copending U.S. patent application Ser. No. 60/422,901 filed on Oct. 31, 2002, which application is hereby incorporated by reference. One or more solvents are provided to the device 610 through the first and second solvent input ports 664H, 668E. If two solvents are used (for example, to perform a gradient separation) the solvents are combined as the second solvent enters the solvent mixing channel 642 through the second mobile phase mixer slits 660, 662. The convoluted channel formed by channel segments 646A-646N serves to provide sufficient channel length to permit mixing downstream of the overlap between slit 662 and the mixing channel 642 (enhanced by the plurality of directional changes experienced by the mobile phase). After the mixing, the mobile phase enters the mobile phase splitter 648, where it is evenly distributed to each of the columns 639A-639N and flows out of the device through the effluent vias 689A-689N and outlet ports 688A-688N.

Once the device 610 is thoroughly wetted with mobile phase, the flow of mobile phase is suspended and samples are injected into the sample input ports 628A-628N. Once the samples are input, the sample input ports 628A-628N are sealed and the flow of mobile phase is resumed, carrying the samples through the columns 639A-639N thereby performing the desired separation. Analytical instruments (not shown) may observe the results of the separation through the optical detection windows 630A-630N. Alternatively, or additionally, the effluent may be collected from the effluent vias 688A-688N for additional analysis.

Preferably, the various layers 611-622 of the device 610 are fabricated from un-oriented polypropylene and bonded using an adhesiveless thermal bonding method utilizing platens, as described above. This construction method yields chemically-resistant devices having high bond strength, both desirable attributes for withstanding a column packing process and subsequent operation to provide separation utility.

Another microfluidic separation device 410 including twenty-four separation channels 439A-439N but intended for use with off-board detection means (not shown) is illustrated in FIG. 7 and FIGS. 8A-8E. Preferably, the device 410 is operated with an external chromatography instrument having a clamshell-type gasketed interface such as described in copending U.S. patent application Ser. No. 60/422,901 filed on Oct. 31, 2002. The microfluidic separation device 410 is constructed with twelve device layers 411-422, including multiple stencil layers 414-420. Each of the twelve device layers 411-422 defines five alignment holes 423-427 (with hole 424 configured as a slot), which are used in conjunction with external pins (not shown) to aid in aligning the layers during construction or in aligning the device 410 with an external interface such as a clamping apparatus (not shown) during a packing process or during operation of the device 410.

As opposed to the preceding two devices 10, 610 described previously, the device 410 lacks on-board optical detection regions. Rather, the device 410 is intended for use with off-board detection means. Preferably, the off-board detection means includes a multi-channel flow cell (such as shown in FIGS. 18A-18B) permitting flow-through optical (e.g., UV-Vis) detection. Alternatively, the off-board detection means may include any of various detection technologies known in the art, including mass spectroscopy. One advantage of using off-board detection means is that it may contribute to the disposability of the device 410, since bulky, expensive, or hard-to-fabricate, or otherwise non-disposable detection components may be provided separately from the device 410. Additionally, the capability to fabricate the detection means using different materials than the device 410 may be advantageous to optimize detection response. For example, quartz or glass materials are more optically transmissive than many polymers. It may be advantageous from a fabrication perspective to construct the device 410 with polymers, yet also advantageous from a performance standpoint to construct at least a portion of the detection means with glass, quartz or similar materials.

Broadly, the device 410 includes various structures adapted to distribute particulate-based slurry material among multiple separation channels 439A-439N (to become columns upon addition of stationary phase material), to retain the stationary phase material within the device 410, to mix and distribute mobile phase solvents among the separation channels 439A-439N, to receive samples, to convey eluate streams from the device 410, and to convey a waste stream from the device 410.

The first through third layers 411-413 of the device 410 are identical and define multiple sample ports/vias 428A-428N that permit samples to be supplied to channels 454A-454N defined in the fourth layer 414. While three separate identical layers 411-413 are shown (to promote strength and increase the aggregate volume of the sample ports/vias 428A-428N to aid in sample loading), a single equivalent layer (not shown) having the same aggregate thickness could be substituted. The fourth through sixth layers 414-416 define a mobile phase distribution network 450 (including elements 450A-450N) adapted to split a supply of mobile phase solvent among twenty-four channel loading segments 454A-454N disposed just upstream of a like number of separation channels (columns) 439A-439N. Upstream of the mobile phase distribution network 450, the fourth through seventh layers 414-417 further define mobile phase channels 448-449 and structures for mixing mobile phase solvents, including a long mixing channel 442, wide slits 460A-460B, alternating channel segments 446A-446N (defined in the fourth and sixth layers 414-416) and vias 447A-447N (defined in the fifth layer 415).

Following assembly of the twelve layers 411-422, stationary phase material is added to the device 410, preferably in the form of a slurry. Preferred slurries include silica-based particles to which hydrophobic C-18 (or other carbon-based) functional groups have been added within a (preferably organic) solvent such as acetonitrile. Slurry is supplied to the device 410 by way of a slurry inlet port 471 and channel structures defined in the seventh through ninth device layers 417-419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476N each having three outlets, and twenty-four column outlet vias 480A-480N. The seventh layer 417 defines four small forked channels 476C in addition to the separation channels 439A-439N. In the aggregate, the large, medium, small, and smaller forked channels 476A-476N form a slurry distribution network that communicates slurry from a single inlet (e.g., slurry inlet port 471) to twenty-four separation channels 439A-439N (to become separation columns 439A-439N upon addition of stationary phase material). Upon addition of particulate-containing slurry to the separation channels 439A-439N, the particulate stationary phase material is retained within the separation channels by one downstream porous frit 496 and by one sample loading porous frit 456. Each of the frits 436, 438, 456, 496 may be fabricated from strips of the same porous material, e.g., 1-mil thickness Celgard 2500 membrane (55% porosity, 0.209×0.054 micron pore size, Celgard Inc., Charlotte, N.C.). After stationary phase material is packed into the columns 439A-439N, a sealant (preferably substantially inert such as UV-curable epoxy) is added to the slurry inlet port 471 to prevent the columns from unpacking during operation of the device 410. The addition of sealant should be controlled to prevent blockage of the waste channel segment 472A.

To prepare the device 410 for operation, one or more mobile phase solvents may be supplied to the device 410 through mobile phase inlet ports 464, 468 defined in the twelfth layer 422. These solvents may be optionally pre-mixed upstream of the device 410 using a conventional micromixer. Alternatively, these solvents are conveyed through several vias (464A-464F, 468A-468C) before mixing. One solvent is provided to the end of the long mixing channel 442, while the other solvent is provided to a short mixing segment 466 that overlaps the mixing channel 442 through wide slits 460A-460B defined in the fifth and sixth layers 415, 416, respectively. One solvent is layered atop the other across the entire width of the long mixing channel 442 to promote diffusive mixing. To ensure that the solvent mixing is complete, however, the combined solvents also flow through an additional mixer composed of alternating channel segments 446A-446N and vias 447A-447N. The net effect of these alternating segments 446A-446N and vias 447A-447N is to cause the combined solvent stream to contract and expand repeatedly, augmenting mixing between the two solvents. The mixed solvents are supplied through channel segments 448, 449 to the distribution network 450 including one large forked channel 450A each having two outlets, two medium forked channels 450B each having two outlets, four small forked channels 450C each having two outlets, and eight smaller forked channels 450N each having three outlets.

Each of the eight smaller forked channels 450A-450N is in fluid communication with three of twenty-four sample loading channels 454A-454N. Additionally, each sample loading channel 454A-454N is in fluid communication with a different sample loading port 428A-428N. Two porous frits 438, 456 are disposed at either end of the sample loading channels 454A-454N. While the first frit 438 technically does not retain any packing material within the device, it may be fabricated from the same material as the second frit 456, which does retain packing material within the columns 439A-439N by way of several vias 457A-457N. To prepare the device 410 for sample loading, solvent flow is temporarily interrupted, an external gasketed interface (not shown) previously covering the sample loading ports 428A-428N is opened, and samples are supplied through the sample ports 428A-428N into the sample loading channels 454A-454N. The first and second frits 438, 456 provide a substantial fluidic impedance that prevents fluid flow through the frits 438, 456 at low pressures. This ensures that the samples remain isolated within the sample loading channels 454A-454N during the sample loading procedure. Following sample loading, the sample loading ports 428A-428N are again sealed (such as by using an external gasketed interface) and solvent flow is re-initiated to carry the samples onto the columns 439A-439N defined in the seventh layer 417.

While the bulk of the sample and solvent that is supplied to each column 439A-439N travels downstream through the columns 439A-439N, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 414B, a frit 436, a via 484A, a waste channel 485, vias 486A-486E, and through the waste port 486 to exit the device 410. The purpose of providing both an upstream and downstream path for each sample is to prevent undesirable cross-contamination from one separation run to the next, since this arrangement prevents a portion of a sample from residing in the sample loading channel during a first run and then commingling with another sample during a subsequent run.

2. Non-Laminated Devices

In further embodiments, pressure-driven separation devices including multiple separation columns suitable for performing parallel liquid chromatography may be fabricated in alternative formats to the laminated embodiments described previously. Non-laminated embodiments include both conventional-scale multi-column devices and microfluidic multi-column devices. For example, a multi-column fluidic device may be fabricated with various types and/or sizes of cylindrical tubing, including tubes having capillary dimensions, joined by a body structure. Preferably, the device materials slated to be in contact with samples and mobile phase solvents should be substantially inert and non-absorptive. Representative tube materials include metals such as stainless steels; silicon-bases substances such as quartz or various types of glass; and substantially inert polymers such as poly ether ether ketone. Alternatively, channel boundaries for containing stationary phase material may be formed directly within a body structure (such as by milling, molding, or other fabrication techniques known to one skilled in the art).

In one embodiment utilizing tubular columns, the tubes may be joined with at least one body structure permitting a rapid interface to a separate fluidic distribution manifold or network. For example, FIGS. 17A-17D illustrate separation device 830 fabricated with eight parallel tubes 832A-832N joined along each end with body elements 840, 845. Each tube 832A-832N has an inner bore 834A-834N for containing stationary phase material (not shown). If particulate-based stationary phase material is provided, the particles may be retained within the tube-based columns with liquid-permeable frits 835A-835N, 836A-836N disposed at either end of the tubes 832A-832N. In such an embodiment, the device 830 is packed with stationary phase when in a partially assembled state, such that frits (e.g., 835A-835N) along one end of the tubes 832A-832N are added following the packing step to retain the packing particulate material. The liquid-permeable frits 835A-835N, 836A-836N may be fabricated as discs or in other shapes using materials such as metallic screens, sintered ceramics, and/or porous (e.g., polymeric) membranes. While multiple discrete frits 835A-835N, 836A-836N are shown in FIGS. 17C-17D, frits spanning like ends of multiple columns are contemplated using materials resistant to lateral wicking such as track-etched polymeric membranes.

Preferably, each tube 832A-832N has two flared ends 831A-831N, 833A-833N adapted to press against the frit discs 835A-835N, 836A-836N and mate with corresponding inner recesses 842A-842N, 846A-846N in the body elements 840, 845 disposed at either end of the device 830. The flared ends 831A-831N, 833A-833N may be simply press-fit into these inner recesses 842A-842N, 846A-846N, or various sealing means including direct material attachment by conventional welding techniques (including ultrasonic welding), adhesive means, or further conventional mechanical techniques (e.g., clamps or screws) may be used. Alternatively, the body elements 840-845 may be cast or molded around the tubes 832A-832N.

Preferably, each body element 840, 845 includes a series of outer recesses 841A-841N or protrusions 847A-847N to mate with other external elements such as a fluidic distribution manifold 850 and a flow cell 870 such as illustrated in FIGS. 18A-18B. Such recesses 841A-841N and/or protrusions 847A-847N preferably each include an internal bore 844A-844N, 849A-849N for conducting liquid, and may be flared at least in part (as illustrated in FIGS. 17C-17D) to facilitate sealing engagement against one or more surfaces of external elements (e.g., the fluidic distribution manifold 850 and flow cell 870 illustrated in FIGS. 18A-18B).

While various external elements could mate with the device 830, typical examples are provided in FIGS. 18A-18B. A fluidic distribution manifold 850 includes an inlet tube 851 having an internal bore 852 leading to a 1:8 splitting network including multiple channel segments 853A-853B, 854A-854D, 855A-855N. Preferably, the manifold 850 may be clamped against the multi-column device 830 using moveable clamping means such as a pneumatic cylinder, a worm gear assembly, or equivalent means. Ultimately, fluid supplied to the inlet 851 is conveyed through eight protruding outlets 858A-858N into the multi-column separation device 830. The distribution manifold 850, which is preferably capable of being rapidly engage and disengage the separation device 830, may be used during packing and/or operation of the separation device 830. In operation of the device 830, the distribution manifold 850 preferably wets the columns 832A-832N with mobile phase solvent, and then is temporarily disengaged from the device 830 to permit samples to be added to the columns 832A-832N. For example, one or more manual or automated pipettors may be used to deposit a sample into the upstream recess 841A-841N of each column. Following sample loading, the distribution manifold 850 may re-engage the separation device 830 to drive the samples through the columns 832A-832N with additional mobile phase solvent. Alternatively, one or more conventional loop-type sample injection valves (not shown) may provided to accomplish sample loading either with or without fluidic distribution manifold (e.g., manifold 850 illustrated in FIGS. 18A-18B).

Following separation within the device 830, eluate is conveyed into a flow cell 870 to permit detection of the sample constituents. Preferably, the flow cell 870 includes a fluid inlet 872A-872N, a fluid outlet 873N, an light source (e.g., via fiber optic conduit) inlet 877A-877N, and detector outlet 878A-878N corresponding to each column 832A-832N of the separation device 830. Fluid conduits (e.g., 884A) and optical conduits (e.g., 882A) may mate with the flow cell 870 by way of threaded fittings 883A, 884A. Note that FIG. 18B illustrates only one fluid conduit 884A and one optical conduit 882A for clarity. Various detection means, including but not limited to UV-Visible detection, may be used to detect species within the eluate from each column. The flow cell 870 may further include apertures 871A-871N for anchoring or attachment purposes.

One advantage of integrating multiple columns 832A-832N with a body structure 840, 845 is that the resulting device 830 is volumetrically compact and permits rapid and relatively low-volume interfaces with external components. As noted previously, it would be desirable to link multiple columns to a common mobile phase source with a low volume conduit system (e.g., manifold 830) to facilitate more rapid separation. Additionally, it would be desirable to link multiple columns to one or more downstream detectors (e.g., flow cell 870) with low volume conduits to reduce undesirable band broadening of the separated species exiting the columns. Preferably, the aggregate volume (namely, void volume when containing packing material) of the column bores 834A-834N is substantially greater than the combined volume of the fluid flow paths (e.g., channels 853A-853B, 854A-854D, 855A-855N, 858A-858N) of the fluidic distribution manifold 830. Likewise, the aggregate volume of the column bores 834A-834N is substantially greater than the combined volume of the fluid flow paths (e.g., bores 849A-849N and portions of recesses 872A-872N open to fluid flow) between the columns 834A-834N and the detection region 873A-873N associated with each column 832A-832N. The aggregate void volume of the column bores 834A-834N preferably exceeds each of (a) the combined volume of the fluid flow paths of the distribution manifold 830 and (b) the combined volume of the fluid flow path between the columns 834A-834N and the detection regions 873A-873N by at least about three times; and more preferably by at least about six times.

In another embodiment, a multi-column device may be fabricated without tubes by defining channels within a block of material. Such a device 900 is illustrated in FIGS. 19A-19B. A block 902 defines nine channels 911A-911N to which stationary phase material may be added to form columns. If particulate stationary phase material is used, the particulate may be retained within the channels 911A-911N by frit materials 906, 908 disposed at either end of the block 902. The frits 906, 908 may be retained against the block 902 with end caps 902, 912 each defining fluid ports 904A-904N, 914A-914N corresponding to each column 911A-911N. The illustrated device 900 includes end caps 902, 912 having flat external surfaces that permit the device 900 to be rapidly coupled or decoupled with external devices such as by using gasketed interfaces. The device 900 is characterized by simplicity of manufacture and usage, with various column numbers and dimensions being contemplated.

D. Packing Apparatuses and Methods

Applicants have experimented with various methods and apparatuses for packing particulate-containing multi-column devices described herein. Descriptions of preferred apparatuses and methods for packing multi-column devices are provided below.

1. Clamping Apparatuses

Microfluidic devices such as the devices 100 or 610 may be placed within a clamping apparatus to assist with column packing. A first representative clamping apparatus is shown in FIGS. 5A-5F. The clamping apparatus includes a first (upper) plate 170 and a second (lower) plate 190. As shown in FIG. 5F, the two plates 170, 190 may be sandwiched around a microfluidic device (such as the device 100 described previously) and fastened with bolts 198. The upper plate 170 has through-holes 171A, 173A disposed along the sides of the plate 170 and designed to mate with corresponding (tapped) holes 171B, 173B in the lower plate 190 for accepting the bolts 198. To aid in aligning a microfluidic device between the two plates 170, 190, multiple raised pins 178 may be provided in the second plate 190 to penetrate apertures in a microfluidic device (e.g., holes 120, 121 in device 100) and mate with recesses 176 in the first plate 170. When the two plates 170, 190 sandwich a microfluidic device, the inner surfaces 174, 194 of the plates abut the device and face one another, with the outer surfaces 172, 192 of the plates 170, 190 facing outward.

Several features are provided to aid in interfacing the clamping apparatus with a microfluidic device to promote column packing. The first plate 170 defines a cutout region 180 that provides an unobstructed path for slurry to enter an inlet port such as the fluidic port 126 shown in FIG. 5E. The first plate 170 defines a recess 182 into which a gasket (not shown) is inserted; this gasket mates with the sample inlet ports 128A-128N during the packing step to prevent the entry of slurry into the ports 128A-128N. Further defined in the first plate 170 is a tapped recess 187 along one edge for accepting a high-pressure fitting (not shown) through which solvent separated from the packing slurry may exit the microfluidic device (e.g., device 100). The recess 187 includes an aperture or fluid passage 188 that connects to a second fluidic passage or recess 186 that penetrates the inner surface 174 of the first plate 170. The second fluidic passage 186 penetrates a surface 185 that is at approximately the same level as the bulk of the inner surface 174, but is raised in comparison to a surrounding annular recess 184 that is designed to hold an annular gasket (not shown). As shown in FIG. 5E, a fluidic port 130 of a microfluidic device 100 is designed to exhaust fluid (solvent) from the device 100 during the packing process into the fluidic passage 186 (and onward to passage 188 and an external fluid-conveying fitting leading to a conduit exiting the apparatus), such that the surface of the device 100 immediately surrounding the fluidic port 130 sealingly engages a gasket (not shown) contained in the annular recess 184 to avoid unintended fluid leakage. In this manner, the clamping apparatus including upper and lower plates 170, 190 facilitates the unobstructed entry of slurry into a microfluidic device 100, and provides for leak-free conduction of solvent separated from that slurry away from the microfluidic device 100.

Another representative clamping apparatus 299 is shown in FIGS. 6A-6B. The clamping apparatus includes a first plate 300 and a second plate 330. The clamping apparatus 299 is adapted to pack three microfluidic devices (such as the device 10 described previously) with stationary phase material; however, it will be readily apparent to one skilled in the art that clamping apparatuses for packing any desired number of devices may be provided by increasing or decreasing the size of the clamping device 299 and replicating the clamping device 299.

As shown in FIG. 6A, the two plates 300, 330 may be sandwiched around a microfluidic device 30A and fastened with bolts 340 and nuts 341. The first plate 300 has through-holes 302A, 304A disposed along the sides of the first plate 300 and designed to mate with corresponding holes 302B, 304B in the second plate 330 for accepting the bolts 340. To aid in aligning a microfluidic device 10A between the two plates 300, 330, multiple raised pins 308 may be provided in the first plate 300 to penetrate apertures (e.g., holes 20, 21 in device 10) in a microfluidic device and mate with recesses 306 in the second plate 330.

As before, several features are provided to aid in interfacing the clamping apparatus 299 with a microfluidic device 10 to promote column packing. The second plate 330 defines a slurry port 310 that provides an unobstructed path for slurry to enter an inlet port of the device 10. The first plate 300 defines a recess 312 into which a gasket 313 is inserted; this gasket 313 mates with the sample inlet port 328 of the microfluidic device 10 during packing to prevent the release of pressure during the packing process. Similarly, the first plate 300 defines a recess 314 into which a gasket 315 is inserted; this gasket 315 mates with the solvent inlet ports 22, 24 during the packing step to prevent the release of pressure during the packing process. As shown in FIGS. 6B, 7A, these features may be repeated to accommodate three (or even more) microfluidic devices 10A-10N (numbering for the features associated with the additional microfluidic devices 10 that may be secured by the clamping mechanism 299 are omitted for simplicity).

2. Slurry Packing Systems and Methods

Figure 5:
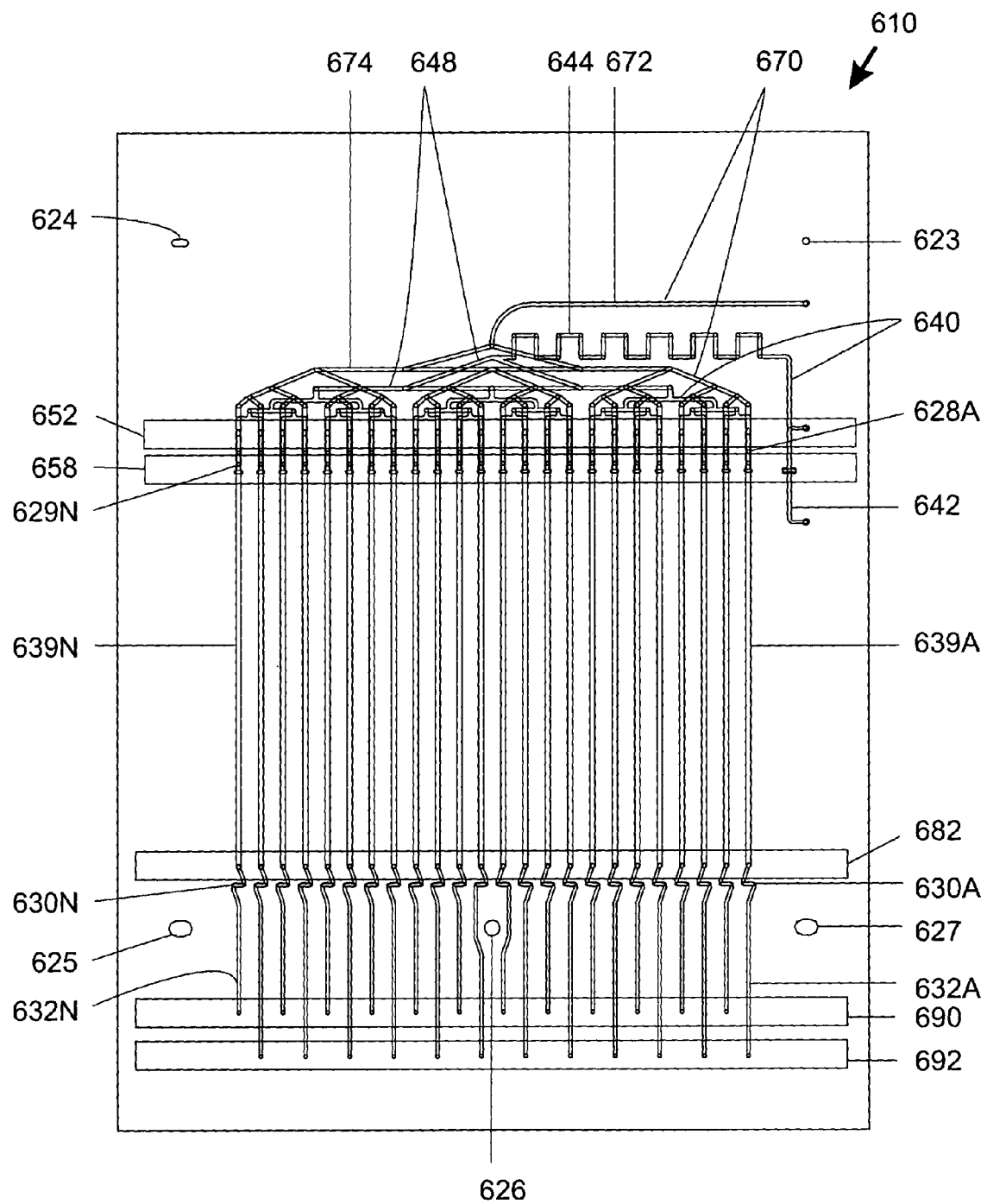
FIG. 5 is a top view of a first multi-layer microfluidic device containing twenty-four separation columns.
Figure 6D:
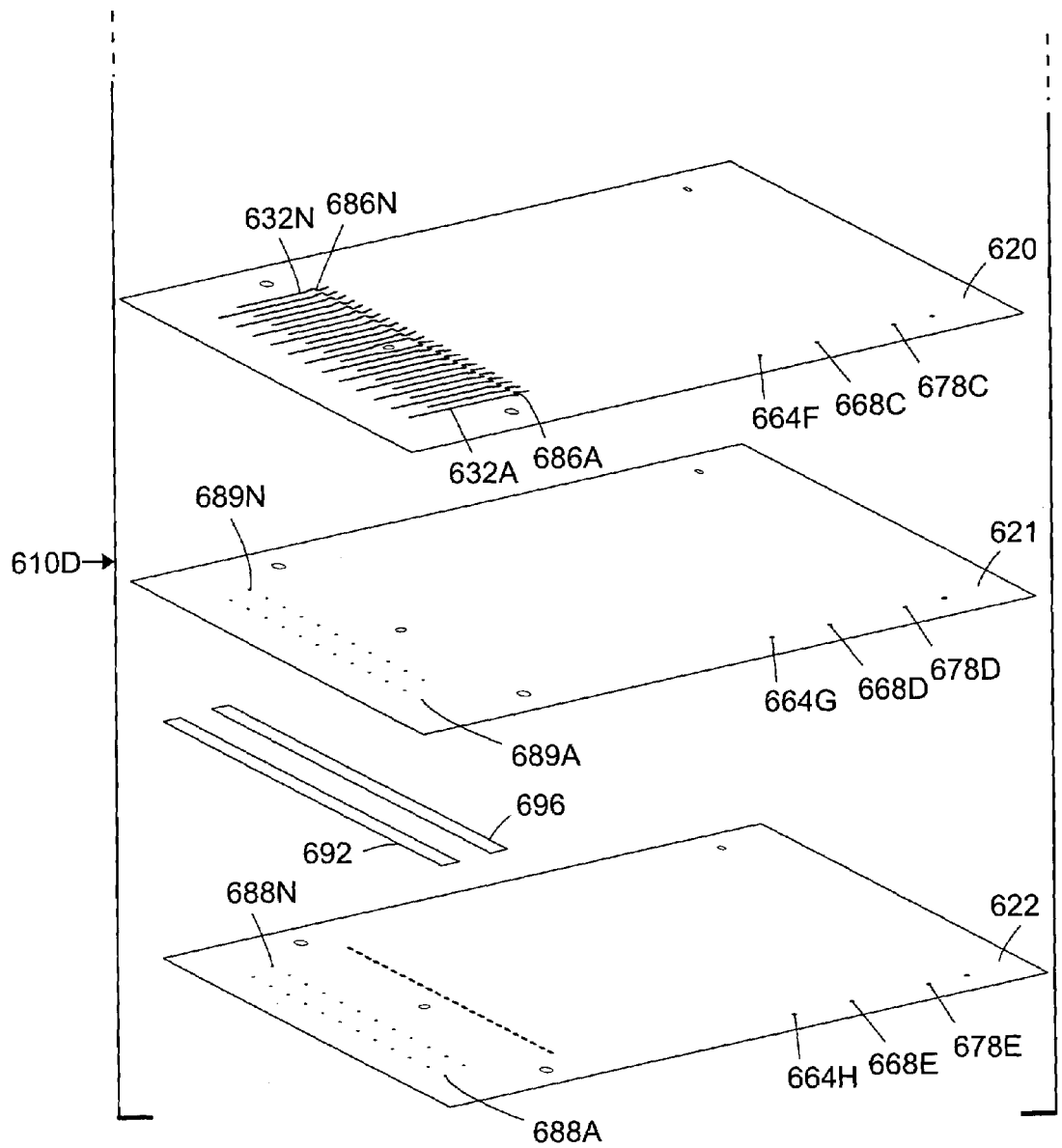
FIG. 6D is an exploded perspective view of a fourth portion, including the tenth through twelfth layers, of the microfluidic device shown in FIG. 5.
Figure 7:
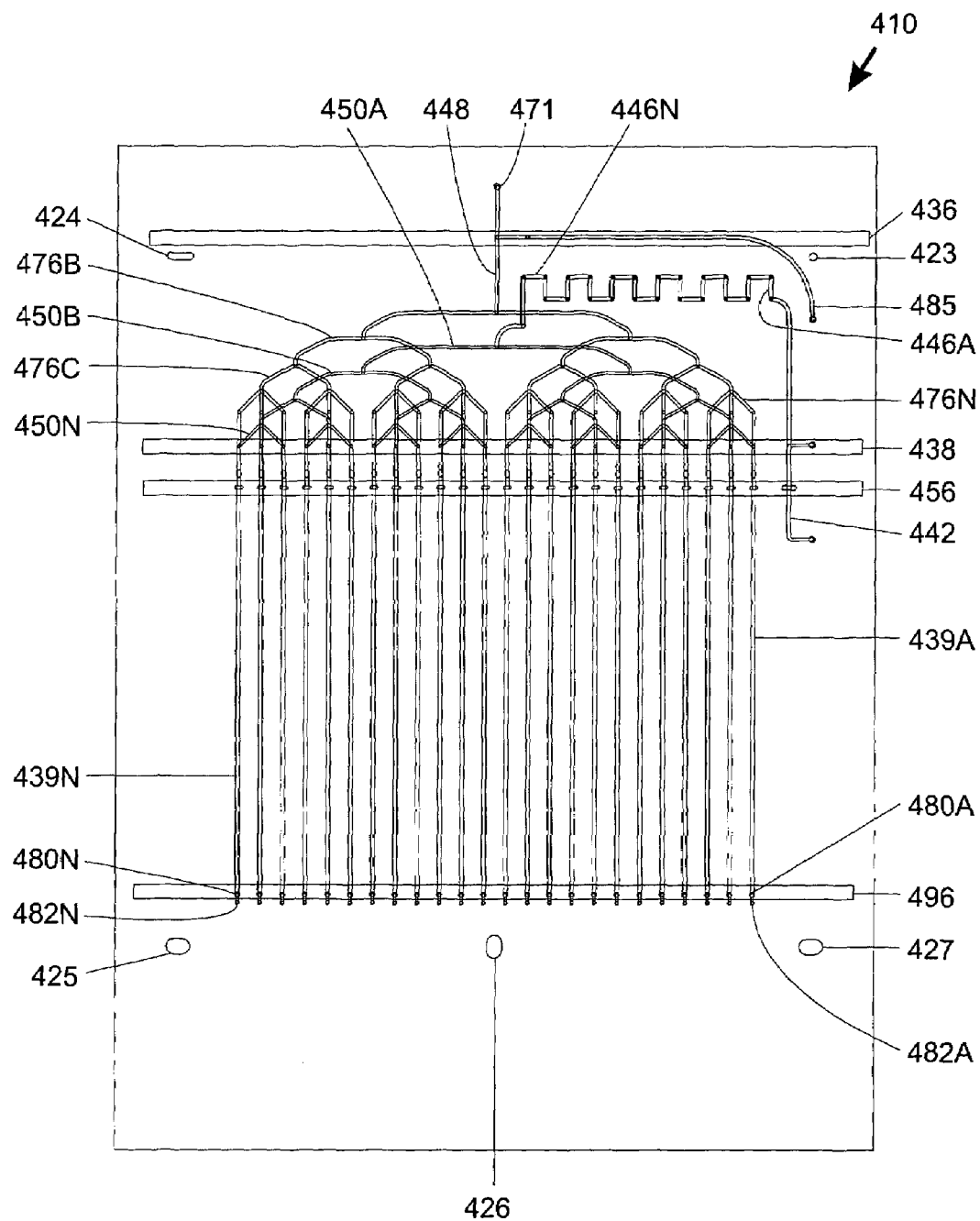
FIG. 7 is a top view of a second multi-layer microfluidic device containing twenty-four separation columns.

In a preferred embodiment, at least one fluidic device is slurry-packed using a pressure vessel. A system 200 that may be used to accomplish this result is shown in FIG. 5.

While only a single device 202 is illustrated as being contained within the vessel 210, multiple devices may be packed simultaneously within a pressure vessel according to methods disclosed herein. A pressure vessel 210 contains a slurry bath 208, with a fluidic device 202 placed therein such that a slurry inlet port 206 in the device 206 is fully immersed in the bath 208. The fluidic device 202 includes a fluidic connection 204 to provide a substantially leak-free connection to an external solvent collection device 216 that is preferably maintained at or below atmospheric pressure. When the pressure vessel is pressurized (by way of a pressure source 226, pressure regulator 228, and associated valving 230 and conduits, a pressure differential is created across the fluidic device 202 (by virtue of fluid connections to both pressure vessel 210 and the solvent collection device 216) that motivates slurry to flow from the slurry bath 208 into the device 202. Within the device 202, at least one frit (not shown) is preferably provided to retain particulate material from the slurry yet permit solvent to pass through to the solvent collector 216.

Preferably, operation of the system 200 is automated at least in part with controller 240. While various controller types may be used, the controller 240 is preferably microprocessor-based and is capable of executing software including a sequence of user-defined instructions. The controller 240 preferably interfaces with substantially all of the devices controlling inputs to and outputs from the pressure vessel 210. For example, the controller 240 may control the flow of slurry from a slurry supply reservoir or device 218 to the vessel 210 by operating a slurry supply valve 220. Preferably, slurry to be supplied to the vessel 210 is supplied under pressure at least above atmospheric pressure, utilizing means such as a pump or pressure supply (not shown) associated with the slurry supply device 218 to motivate slurry flow into the vessel 210. In a similar fashion, the controller 240 may control the flow of slurry from the vessel 210 to a slurry collection reservoir or device 222 by controlling a slurry exhaust valve 224. The slurry bath 208 may be stirred (preferably continuously) by way of a stirbar 212 located within the vessel 210, with motion of the stirbar 212 being motivated by a magnetic stirplate 214 having a connection to the controller 240.

As for pressurization of the vessel 210, the controller 240 may interface with a regulator 228 and valve 230 that control the supply of a pressurized gas (such as compressed nitrogen, for example) from a pressure source 226 to the vessel 210. The controller 240 preferably controls a throttling valve 232 having a connection to a vent 234 to permit controlled ventilation of the pressurized gas from the vessel 210 toward the conclusion of a packing process.

Applicants have successfully packed microfluidic devices according to the design of the device 10 disclosed herein with a simplified system (compared to the system 200) lacking automatic control. A ZipperClave® Model ZC0200SS02 pressure vessel (Autoclave Engineers, Erie, Pa.) having a detachable lid was modified to accept several fluid connections through the lid: a gas conduit, a slurry outlet, and a solvent outlet. The gas conduit was capable of providing regulated pressurized nitrogen from an external pressurized nitrogen canister, and also slowly exhausting pressurized nitrogen from the pressure vessel through a manually-operated needle valve. The slurry outlet included a long metal tube to extract slurry from near the bottom of the vessel; this outlet was connected to a manually operated external valve that could be opened to permit pressurized slurry to flow from the vessel. The solvent outlet was connected to a clamping apparatus according to that shown in FIGS. 4A-4F surrounding a microfluidic device 10 (illustrated in FIGS. 3A-3B), with a leak-free connection provided between the solvent outlet 30 and an external solvent collector provided by way of conventional threaded tubing and fittings. More specifically, the clamping apparatus (including first and second plates 100, 130) and clamped microfluidic device 10 were suspended in the vessel by way of the solvent outlet conduit such that the slurry inlet port 26 was disposed toward the bottom of the vessel and the solvent port 30 was disposed toward the vessel lid.

In the simplified system, the vessel was placed atop a magnetic stirplate (Corning model PC-353 stirrer) and a magnetic stirbar capable of being set in motion by the stirplate was placed into the vessel. A slurry was prepared by mixing 1.00 grams of Pinnacle II™ C-18 (silica) powder, 5 micron, catalog no. 551071 (Restek, Bellefonte, Pa.) with 500 mL of acetonitrile (MeCN) liquid. A portion of this slurry was manually added to the vessel to a sufficient level to submerge the slurry inlet port 26 of the microfluidic device 10 upon its addition to the vessel. Significantly, use of the rotating stirbar in the slurry ensures that slurry entering the microfluidic device is fully mixed up to the slurry inlet port, thus reducing the possibility of clogging at the inlet port. With fully mixed slurry entering the microfluidic device, it is anticipated that more concentrated slurries (i.e., slurries having relatively more particulate matter and relatively less solvent) can be used than are commonly employed in conventional slurry packing methods, thus permitting packing to be accomplished more quickly. Preferably, particles useful for packing fluidic devices disclosed herein and according to packing methods disclosed herein comprise silicon, zirconium, or polymeric materials. The use of frits renders unnecessary sintering processes, which are typically used to retain particles in a separation channel. The packed particles preferably comprise at least one surface functional group to permit the resulting devices to be used with high performance liquid chromatography methods. Examples of desirable surface functional groups include alkyl, cyano, amino, nitro, hydroxy, phenyl, phenyl-hexyl, and sulfonic acid.

With the vessel sealed, pressurized nitrogen was added to the vessel to motivate slurry to enter the microfluidic device 10 and flow toward the (low pressure) solvent outlet. The device 10 included a frit 51 that retained particulate within the device 10 but allowed solvent to pass therethrough to exit the device 10 through the fluidic port 30. Pressurized nitrogen was added to the vessel according to a six-step pressure ramp, with each step lasting about twenty minutes. The pressure was maintained at 200 psi (1379 kPa) for 20 minutes, and then ramped upward to 400, 600, 800, 1000, and 1200 psi (2758, 4137, 5516, 6895, and 8274 kPa) for the remaining pressure ramp steps. During application of the pressure ramp, solvent separated from the slurry flowed from the device 10 through fluidic port 30, then exited the vessel through the clamping apparatus and solvent outlet. The solvent was collected in a container having graduated markings. Monitoring progress of the column packing is a straightforward exercise if both the slurry makeup (proportion of particulate/solvent) and the volume of the fluidic structure to be packed with particulate are known. In this regard, it is helpful to monitor the accumulated solvent volume that has exited the device, the flow rate of solvent exiting the device, or both. Notably, a sudden drop in solvent flow rate exiting the device typically signals successful particulate packing of a specific fluidic volume using slurry packing methods disclosed herein. However, when the desired column volume is particularly small, then it may be more practical to monitor accumulated volume than flow rate. Feedback control of the pressure application (ramp) step based upon accumulated solvent volume or flow rate of solvent exiting a fluidic device is contemplated, as discussed in connection with FIG. 5.

Following application of the six-step pressure ramp, which lasted about two hours in total, a valve between the nitrogen supply pressure regulator and the vessel was closed. Then a slurry outlet valve was opened to permit the removal of (pressurized) slurry from near the bottom of the vessel. Once the slurry had been drained to a level well below the slurry inlet 26 of the device 10, taking care not to drop the pressure too quickly in the vessel, the slurry outlet valve was closed. Thereafter the needle valve was opened to allow the vessel to slowly depressurize to atmospheric pressure. This slow venting step has been accomplished in approximately 30-60 minutes. It is believed that slow venting assist in purging solvent and dissolved gas from the packed column(s), thus helping to prevent "blowback" of packing that would reduce its efficacy (i.e., "unpack" the particulate material). With the pressure fully vented from the vessel, the vessel was opened and the clamped device 10 was removed.

After completion of all packing steps, the slurry inlet port 26 may be sealed. One sealing method that has been successfully employed uses epoxy by first making a two-part epoxy mixture and then injecting the mixture into the slurry inlet port 26 until it reaches the trailing edge of particulate matter contained in the channel 38. Applicants have successfully used Devcon S-209 "5 minute fast drying epoxy" (ITW Devcon, Des Plaines, Ill.) for this task, although other equivalent sealing methods could be used. Sealing the packing material provides at least two advantages. First, it prevents the columns from un-packing. Second, sealing the slurry inlet port 26 and channel 38 limits the amount of flow of mobile phase or sample in an undesired direction (i.e., away from the outlet port 30).

Following initial slurry packing of a fluidic device but before a slurry inlet port is sealed, an optional further step to ensure tight packing of the columns may be employed. A pressurized fluid may be introduced into the slurry inlet port (e.g. port 26) and flowed through the column-containing channels (e.g., channels 45). Mobile phase solvent such as acetonitrile may be used for this purpose.

An alternative packing method and apparatus is capable of packing fluidic devices without the use of elevated pressures and pressure vessels. Instead, a pressure differential sufficient to motivate slurry to flow into a fluidic device (such as, for example, the device 10 described previously) may be generated by connecting a fluidic port 30 of such a device to a vacuum source such as a vacuum pump. If the slurry inlet port 26 of such a device 10 is submerged in an slurry bath at atmospheric pressure, then a pressure differential of nearly one atmosphere (101 kPa) can be developed across the device with the outlet connected to vacuum. Compared to the packing methods employing pressure vessels and highly elevated pressures, atmospheric pressure packing is anticipated to take a much longer time to yield packed columns with satisfactory results. On the other hand, atmospheric packing methods avoid volume limitations along with capital and operating expenses associated with pressure vessels. As a result, it is contemplated that an extremely large number of fluidic devices may be packed simultaneously in using an open, atmospheric trough containing a bath of stirred slurry. Each fluidic device may be connected to one or more vacuum sources by way of individual fluid conduits or a common vacuum manifold.

In yet another alternative packing method, pressurized slurry may be supplied to one or more fluidic devices having a solvent outlet vented to a low-pressure region such as atmosphere or vacuum. Preferably such a packing method is applied to one or more microfluidic devices having multiple columns in fluid communication at a common solvent outlet. A slurry supply manifold may be employed. In such an embodiment, however, where pressurized slurry is routed via fluid conduit to a slurry inlet (rather than using a slurry bath), it is difficult to ensure that completely stirred slurry is provided to the devices.

In another embodiment, a rotatable pressurized vessel may be used. For example, referring to FIGS. 7A-7C, one embodiment of a multicolumn packing system 500 according to the present invention utilizes ultrasonic energy and a rotatable pressurized vessel 502 to deliver slurry to one or more microfluidic devices 10A-10N. The system 500 comprises a sampling vessel 502, a pressure source 504, a rotary actuator 506, a plurality of slurry delivery conduits 508A-508N, and an ultrasonic bath 510.

The sampling vessel 502 may be any suitable cylindrical vessel capable of containing the pressures required for the packing process. In the embodiment illustrated in FIGS. 7A-7C, the sampling vessel 502 is a 8" long×2" outside diameter, 0.3 liter stainless steel vessel with hemispherical ends (SS-DOT sample cylinder, Hoke Inc., Clifton, N.J.). The sampling vessel 502 is suspended in a horizontal position and rotatably (and preferably, removably) mounted to a frame (not shown) using brass bushings suspended in fixed collars (or, alternatively, bearings) at either end or any other suitable rotatable mounting mechanism. A fluidic connection 516 to the sampling vessel 502 is permitted through at least one end bushing. The sampling vessel 502 and associated slurry delivery conduits 508A-508N (leading to one or more microfluidic devices 10A-10N) may be rotated through a range of about ninety degrees (as shown in FIGS. 7B-7C), preferably by way of actuating means 506, such as a rotary actuator, a linear actuator with an appropriate linkage, or another suitable actuator. Preferably, a programmable controller 507 is coupled to the actuating means 506 to control periodic rotation of the sampling vessel 502.

A solvent 512 (such as acetonitrile) and particulate 518 (such as C-18 silica particles) are contained in the sampling vessel 502. Because the sampling vessel 502 is suspended horizontally, the contents are gravitationally stratified along the length of the sampling vessel 502. Referring to FIG. 7B, when the sampling vessel 512 is disposed in an "un-rotated" (0 degrees) position with the slurry delivery conduits 508A-508N positioned horizontally, the level of the particulate material 518 within the sampling vessel 502 is below the level of the slurry delivery conduits 508A-508N, so only solvent 512 is supplied through the slurry delivery conduits 508A-508N to the microfluidic device(s) disposed and fluidically coupled below (as shown in FIG. 7A). Referring to FIG. 7C, when the sampling vessel 502 is disposed in a rotated (e.g., 90 degrees) position, however, the slurry delivery conduits 508A-508N are positioned at the bottom of the sampling vessel 502, below the level of the particulate 518 within the sampling vessel 502, so particulate 518 (along with solvent 512) is supplied to the microfluidic device(s) below (not shown, see FIG. 7A). Referring again to FIG. 7A, a pressure source 504, such as a Shimadzu LC-10AT pump (Shimadzu Scientific Instruments, Inc., Columbia, Md.) or other suitable pressure source, aided by gravity, provides the flow velocity to carry the particulate 518 from the sampling vessel 502 into the slurry delivery conduits 508A-508N. Preferably, a tube oscillator 520 (e.g., each comprising a motor, such as a small 3600 RPM motor, having an offset cam) is affixed to each slurry delivery conduit 508A-508N to vibrate the particulate 518 within each slurry delivery conduit 508A-508N to break up any possible particle clumps, thus reducing the chance of blockage further downstream. Preferably, the slurry delivery conduits 508A-508N include at least portions that are flexible to accommodate rotation of the sampling vessel 502 through at least about a ninety degree range.

Each microfluidic device 10A-10N to be packed includes porous frits 40, 50, 51 adapted to retain the particulate material 518 within the microfluidic device 10A-10N (see FIG. 3A). To this end, the pore size of the frit material should be smaller than the size of the particulate 518 to be packed within the microfluidic devices 10A-10N. While various frit materials may be used, one preferred frit material is one mil (25 micron) thickness Celgard 2500 membrane (55% porosity, 0.209×0.054 micron pore size, Celgard Inc., Charlotte, N.C.). As solvent 512 and particulate material 518 are provided to each microfluidic device 10A-10N, the solvent 512 preferably flows through the frits 40, 50, 51 and exits the microfluidic devices 10A-10N, while the particulate material is retained within each microfluidic device 10A-10N by the frits 40, 50, 51. Upon entering each microfluidic device 10A-10N, the particulate material 518 settles down to the bottom of the columns 45 to be packed. Having each microfluidic device 10A-10N at least partially immersed in an ultrasonic bath 510 helps to break up any potential particulate blockages within each microfluidic device 10A-10N and helps to facilitate dense packing. The process of rotating the sampling vessel 502 is preferably repeated approximately ten to fifteen times, with five to ten second dwell times for supplying particles to the slurry delivery conduits 508A-508N, and sixty to ninety second dwell times for supplying only solvent to the slurry delivery conduits 508A-508N.

In a preferred embodiment, multiple microfluidic devices 10A-10N are packed simultaneously by way of multiple slurry delivery conduits 508A-508N emanating from the sampling vessel. FIGS. 6A-6B, 7A-7C illustrate a system and apparatus for the simultaneous packing of three microfluidic devices 10A-10N, but scaling up to simultaneously pack a much greater number of microfluidic devices 10A-10N is a relatively simple matter of providing a solvent vessel 502 of appropriate dimensions, providing an appropriate number of slurry delivery conduits 508A-508N from the sampling vessel, providing a clamping mechanism 99 adapted to secure the desired number of microfluidic devices 10A-10N, ensuring appropriate solvent flow (e.g., by larger and/or additional pumps if necessary), and providing an ultrasonic bath 510 of appropriate size/volume.

Referring to FIG. 7A, three microfluidic devices 10A-10N may be packed using the above-described components. First, approximately 80 grams of particulate 518 (in this case, Microsorb C-18 silica) is supplied to the sampling vessel 502 at one end of the cylinder—preferably the end to which the pressure source 504 connects to prevent particles from entering the pump inlet tubing 505. The addition of particulate 518 to the sampling vessel 502 is aided by wetting the particles first with solvent 512 (in this case, 100% tech grade acetonitrile). After all of the particulate 518 is added to the sampling vessel 502, the sampling vessel 502 is filled with solvent 512 (again, 100% tech grade acetonitrile). It is believed that minimizing the presence of air within the sampling vessel 502 is beneficial to avoid an unduly slow pressure ramp when the pressure source 504 is activated during the packing procedure—since the pressure source 504 will compress any air within the sampling vessel 502. Once the sampling vessel 502 is filled with particulate 518 and solvent 512, the pressure source 504 (an HPLC pump) is activated to fill the inlet tube 505 with solvent 518 so as to eliminate air in the inlet tube 505. When the inlet tube 505 is filled, the inlet tube 505 is attached to the vessel with an appropriate leak-free connection (in this case, a stainless steel NPT to ⅛" OD tubing connection). It is recommended to minimize the presence of air in the vessel and associated tubing.

The sampling vessel 502 is then coupled to an actuator 506 capable of rotating the sampling vessel 502 through a ninety degree rotation range and capable of dwelling at each of the zero degree and ninety degree positions for user-defined intervals. As the sampling vessel 502 is coupled to the actuator 506, care should be taken to prevent particulate material from falling into the slurry delivery conduits 508A-508N, since such an event could cause the slurry delivery conduits 508A-508N connections to become clogged during packing. The slurry delivery conduits 508A-508N comprise first tubes emanating from the vessel 502, the first tubes being approximately twelve inch long sections of ⅛" OD×¹⁄₁₆" ID flexible tubing able to withstand at least 1000 psi (6.9 MPa). Each of these tube sections are connected to smaller ID tube sections (each approximately 6 inches long with ¹⁄₁₆" OD×0.005" ID) with appropriate connectors, such as Upchurch superflangless connectors and union connectors. Both ends of the smaller tubing each have another connector (e.g., Upchurch superflangless connectors), one of which connected to the Upchurch union connector and the other of which connected directly to the packing inlet of the clamping mechanism 99, to deliver slurry to the microfluidic devices 10A-10N suspended therein.

Each microfluidic device 10A-10N is disposed at least partially within the ultrasonic water bath 510 to permit direct contact between each device 10A-10N and the sonication fluid (e.g., water). An ultrasonic bath 510 is merely one example of a mechanism for vibrating, agitating, or otherwise adding energy to each device 10A-10N to promote denser packing. A portion of each device 10A-10N is suspended approximately 0.25 inches deep in the ultrasonic bath 510. One example of such an ultrasonic bath 510 is a Branson Model 8500 (Branson Ultrasonics Corp., Danbury, Conn.), which is maintained during the packing procedure at a 50% power setting with the frequency/transducer sweep turned on.

With the sampling vessel 502 filled and appropriately connected to the microfluidic devices 10A-10N, the solvent (e.g., HPLC) pump 504 is activated to initiate constant flow rate of one ml/min to verify that the pressure ramping starts within about five seconds. If the pressure ramp does not start within this interval, this typically indicates the presence of an air pocket in the vessel or tubing that can detrimentally affect packing efficiency. When the system is determined to be substantially free of air pockets, packing is initiated. The ultrasonic bath 510 and tube oscillators 520A-520N are activated, and the packing sequence (including multiple steps of alternating the supply of particulate 518 and the supply of solvent 512 to the microfluidic devices 10A-10N by rotating the sampling vessel 502) is initiated. Table 1 indicates the dumping times and dwell times according to a preferred embodiment.

TABLE 1

Dumping and dwell times for packing of microfluidic devices.

| Step | Rotation Angle (degrees) | Dwell Time (secs) |
|---|---|---|
| 1 | 90 | 5 |
| 2 | 0 | 30 |
| 3 | 90 | 5 |
| 4 | 0 | 30 |
| 5 | 90 | 5 |
| 6 | 0 | 30 |
| 7 | 90 | 5 |
| 8 | 0 | 30 |
| 9 | 90 | 5 |
| 10 | 0 | 30 |
| 11 | 90 | 5 |
| 12 | 0 | 30 |
| 13 | 90 | 5 |
| 14 | 0 | 30 |
| 15 | 90 | 5 |
| 16 | 0 | 30 |
| 17 | 90 | 5 |
| 18 | 0 | 30 |
| 19 | 90 | 5 |
| 20 | 0 | 30 |
| 21 | 90 | 5 |
| 22 | 0 | 30 |
| 23 | 90 | 5 |
| 24 | 0 | 30 |
| 25 | 90 | 5 |
| 26 | 0 | 300 |

This combination of process steps for purposes of illustration; other combinations of dump time and dwell time may be used.

To prevent rupture of the microfluidic devices 10A-10N and provide repeatably dense column packing, a pressure sensor (not shown) in sensory communication with the solvent supply system is preferably provided and connected to a controller 507 to maintain the supply pressure within a desired range. Preferably, the controller 507 receives user-defined settings for minimum and maximum pressure and controls activation of the pressure source 504 to maintain the solvent supply pressure within a desired range (e.g., between 270-300 psi/1860-2070 kPa). If the pressure source 504 is set to supply a constant flow rate, it may be periodically activated and deactivated to maintain pressure within the desired range. Alternatively, a pressure regulator (not shown) may be supplied between the pressure source 504 and the sampling vessel 502 to regulate the supply pressure. Also, sudden and/or large changes in system pressure may indicate a problem with the packing process, such as clogging within or burst of one of the microfluidic devices 10A-10N. Individual pressure sensors (not shown) may monitor the pressure within each of the slurry delivery conduits 508A-508N to allow the determination of which microfluidic device 10A-10N is the source of the pressure change. Valves (not shown) also may be included in each of the slurry delivery conduits 508A-508N to allow selective closure of the slurry delivery conduits 508A-508N to remove the problematic microfluidic device 10A-10N from the system. The controller 507 may then adjust the pressure and flow rates to reflect the change in the number of microfluidic device 10A-10N being packed.

Upon completion of the last step (e.g., 26th step), the ultrasonic bath 510 and the tube oscillators 520A-520N are deactivated, and the (packed) microfluidic devices 10A-10N are removed from the ultrasonic water bath 510.

In another embodiment, a relatively dilute or "thin" slurry (i.e., having a high concentration of solvent and a low concentration of particulate matter) may be used. It is believed that thin slurries help promote more densely packed separation channels by providing a slow buildup of particles within the columns. It is also believed that thin slurries help avoid problems with particulate clogging the packing components. One difficulty, however, in trying to utilize thin slurries of particulate matter not soluble in the accompanying solvent is that the particulate tends to settle downward due to the force of gravity. As will be recognized by one skilled in the art, there exist numerous ways to agitate or otherwise add energy to a solvent/particulate mixture to distribute particulate within the solvent. Several examples of systems for providing thin slurries to separation devices to pack separation channels follow.

In one embodiment, particulate is agitated by manual action to maintain a sufficient amount of particulate entrained in a solvent. For example, referring to FIG. 10, a column packing system 700 includes a pressure vessel 712 containing particulate material 714 and (liquid) solvent 716. (While FIG. 10 illustrates a sharp line between the particulate material 714 and the solvent 716, during operation of the system 700 the bulk of the particulate material 714 is preferably substantially dispersed within the solvent volume). A solvent pump 702 supplies pressurized solvent from a solvent reservoir (not shown) to the pressure vessel 712 by way of tubing 703 and a solvent inlet 704 having a threaded fitting. Slurry is supplied from the pressure vessel 712 to at least one fluidic device 710 through a slurry outlet 706, tubing 707, and a fitting 708 preferably engaged to a clamping apparatus (such as described previously herein) providing a pressure-tight connection to the at least one fluidic device 710. Preferably, valves (not shown) are provided in fluid communication with the tubing 703, 707. The fluidic device 710 is preferably at least partially immersed in a liquid 722 contained by a (ultrasonic) sonicator bath 720. During operation of the system 700, the vessel 712 is preferably shaken and/or periodically impacted (such as with a hammer) to maintain a sufficient amount of particulate distributed within the solvent.

In one packing method utilizing the system 700, 14 grams of Luna 10 micron C-18 chromatographic stationary phase particulate material (Phenomenex Inc., Torrance, Calif.) were added to approximately 100 ml of HPLC grade isopropyl alcohol ("IPA") (Fisher Scientific, Pittsburgh, Pa.) in a flask and the combination was sonicated in a water bath in an open sonicator (Branson Model 8500, Branson Ultrasonics Corp., Danbury, Conn.) for approximately 5 minutes. The resulting wetted slurry was supplied through a funnel to a 0.3 liter stainless steel cylindrical vessel 712 with hemispherical ends (SS-DOT sample cylinder, Hoke Inc., Clifton, N.J.). The slurry-containing cylinder 712 was then filled until overflowing with additional HPLC grade IPA 716 to displace air from the cylinder 712. A Shimadzu LC-10AT HPLC pump (Shimadzu Scientific Instruments, Inc., Columbia, Md.) was connected via 1/16" OD flexible polytetrafluoroethylene tubing 703 to one end of the cylinder 712, and a packing manifold (similar to the apparatus 299 shown in FIGS. 6A-6B) clamped around a microfluidic device 710 (containing twenty-four separation channel according to the design of the device 610 illustrated in FIGS. 8, 9A-9E) was connected to the other end of the cylinder 712 using the tubing 707 of the same type as the other tubing 703. The packing manifold and a portion of the microfluidic device were immersed in a water-filled bath 722 of an open sonicator 720 (Fisher model FS30, Fisher Scientific, Pittsburgh, Pa.). The downstream end of the microfluidic device 710 was exposed to air. The suction side of the HPLC pump 702 was connected to a reservoir (not shown) of HPLC grade IPA. Upon connecting the components, the cylindrical vessel 712 was oriented in a horizontal position, the sonicator 720 was activated, and the HPLC pump 702 was activated and set to a constant pressure of 150 psi (1030 kPa) to supply slurry to the microfluidic device 710. Approximately once every five minutes, the cylindrical vessel 712 was manually rotated into a vertical position, manually impacted roughly 10 times with a 1-lb (0.45 kg) dead blow hammer, then rotated 180 degrees into the opposing vertical position and manually impacted roughly another 10 times with the hammer, and then returned to a horizontal position. It is believed that the preceding rotation and impacting steps functioned to loosen particles 714 that had settled along the lower portion of the cylinder wall and distribute them back into the liquid 716. The microfluidic device 710 was partially filled under these conditions until about 1 inch of packing material was present in the least packed separation channel of the device 710. After that, the pressure of the pump 712 was increased to 350 psi (2410 kPa), still continuing the periodic rotation and impacting steps, until substantially all of the microfluidic channels upstream of the frits were filled with particulate stationary phase material. The microfluidic device 710 and manifold were then removed from the sonicator bath 720, a valve (not shown) disposed between the microfluidic device 710 and the cylinder 712 was closed, and the pump 702 was de-activated. The microfluidic device 710 was left within the manifold for approximately five minutes to permit pressure to escape through the downstream end of the microfluidic device 710 before disengaging the microfluidic device 710 from the manifold.

The resulting packed device 710 had column lengths of about 8 cm. When Luna C18 15 micron chromatographic stationary phase particulate material (Phenomenex Inc., Torrance, Calif.) was used to pack the columns, and the device 710 was operated to perform high performance liquid chromatography at greater than 450 psi (3100 kPa) and a mobile phase flow rate of about 15 microliters per minute per column, separation efficiencies of about 400 theoretical plates (ASTM) were obtained for each column, which translates into a per unit length efficiency of about 5,400 plates per meter. Even greater efficiencies can be obtained using smaller packing material, and by manipulating the mobile phase flow rate.

Figure 11:
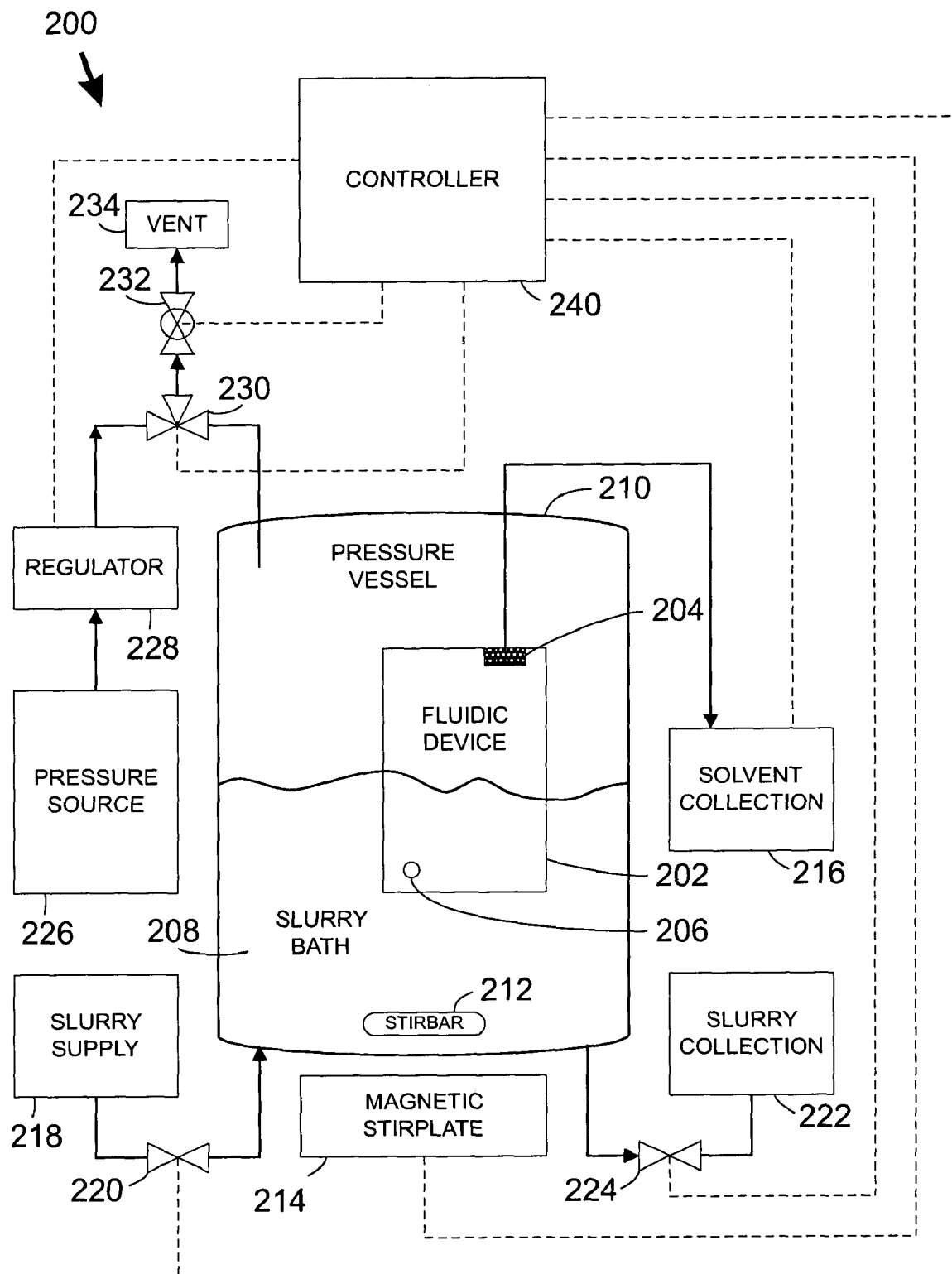
FIG. 11 is a schematic illustration of a system and apparatus for packing at least one separation column.

Another column packing system 730 is illustrated in FIG. 11. This system 730 is similar to the system 700 illustrated in FIG. 10, but includes a mechanical stirring mechanism. The system 730 includes a pressure vessel 742 containing particulate material 744 and (liquid) solvent 746. A solvent pump 732 supplies pressurized solvent from a solvent reservoir (not shown) to the pressure vessel 742 by way of tubing 733 and a solvent inlet 734 having a threaded fitting. An impeller 748 within the vessel 742 is coupled to an external motor 743 by way of a shaft 747. A pressure-tight fitting 738 permits the impeller to be operated while the pressure vessel 742 is pressurized. Slurry is supplied from the pressure vessel 742 to at least one fluidic device 740 through a slurry outlet 736, tubing 737, and a fitting 738 preferably engaged to a clamping apparatus (such as described previously herein) providing a pressure-tight connection to the at least one fluidic device 740. Preferably, valves (not shown) are provided in fluid communication with the tubing 733, 737. The fluidic device 740 is preferably at least partially immersed in a liquid 752 contained by a (ultrasonic) sonicator bath 750. During operation of the system 730, the impeller 748 is rotated by the motor 743 and shaft 747 to maintain a sufficient amount of particulate 744 distributed within the solvent 746. A diluted mixture of entrained particles is supplied to the microfluidic device(s) 740 to permit a slow, dense buildup of particles within the separation channels contained in the device(s) 740.

Figure 12A:
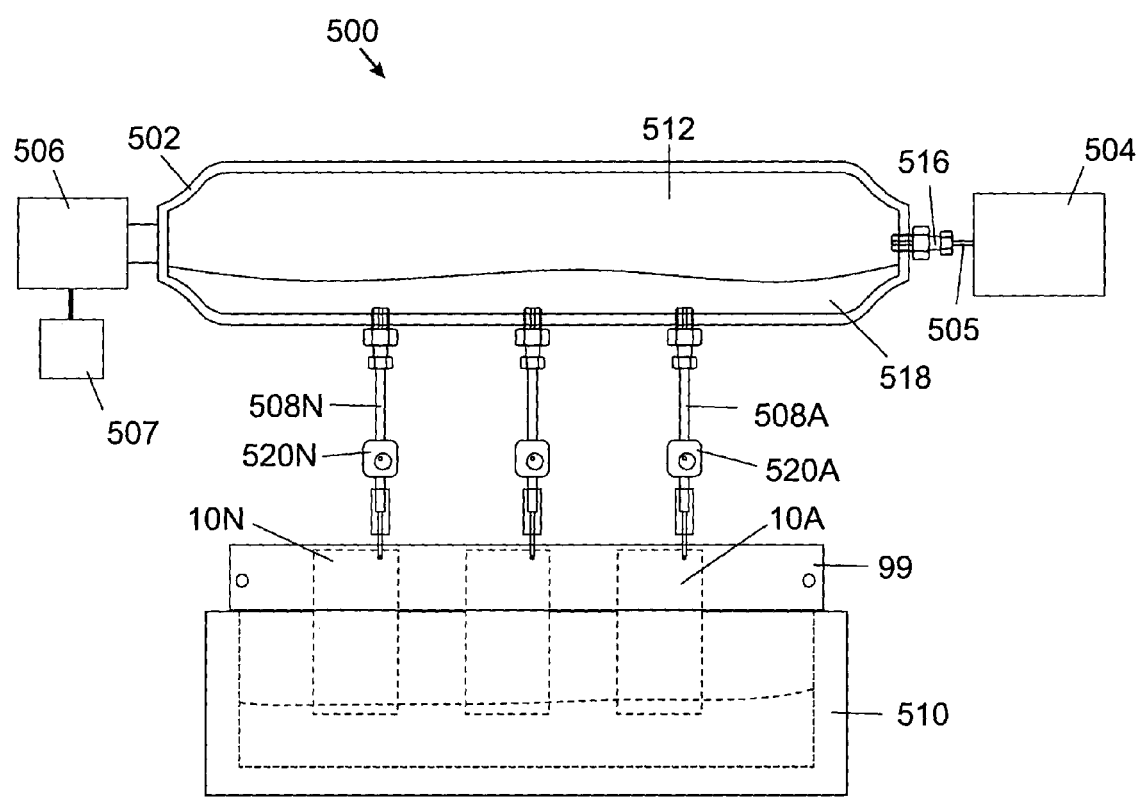
FIG. 12A is a schematic illustration of a system utilizing a rotatable cylinder for packing at least one separation column.

A further column packing system 760 is illustrated in FIG. 12. This system 760 is similar to systems described previously herein, but rather than relying upon agitation of particulate within a pressure vessel, the system 760 permits slow addition of particulate to a flow of solvent. The system 760 includes a reservoir 772 containing particulate material 774 and (preferably) solvent 746 to displace air from the reservoir. The reservoir 772 has a cap 771 on one end. The bottom of the reservoir 772 includes a particulate outlet 764 that connects to a tee 778. A solvent pump 762 supplies pressurized solvent from a solvent reservoir (not shown) through the tee 778. Particles from the reservoir 772 slowly "spill" out of the vessel into the solvent stream as it passes through the tee 778. Particulate 774 can be forced out of the reservoir 772 by reducing the pressure in the solvent stream (e.g., by deactivating and quickly reactivating the pump 762, or opening a valve (not shown) to release some pressure, etc.). The resulting mixture formed in the tee 778 flows through tubing 767 and a fitting 768 preferably engaged to a clamping apparatus (such as described previously herein) providing a pressure-tight connection to at least one fluidic device 770. The flow rate of the solvent supplied by the pump 762 may be adjusted, and/or the size of the orifice between the reservoir 772 and the tee 778 may be adjusted, to alter the proportion of particulate material to solvent supplied to the fluidic device(s) 770. In one embodiment, a valve (not shown) may be placed between the reservoir 772 and the tee 778 to control the flow of particulate into the tee 778. The fluidic device(s) 770 are preferably at least partially immersed in a liquid 782 contained by a (ultrasonic) sonicator bath 780. A diluted slurry is supplied to the microfluidic device(s) 770 to permit a slow, dense buildup of particles within the separation channels contained in the device(s) 770.

Yet another column packing system 800 is illustrated in FIG. 13. This fluidized bed design utilizes a vertically disposed vessel 812 containing solvent 816 and particulate 814. Solvent 816 is supplied from a pump 802 via tubing 803 to an inlet 804 disposed at the bottom of the vessel 812. Vertical flow of the solvent 816 supplied by the pump 802 agitates particulate within the vessel 812, thus ensuring that a sufficient amount of particulate 814 becomes entrained in the solvent 816 before exiting the vessel 812 through an outlet 806. One or more baffles (not shown) may be disposed within the vessel 812 above the inlet 804 to improve agitation of the particulate 814. Further factors affecting entrainment include the size of the particulate 814 used, the dimensions of the vessel 812, and the flow rate of the solvent 816 supplied by the pump 802. Slurry is supplied from the vessel 812 to at least one fluidic device 810 through a slurry outlet 806, tubing 807, and a fitting 808 preferably engaged to a clamping apparatus (such as described previously herein) providing a pressure-tight connection to the fluidic device(s) 810. Preferably, valves (not shown) are provided in fluid communication with the tubing 803, 807. The fluidic device 810 is preferably at least partially immersed in a liquid 822 contained by a (ultrasonic) sonicator bath 820. During operation of the system 800, a diluted slurry is supplied to the microfluidic device(s) 810 to permit a slow, dense buildup of particles within the separation channels contained in the device(s) 810.

As compared to conventional methods for packing individual chromatography columns, methods according to the present invention permit much larger number of columns (including both multi-column microfluidic devices and multiple microfluidic devices) to be packed simultaneously. It is believed that the packing methods and apparatuses disclosed herein permit much higher packing throughput and may be scaled to facilitate large production volumes at a modest capital cost. As compared to other methods for packing separation columns, the present methods greatly speed up packing time and are much more scalable to large production volumes.

E. Preferred Multi-Column Devices with Monolithic Columns

In another embodiment, multi-column devices can be fabricated with monolithic columns. In particular, such devices can be fabricated using polymeric channel-defining materials. Fabrication of monolithic columns in glass channel-defining materials is known; however, there are limitations to using glass for chromatographic separations. For example, it can be difficult to provide robust fluidic couplers that mate with glass tubes, and glass is known to be fragile due to its brittleness. Additionally, glass is not well suited for use with fluids characterized by extremes in pH (namely, very acidic or very basic solutions).

One of the challenges with fabricating monolithic columns in polymeric devices is ensuring that analyte flows predominantly through, rather than around, the monolith, particularly in polymeric materials characterized by low surface energy. This is particularly important for performing pressure-driven separation, since the large pressure drop through the column (on the order of tens to hundreds of psi or more) tends to dislodge a monolith from the surrounding channel wall and cause the monolith to move with the direction of fluid flow within the device. To overcome these challenges, Applicants have found that devices having multiple monolithic columns can be fabricated in polymeric materials by activating the polymeric surfaces bounding the columns. This activation can be performed by various means including plasma, chemical, electromagnetic and/or radiation. Following surface activation, an elevated number of reactive surface groups are formed along the polymeric surface, thus permitting a monolith to 'anchor' onto the activated surface. This ensures that bulk analyte flows through—rather than around—the columns, thus rendering the monolithic suitable for performing pressure-driven chromatography.

As compared with particulate-based columns, one advantage of using monolithic columns is that frits are not required to retain the columns within a device. The avoidance of frits has the potential to simplify device design and fabrication. Another potential advantage of monolithic columns is that they can provide greater separation efficiency than packed columns. This can permit separations to be performed more quickly than using packed particulate-based columns, or at lower pressures to achieve comparable results.

Fabrication of multiple monolithic columns within a single fluidic device promotes efficiency in both fabrication and operation. Surface treatment steps can be performed simultaneously on multiple columns, just as monolithic column fabrication steps can be performed in parallel. This promotes more rapid fabrication on a per-column basis. Likewise, the integration of multiple monolithic columns into a single device having a common body structure ensures that columns fabricated according to substantially identical conditions are used together to promote reproducible separation results in a column-to-column basis.

Monolithic columns can be substituted for particulate-based columns in many, if not all, of the foregoing device embodiments. The design of such devices may be simplified by omitting frits, which may be rendered unnecessary by anchoring the monoliths sufficiently to the surrounding channel surfaces.

1. Surface Treatment

Ideally, materials used to fabricate chromatographic separation devices should be substantially inert to avoid potential interactions between analytes and the materials with which the separation devices are formed. Additionally, to avoid misleading results, the device materials should resist both adsorption and absorption of analytes and mobile phase solvents. Unfortunately, it is inherently difficult to form chemical or other bonds to typically low surface energy polymeric materials that meet the foregoing criteria. Examples of materials having properties that would be desirable for use in chromatography, but have low surface energies rendering them substantially non-reactive, include fluoropolymers (e.g., polytetrafluoroethylene), polyolefins (e.g., polypropylene and polyethylene). Additional substantially non-reactive materials such as poly ether ether ketone ("PEEK") could be used.

To promote bonding between monoliths and low surface energy channel- or conduit-defining polymers, one or more surfaces of the polymers are preferably surface treated before the precursor materials for the monoliths are added to the device. Preferable surface treatment methods include corona discharge, flame treatment, vacuum plasma (e.g., utilizing nitrogen and/or oxygen); ammonia plasma; air plasma (using atmospheric air); fluorination, infrared laser (2% carbon black) treatment; AgII electrolysis; and chromic acid treatment. Multiple treatment methods may be used if desired.

Gas phase plasma (an electrically neutral mixture of electrons, ions, radicals, photons, recombinant products, and neutrals created by the application of energy such as radio frequency (RF) to a source gas contained within a vacuum chamber) is particularly preferred since it is capable of rapid action. In one embodiment, a polymeric material (e.g., a polyolefin) is treated with an air feed gas at 0.2-0.4 Torr, RF energy density from 0.01 to 1.0 W/cm$^2$, and treatment time from 30 seconds to 15 minutes.

Each of the foregoing methods may provide different degrees of surface modification. The intent is to create different functional groups on the surface of a polymer to modify the chemical activity of the surface. The new functional groups have strong chemical bonds with the bulk material and have the capability to further bond with a monolith in contact with the activated surface.

Notably, surface treatment methods may be applied to raw materials for fabricating a device (e.g., raw polymeric tubes or polymeric sheets) or to an assembled device. For example, plasma may be flowed into the channels or conduits of a polymeric device following its assembly. Since certain surface treatment methods have a limited temporal effect, however, it is often desirable to add and bond monoliths into the separation device as soon as possible following surface treatment.

For further details regarding known surface treatment methods, see, e.g., Green, M. D., et al., Characterisation and Comparison of Surface Modification on Homopolymer Polypropylene, a conference paper published in the proceedings of the 23rd Annual Meeting of the Adhesion Society (Myrtle Beach, S.C., USA Feb. 20-23, 2000), pp 541-543; and Plasma Processing of Advanced Materials, edited by Collins, G. A., et al., MRS Bulletin, August 1996, Chapter IV entitled 'Modification of Polymeric Material Surfaces with Plasmas' by Coates, D. M., et al., each of which are incorporated herein by reference.

2. Monolithic Column Fabrication

Generally, porous monoliths may be fabricated by flowing a monomer solution into a channel or conduit, and then activating the monomer solution to initiate polymerization. Various formulations and various activation means may be used. The ratio of monomer to solvent in each formulation may be altered to control the degree of porosity of the resulting monolith. A photoinitiator may be added to a monomer solution to permit activation by means of a lamp or other radiation source. If a lamp or other radiation source is used as the initiator, then photomasks may be employed to localize the formation of monoliths to specific areas within a fluidic separation device, particularly if one or more regions of the device body are substantially optically transmissive. Alternatively, chemical initiation or other initiation means may be used.

Numerous recipes for preparing monolithic columns suitable for performing chromatographic techniques are known in the art. In one embodiment a monolithic ion-exchange column may be fabricated with a monomer solution of about 2.5 ml of 50 millimolar neutral pH sodium phosphate, 0.18 grams of ammonium sulfate, 44 microliters of diallyl dimethylammonium chloride, 0.26 grams of methacrylamide, and 0.35 grams of piperazine diacrylamide. Further specific recipes are provided, for example, in Ngola, S. M., et al., Conduct-as-cast polymer monoliths as separation media for capillary electrochromatography, Anal. Chem., 2001, vol. 73, pp. 849-856; in Shediac, R., et al., Reversed-phase Electrochromatography of amino acids and peptides using porous polymer monoliths, J. Chrom. A., 2001, vol. 925, pp. 251-263; and in Ericson, C., et al., Electroosmosis- and pressure-driven chromatography in chips using continuous beds, Anal. Chem., 2001, vol. 72, pp. 81-87, each of which are incorporated herein by reference.

All references discussed herein are hereby incorporated by reference.

The particular devices and methods illustrated and described herein are provided by way of example only, and are not intended to limit the scope of the invention. The scope of the invention should be restricted only in accordance with the appended claims and their equivalents.

What is claimed is:

1. A device for performing a plurality of simultaneous liquid chromatographic separations, the device comprising:
   a plurality of batch-processed separation columns containing packed stationary phase material;
   at least one liquid-permeable frit adapted to retain the packed stationary phase material within the plurality of separation columns, the at least one liquid-permeable frit being compositionally different from the packed stationary phase material; and
   a body structure connecting the plurality of separation columns;
   wherein the device is adapted to ensure that each column of the plurality of batch-processed separation columns performs similarly in a parallel liquid chromatography system.

2. The device of claim 1, further comprising a plurality of sample inlet ports, wherein each separation column of the plurality of separation columns has an associated sample inlet port of the plurality of sample inlet ports.

3. The device of claim 2 wherein each separation column has a first end and a second end, and each sample inlet port of the plurality of sample inlet ports is disposed between the first end and the second end of its associated separation column.

4. The device of claim 2, further comprising a plurality of sample injection valves in fluid communication with the plurality of sample inlet ports.

5. The device of claim 1, further comprising:
   a common mobile phase source; and
   a fluidic distribution network disposed between the common mobile phase source and the plurality of separation columns, wherein each separation column of the plurality of separation columns is in fluid communication with the common mobile phase source through the fluidic distribution network.

6. The device of claim 5 wherein the at least one liquid-permeable frit comprises a first frit disposed between each separation column of the plurality of separation columns and the fluidic distribution network, and a second frit disposed downstream of each separation column of the plurality of separation columns.

7. The device of claim 5 wherein the fluidic distribution network is contained within the body structure.

8. The device of claim 7 wherein the fluidic distribution network is microfluidic.

9. The device of claim 1, further comprising a plurality of detection regions permitting detection of at least one property of a substance received from the plurality of separation columns, wherein each separation column of the plurality of separation columns has an associated detection region of the plurality of detection regions.

10. The device of claim 1 wherein each column of the plurality of columns has a characteristic fluidic impedance, and the fluidic impedance of each column of the plurality of columns varies by less than about five percent.

11. The device of claim 1 wherein each column of the plurality of columns has a characteristic fluidic impedance, and the fluidic impedance of each column of the plurality of columns varies by less than about two percent.

12. The device of claim 1 wherein the body structure comprises at least one surface adapted to threadlessly engage a mating surface of an external clamping apparatus.

13. The device of claim 1, further comprising at least one threaded endfitting.

14. The device of claim 1 wherein each separation column of the plurality of separation columns is contained within a substantially cylindrical tube.

15. The device of claim 1 wherein each separation column of the plurality of separation columns is microfluidic.

16. The device of claim 1 wherein each separation column of the plurality of separation columns has a substantially rectangular cross-section.

17. The device of claim 1 wherein the liquid-permeable frit comprises a microporous polymeric material.

18. The device of claim 1 wherein the liquid-permeable frit comprises a metallic material.

19. The device of claim 1 wherein the liquid-permeable frit comprises a sintered material.

20. The device of claim 1 wherein the plurality of columns, the at least one frit, and the body structure are integrated into a disposable cartridge.

21. The device of claim 1 wherein the packed stationary phase material comprises packed particles, and the particles comprise silica, alumina, zirconium, or polymeric materials.

22. The device of claim 21 wherein the packed particles are unsintered.

23. The device of claim 21 wherein at least some of the packed particles include surface functional groups.

24. The device of claim 23 wherein the surface functional groups are selected from the group consisting of: alkyl, cyano, amino, nitro, hydroxy, phenyl, phenyl-hexyl, and sulfonic acid.

25. The device of claim 1 wherein the body structure comprises a polymeric material.

26. The device of claim 1 wherein the body structure comprises a plurality of substantially planar device layers.

27. The device of claim 26 wherein the plurality of substantially planar device layers includes at least one stencil layer having at least one channel defined through the entire thickness of the at least one stencil layer.

28. The device of claim 26 wherein the plurality of substantially planar device layers comprise polymeric materials and are adhesivelessly bound together.

29. The device of claim 1 wherein each separation column of the plurality of separation columns comprises a channel bounding material that is irreversibly affixed to the body structure.

30. The device of claim 1 wherein the device is adapted to perform pressure-driven chromatographic separation.

31. The device of claim 1 wherein the device is adapted to operate at an internal pressure of at least about 100 psi.

32. A fluidic system comprising:
the device of claim 1;
a common mobile phase source;
a fluidic distribution network disposed between the common mobile phase source and the plurality of separation columns, wherein each separation column of the plurality of separation columns is in fluid communication with the common mobile phase source through the fluidic distribution network;
a plurality of parallel fluid flow paths disposed downstream of the plurality of separation columns, each parallel fluid flow path being in fluid communication with a different separation column of the plurality of separation columns; and
a plurality of detection regions disposed downstream of the plurality of parallel fluid flow paths and permitting detection of at least one property of a substance received from the plurality of separation columns;
wherein the fluidic distribution network defines a first volume, the plurality of parallel fluid flow paths defines a second volume, the plurality of separation columns defines a third volume, and the third volume is substantially greater than each of the first volume and the second volume.

33. The system of claim 32 wherein the third volume is at least about three times greater than each of the first volume and the second volume.

34. The device of claim 32 wherein the third volume is at least about six times greater than each of the first volume and the second volume.

* * * * *

UNITED STATES PATENT AND TRADEMARK OFFICE
CERTIFICATE OF CORRECTION

PATENT NO. : 7,261,812 B1 Page 1 of 1
APPLICATION NO. : 11/638258
DATED : August 28, 2007
INVENTOR(S) : Christoph D. Karp et al.

It is certified that error appears in the above-identified patent and that said Letters Patent is hereby corrected as shown below:

On title page
Item [56]
References Cited, Other Publications, add: -- Olsen, Kimberly G., et al., *Immobilization of DNA Hydrogel Plugs in Microfluidic Channels*, Analytical Chemistry, Vol. 74, No. 6, March 15, 2002, pp. 1436-1441 --..

References Cited, Other Publications, add: -- Moore, Roger E., et al., *A Microscale Electrospray Interface Incorporating a Monolithic, Poly(styrene-divinylbenzene) Support for On-Line Liquid Chromatography/Tandem Mass Spectrometry Analysis of Peptides and Proteins*, Analytical Chemistry, Vol. 70, No. 23, December 1, 1998 --.

References Cited, Other Publications, add: -- Yu, Cong et al., *Monolithic Porous Polymer for On-Chip Solid Phase Extraction and Preconcentration Prepared by Photoinitiated in Situ Polymerization Within a Microfluidic Device*, Analytical Chemistry, Vol. 73, No. 21, November 1, 2001, pp. 5088-5096 --.

Column 28, line 25: "8" longx2" outside" should be --8" long x 2" outside --.

Signed and Sealed this

Fourth Day of December, 2007

JON W. DUDAS
*Director of the United States Patent and Trademark Office*